(12) United States Patent
Bell et al.

(10) Patent No.: US 7,863,302 B2
(45) Date of Patent: Jan. 4, 2011

(54) COMPOUNDS AND METHODS FOR MODULATING FX-RECEPTORS

(75) Inventors: Michael Gregory Bell, Indianapolis, IN (US); Michael James Genin, Zionsville, IN (US); Peter Ambrose Lander, Indianapolis, IN (US); Lindsay Scott Stelzer, Indianapolis, IN (US); Robert Anthony Doti, Indianapolis, IN (US); Francisco Javier Agejas-Chicharro, Alcobendas (ES); Ana Belen Bueno Melendo, Alcobendas (ES); Peter Rudolph Manninen, Brownsburg, IN (US); Jason Matthew Ochoada, Greenwood, IN (US); Quanrong Shen, Fishers, IN (US); Alan M. Warshawsky, Carmel, IN (US); Tianwei Ma, Carmel, IN (US); Ryan Edward Stites, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 333 days.

(21) Appl. No.: 12/159,224

(22) PCT Filed: Feb. 2, 2007

(86) PCT No.: PCT/US2007/061515

§ 371 (c)(1),
(2), (4) Date: Jun. 26, 2008

(87) PCT Pub. No.: WO2007/092751

PCT Pub. Date: Aug. 16, 2007

(65) Prior Publication Data

US 2008/0306125 A1    Dec. 11, 2008

Related U.S. Application Data

(60) Provisional application No. 60/765,407, filed on Feb. 3, 2006, provisional application No. 60/806,310, filed on Jun. 30, 2006.

(51) Int. Cl.
| | |
|---|---|
| A61K 31/4245 | (2006.01) |
| A61K 31/422 | (2006.01) |
| A61K 31/428 | (2006.01) |
| A61P 3/10 | (2006.01) |
| C07D 261/06 | (2006.01) |
| C07D 275/04 | (2006.01) |
| C07D 277/20 | (2006.01) |

(52) U.S. Cl. .................. 514/364; 514/365; 514/378; 548/144; 548/201; 548/207; 548/247

(58) Field of Classification Search .................. None
See application file for complete search history.

(56) References Cited

FOREIGN PATENT DOCUMENTS

| WO | WO 03/015771 | 2/2003 |
|---|---|---|
| WO | WO 2004/048349 | 6/2004 |

*Primary Examiner*—Kamal A Saeed
(74) *Attorney, Agent, or Firm*—Francis O. Ginah

(57) ABSTRACT

Compounds of formula and their pharmaceutical compositions and methods of use are disclosed as useful for treating dyslipidemia and related diseases.

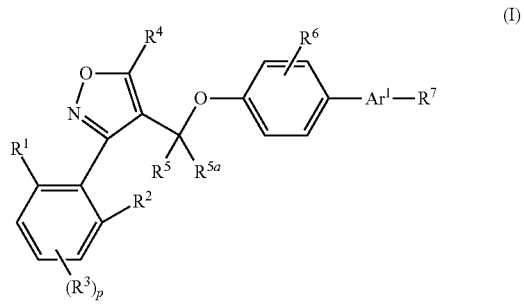

(I)

15 Claims, No Drawings

COMPOUNDS AND METHODS FOR MODULATING FX-RECEPTORS

This is the national phase application, under 35 USC 371, for PCT/US2007/061515, filed 2 Feb. 2007, which claims the benefit, under 35 USC 119(e), of U.S. provisional applications 60/765,407, filed 3 Feb. 2006, and 60/806,310, filed 30 Jun. 2006.

FIELD OF THE INVENTION

The current invention relates to the fields of medicinal organic chemistry, pharmacology and medicine.

BACKGROUND OF THE INVENTION

Dyslipidemia and diseases related to dyslipidemia e.g. atherosclerosis, coronary artery disease, stroke, etc., are major causes of death, morbidity, and economic loss. Plasma lipids, especially cholesterol fractions, are recognized as having a significant role in cardiovascular health. Favorable modulation of plasma lipid such as triglycerides, HDL cholesterol, and LDL cholesterol is desirable.

International application WO 03/015771 A1 discloses certain isoxazoles for use in treating diseases mediated by the FXR NR1H4 receptor. International application WO 00/37077 discloses certain isoxazoles that bind to the farnesoid X receptor (FXR). International application WO 2004/048349 A1 discloses compounds useful as farnesoid X receptor agonists. International application WO 98/28269 discloses compounds useful as factor Xa inhibitors.

The nuclear hormone receptors, FXRs, regulate the metabolism of plasma cholesterol and HDL. Thus, compounds which modulate the FXRs would enhance the profile of lipid regulation, particularly increased HDL levels. Such compounds are desirable and would be useful for treatment of disorders characterized by or resulting from an undesirable lipid profile including dyslipidemia, atherosclerosis, diabetes and related diseases. The present invention provides novel, selective and potent FXR agonists for beneficial regulation of lipid profiles including raising HDL levels.

SUMMARY OF THE INVENTION

The present invention provides a compound of formula

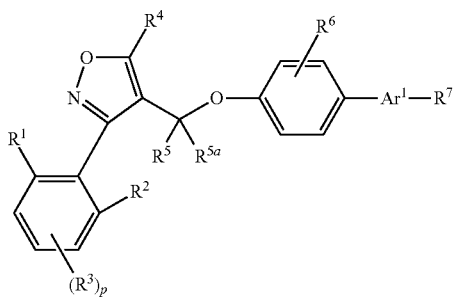

p is 0 or 1;
$R^1$ and $R^2$ are independently selected from the group consisting of hydrogen, —$C_1$-$C_6$ alkyl, —$C_1$-$C_6$ haloalkyl, —$C_1$-$C_6$ alkoxy-, —$C_1$-$C_6$ haloalkoxy-, halo, —$SR^{11}$, and —S—$C_1$-$C_3$ haloalkyl;
each $R^3$ is independently selected from the group consisting of —$C_1$-$C_6$ alkyl, —$C_1$-$C_6$ haloalkyl, —$C_1$-$C_6$ alkoxy-, —$C_1$-$C_6$ haloalkoxy-, and halo;
$R^4$ is selected from the group consisting of hydrogen, —$C_1$-$C_6$ alkyl, —$C_1$-$C_6$ haloalkyl, —$C_3$-$C_8$ cycloalkyl, —$C_4$-$C_8$ alkylcycloalkyl, —$C_1$-$C_6$ alkoxy-, and —$C_1$-$C_6$ haloalkoxy-;
$R^5$ and $R^{5a}$ are independently selected from the group consisting of hydrogen, and —$C_1$-$C_3$ alkyl;
$R^6$ is selected from the group consisting of hydrogen, —$C_1$-$C_6$ alkyl, —$C_1$-$C_6$ haloalkyl, and halo;
$Ar^1$ is selected from the group consisting of indolyl, pyridinyl, thienyl, benzothienyl, indazolyl, benzothiazolyl, benzisoxazolyl, benzofuranyl and thiazolyl, each optionally substituted with one or two groups independently selected from the group consisting of hydroxy, —$C_1$-$C_6$ alkyl, $C_3$-$C_8$ cycloalkyl, —$C_1$-$C_4$ alkylSO$_2$$C_1$-$C_2$ alkyl, —$C_1$-$C_4$ alkylSC$_1$-$C_2$ alkyl, —$C_1$-$C_4$ alkylNR$^{10}$R$^{11}$, phenyl, —$C_1$-$C_4$ alkyl-O—$C_1$-$C_4$ alkyl, and —NHC(O)R$^{10}$;
$R^7$ is selected from the group consisting of —$CH_2COOR^{10}$, —$COOR^{10}$, —$CONR^{11}R^{11}$, —C(O)NHSO$_2$$C_1$-$C_4$ alkyl, —C(O)NHSO$_2$R$^{12}$, oxadiazolethione, and oxadiazolone;
each $R^{10}$ is independently selected from the group consisting of hydrogen, —$C_1$-$C_4$ alkyl, and phenyl;
each $R^{11}$ is independently hydrogen, or —$C_1$-$C_6$ alkyl;
$R^{12}$ is —$C_1$-$C_6$ alkyl or phenyl optionally substituted with —$C_1$-$C_3$ alkyl, or a pharmaceutically acceptable salt thereof.

The compounds of the invention are modulators of FXRs. As such, the compounds of the invention are useful for beneficially altering lipid profiles, including but not limited to lowering total cholesterol, lowering LDL cholesterol, lowering VLDL cholesterol levels, raising HDL levels, lowering triglyceride levels and beneficially sensitizing the effects of insulin. Thus the present invention provides a method for treating FXR mediated conditions such as dyslipidemia and diseases related to dyslipidemia comprising administering a therapeutically effective amount of a compound of the invention to a patient in need thereof.

The present invention also provides a pharmaceutical composition comprising a compound of the invention and a pharmaceutically acceptable carrier.

The present invention also relates to the use of a compound of the invention for the manufacture of a medicament. The present invention also provides for the use of a compound of the invention for the manufacture of a medicament for treating FXR mediated conditions described herein.

DETAILED DESCRIPTION OF THE INVENTION

The terms "modulation" and "modulator" as used herein refer to beneficial regulation of genes and enzymatic processes resulting in or from agonism of the FXR receptor. FXR modulates key genes in multiple metabolic pathways, including cholesterol, triglyceride, bile acid and glucose metabolism.

The term "dyslipidemia" as used herein refers to abnormality in, or abnormal amounts of lipids and lipoproteins in the blood and the disease states resulting, caused by, exacerbated by, or adjunct to such abnormality (see *Dorland's Illustrated Medical Dictionary, 29th edition,* W. B Saunders publishing Company, New York, N.Y.). Disease states encompassed within the definition of dyslipidemia as used herein include hyperlipidemia, hypertriglyceremia, low plasma HDL, high plasma LDL, high plasma VLDL, liver cholestasis, and hypercholesterolemia.

The phrase "diseases related to dyslipidemia" as used herein refers to cardiovascular diseases including but not limited to atherosclerosis, thrombosis, coronary artery disease, stroke, and hypertension. Diseases related to dyslipidemia also include diabetes, insulin resistance, and complications thereof. Complications of diabetes include but are not limited to diabetic retinopathy and obesity.

As used herein, the term "patient" includes human and non-human animals such as companion animals (dogs and cats and the like) and livestock animals.

The terms "treatment" "treat" and "treating" include inhibiting, ameliorating, halting, slowing, and reversing the progression of, or reducing the severity of, pathological symptoms of dyslipidemia and diseases related to dyslipidemia.

As used herein, the term "therapeutically effective amount" means an amount of a compound of the invention that is part of an approved therapeutic regimen, or is determined by a qualified prescriber to be sufficient taken as directed, for treating a condition, or detrimental effects thereof herein described.

The term "pharmaceutically acceptable" is used herein as an adjective and means substantially non-deleterious to the recipient patient.

The term "$C_1$-$C_6$ alkyl" or the like (e.g. —$C_1$-$C_2$ alkyl, —$C_1$-$C_3$ alkyl, —$C_1$-$C_4$ alkyl, —$C_1$-$C_5$ alkyl, etc) represents a straight or branched hydrocarbon moiety having from 1 to 6 (or as indicated) carbon atoms, including but not limited to methyl, ethyl, n-propyl, isopropyl, n-butyl, isobutyl, sec-butyl, t-butyl, and the like. An optionally substituted alkyl group is divalent when connected to the substrate or molecular backbone.

The term "$C_3$-$C_8$ cycloalkyl" or similar terms refer to a saturated carbocyclic ring having from 3 to 8 carbon atoms (or as indicated), including but not limited to cyclopropyl, cyclopentyl and cyclohexyl.

The term "$C_4$-$C_8$ alkylcycloalkyl" and the like (depending on indicated number of carbon atoms) as used herein refer to the combination of an alkyl and a cycloalkyl group such that the total number of carbon atoms is 4 to 8 or as indicated and the entire group is bonded to the substrate via the alkyl portion. For example, $C_4$-$C_8$ alkylcycloalkyl includes cycloalkyl rings (e.g. $C_3$-$C_7$ cycloalkyl) bonded to at least one carbon atom, such that the total number of carbon atoms is anywhere from 4 to 8 as in for example, —$CH_2$cyclopropyl.

The term "halo" means halogens including iodo, chloro, bromo and fluoro.

The term "$C_1$-$C_6$ haloalkyl" or the like (e.g. $C_1$-$C_3$ haloalkyl) refers to a $C_1$-$C_6$ alkyl (or as indicated) group substituted with one, two, three or more halogen atoms as indicated or chemically appropriate. Examples of $C_1$-$C_6$ haloalkyl include but are not limited to trifluoromethyl, chloroethyl, and 2-chloropropyl.

A "$C_1$-$C_6$ alkoxy" group or the like (e.g. $C_1$-$C_3$ alkoxy, $C_2$-$C_6$ alkoxy, etc) is a $C_1$-$C_6$ alkyl (or as indicated) moiety connected through an oxy linkage. Examples of alkoxy groups include but are not limited to methoxy (—OMe), ethoxy(—OEt), propoxy (—OPr), isopropoxy (—OiPr), butoxy (—OBu), etc.

The term "$C_1$-$C_6$ haloalkoxy" or the like (e.g. $C_1$-$C_3$ haloalkoxy) encompasses $C_1$-$C_6$ alkoxy wherein one or more of the hydrogen have been replaced with halogens. Examples of haloalkoxy groups include difluoromethoxy, trifluoromethoxy, 2-haloethoxy, 2,2,2-trifluoroethoxy, 4,4,4-trifluorobutoxy, up to and including like groups having the indicated number of carbon atoms.

A compound of the invention as illustrated by the invention may occur as any one of its isomers all of which are objects of the invention. Certain compounds of the invention may possess one or more chiral centers, and thus, may exist in optically active forms. All such isomers as well as the mixtures thereof are within the ambit of the present invention. If a particular stereoisomer is desired, it can be prepared by methods well known in the art.

PREFERRED EMBODIMENTS OF THE INVENTION

Preferably p is 0 or 1. More preferably p is 0

Preferably $R^1$ and $R^2$ are each independently selected from the group consisting of hydrogen, $C_1$-$C_3$ alkyl, —$C_1$-$C_3$ haloalkyl, $C_1$-$C_3$ alkoxy-, $C_1$-$C_3$ haloalkoxy-, —$SC_1$-$C_3$ alkyl, —$SC_1$-$C_3$ haloalkyl, and halo. More preferred $R^1$ and $R^2$ groups are independently selected from the group consisting of hydrogen, chloro, fluoro, trifluoromethyl, thiotrifluoromethyl, and trifluoromethoxy.

A preferred $R^3$ group is selected from the group consisting of $C_1$-$C_4$ alkyl, —$C_1$-$C_3$ haloalkyl, $C_1$-$C_3$ alkoxy-, $C_1$-$C_3$ haloalkoxy-, and halo. More preferred is an $R^3$ group selected from the group consisting of chloro, fluoro, trifluoromethoxy, thiotrifluoromethyl, and trifluoromethyl. Most preferably, $R^3$ is absent (p is 0).

Preferably, $R^4$ is selected from H, methyl, ethyl, isopropyl, cyclopropyl, and methylcyclopropyl. Most preferably $R^4$ is isopropyl or cyclopropyl.

Preferably, $R^5$ and $R^{5a}$ are each independently selected from the group consisting of hydrogen, methyl and ethyl. More preferably, $R^5$ and $R^{5a}$ are both hydrogen.

A preferred $R^6$ group is selected from the group consisting of hydrogen, halo, and $C_1$-$C_3$ alkyl. More preferably, $R^6$ is hydrogen or methyl.

A preferred $Ar^1$ group is selected from the group consisting of optionally substituted indolyl, thienyl, pyridinyl, benzothienyl, indazolyl, benzothiazolyl, benzisoxazolyl, benzofuranyl and thiazolyl each attached to the chain of the compound of the invention at any available carbon atom. More preferably $Ar^1$ is indolyl, thienyl, benzothienyl, and thiazolyl each optionally substituted with one or two groups independently selected from the group consisting of halo, $C_1$-$C_5$ alkyl, —$C_1$-$C_3$ alkylSO$_2$$C_1$-$C_3$ alkyl, —$C_1$-$C_3$ alkyl-O—$C_1$-$C_3$ alkyl, —$C_1$-$C_3$ alkyl-S—$C_1$-$C_3$ alkyl, —$C_1$-$C_3$ alkylNH ($C_1$-$C_3$ alkyl), —$C_1$-$C_3$ alkylN($C_1$-$C_3$ alkyl)$_2$, phenyl, and —NHC(O)$C_1$-$C_3$ alkyl wherein said substitution may be on carbon and/or nitrogen. More preferably, $Ar^1$ is substituted once at the nitrogen atom of a nitrogen containing group.

A preferred $R^7$ substituent is selected from the group consisting of —COOH, —C(O)NHSO$_2$$C_1$-$C_3$ alkyl, —C(O)NHSO$_2$-phenyl, —C(O)NHSO$_2$-phenylCH$_3$, and —COOCH$_3$. A more preferred $R^7$ group is —COOH.

Each $R^{10}$ is preferably hydrogen, or $C_1$-$C_6$ alkyl.

Each $R^{11}$ is preferably $C_1$-$C_6$ alkyl.

$R^{12}$ is preferably phenyl optionally substituted with $C_1$-$C_3$ alkyl.

Also preferred is a compound of the invention wherein:
p is 0, or 1;
$R^1$ and $R^2$ are independently selected from the group consisting of hydrogen, fluoro, chloro, CF$_3$, and —OCF$_3$,
$R^3$ is fluoro, chloro, CF$_3$, SCF$_3$, or OCF$_3$;
$R^4$ is H, isopropyl or cyclopropyl;
$R^5$ and $R^{5a}$ are each independently selected from H or methyl;
$Ar^1$ is indolyl, pyridinyl, thienyl, thiazolyl and benzothienyl each optionally substituted with one group selected from the group consisting of $C_1$-$C_4$ alkyl, CF$_3$, —CH$_2$CH$_2$SC$_{1-2}$, —CH$_2$CH$_2$OCH$_3$, —CH$_2$CH$_2$SO$_2$Cl$_3$, —CH$_2$CH$_2$N(CH$_3$)$_2$, and phenyl;
$R^6$ is hydrogen, or methyl;

$R^7$ is —COOH, —COOC$_1$-C$_2$ alkyl, —CONHSO$_2$C$_1$-C$_4$ alkyl, —CONHSO$_2$phenyl, CONHSO$_2$phenylmethyl, oxadiazolone, and thiadiazolone;
each $R^{10}$ is independently hydrogen or C$_1$-C$_6$ alkyl; and
each $R^{11}$ is independently hydrogen or C$_1$-C$_6$ alkyl.

More preferred is a compound of the invention wherein each p is 0; $R^1$ and $R^2$ are independently selected from the group consisting of chloro, fluoro, trifluoromethyl, and trifluoromethoxy; $R^4$ is isopropyl or cyclopropyl; $R^5$ and $R^{5a}$ are both hydrogen; $R^6$ is hydrogen, methyl, ethyl or chloro; Ar$^1$ is thienyl, benzothienyl, indolyl or thiazolyl, each bound at any available carbon atom and each optionally substituted with a group selected from methyl, ethyl, propyl, butyl, isopropyl, cyclopropyl, —CH$_2$CH$_2$SO$_2$CH$_3$, —CH$_2$CH$_2$N(CH$_3$)$_2$, —CH$_2$CH$_2$SCH$_2$, —CH$_2$CH$_2$OCH$_2$, and phenyl; and $R^7$ is —COOH or —COOMe.

Especially preferred are compounds of the invention exemplified herein.

The compounds of the invention (formula I) may be prepared by a variety of procedures known in the art and those described below. The products of each step in the Scheme below can be recovered by conventional methods including extraction, evaporation, precipitation, chromatography, filtration, trituration, crystallization, and the like. In the scheme below all substituents, unless otherwise indicated, are as previously defined and suitable reagents are well known and appreciated in the art.

Scheme 1

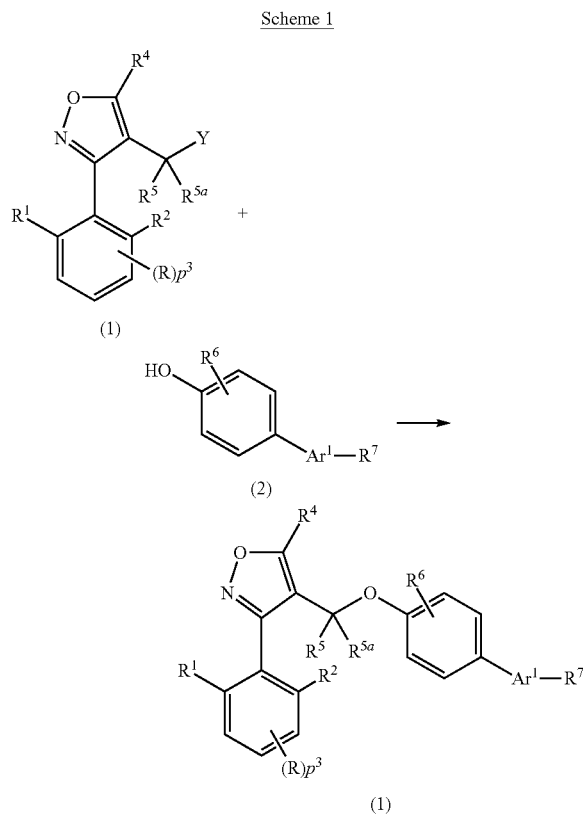

Scheme 1 depicts the reaction of an appropriate compound of formula (1) with an appropriate compound of formula (2) to give a compound of formula (I). The reaction in Scheme 1 can be carried out by at least two variants discussed below.

In the first variant, an appropriate compound of formula (1) is one in which $R^1$, $R^2$, $R^3$, p, $R^4$, $R^5$, and $R^{5a}$ are defined for formula I, and Y is —OH and an appropriate compound of formula (2) is one in which $R^6$, $R^7$, and Ar$^1$ are as defined in formula (1) or a group which gives rise to $R^7$ as defined in formula (1), for example, by formation of an ester, amide, sulfonamide, or acid.

For example, a compound of formula (1) is reacted with a compound of formula (2) in a Mitsunobu reaction using a suitable diazo reagent, such as DEAD or ADDP, and the like, and a suitable phosphine reagent such as triphenyl phosphine or tributylphosphine, and the like. Such reactions are carried out in a suitable solvent, such as toluene, tetrahydrofuran, and the like. Generally, the reactions are carried out at temperatures of from about 0° C. to 50° C. Typical stoichiometry for this reaction based on the compound of formula (1) is about 1 to 2 equivalents of a compound of formula (2) and about 1 to 2 equivalents each of the diazo and phosphine reagents.

In the second variant, an appropriate compound of formula (1) in which $R^1$, $R^2$, $R^3$, p, $R^4$, $R^5$, and $R^{5a}$ are defined for formula I and Y is a leaving group and an appropriate compound of formula (2) is as defined above are reacted to form the compound of formula (1) with appropriate protections and/or deprotections or other processing steps known to one of skill in the art or disclosed herein. Suitable leaving groups are well-known in the art and include halides, particularly chloro, bromo, and iodo; and sulfonate esters, such as brosyl, tosyl, methanesulfonyl, and trifluoromethanesulfonyl.

For example, a compound of formula (1) is reacted with a compound of formula (2) in a suitable solvent, such as acetonitrile, dimethylformamide, tetrahydrofuran, pyridine, methylethyl ketone and the like. As will be readily appreciated an excess of a suitable base is usually used in the reaction, including sodium hydride, potassium carbonate, sodium carbonate, cesium carbonate, sodium bicarbonate, triethylamine, diisopropyethylamine. Such reactions generally are carried out at temperatures of about room temperature to about the reflux temperature of the chosen solvent and typically use from about 1 to 2 equivalents of the compound of formula (2).

Additionally, compounds of formula (1) wherein $R^7$ is an ester can be converted to compounds of formula (1) wherein $R^7$ is an acid via methods well known to one of ordinary skill in the art. For example, hydrolysis of simple alkyl esters in suitable solvents such as THF, methanol, ethanol, water mixtures at temperatures from about 25-100C. with suitable bases. (NaOH, LiOH). In a modification of this hydrolysis method the microwave may be used as an energy/heat source, especially when the ester is sterically hindered. For example a laboratory microwave utilizing the lowest power setting at about 125° C. for about 20 minutes in solvent mixtures described above is useful. When $R^7$ is a t-butyl ester the acid can be formed under acidic conditions well known to those skilled in the art.

Additionally, compounds of formula (1) wherein $R^7$ is a carboxylic acid can be converted to compounds of formula (1) wherein $R^7$ is an amide or sulfonamide by coupling procedures well known in the art. For example, a compound of formula (1) wherein $R^7$ is an acid is reacted with an amine or sulfonamide compound in the presence of a coupling agent such as dicyclohexylcarbodiimide, 1-[3-(dimethylamino)propyl]-3-ethylcarbodiimide hydrochloride, and the like, and optionally N,N-dimethylaminopyridine and/or an amine base, such as triethylamine, diisopropylethylamine, and the like, in a suitable solvent, such as DMF, THF, and the like. Such reactions are generally carried out at a temperatures of about room temperature to about 60-80° C.

In an optional step, a pharmaceutically acceptable salt of a compound of formula (1) is formed. The formation of such salts is well known and appreciated in the art.

As will be readily appreciated compounds of formula (1) and (2) can be readily prepared by methods that are well-known and established in the art including methods and procedures similar to those described herein. For example, compounds of formula (1) are prepared by the reaction of optionally substituted benzaldehydes with hydroxylamine followed by chlorination with a suitable chlorinating agent, such as N-Chloro succinimide, to afford chloroximes (see for example *J. Med. Chem.* 2000, 43 (16), 2971-2974). Reaction of the chloroximes and an appropriate β-ketoester under basic conditions with a suitable base, such as triethylamine or sodium methoxide, gives the penultimate isoxazole esters. The esters can be reduced to the alcohol compounds of formula (1) with well known methods (e.g. DIBAL-H, LAH) and subsequently converted to a leaving group. Compounds of formula (2) are prepared by carbon-carbon bond formation/coupling reactions. Also, it is recognized that the steps required to prepare a compound of formula (1) can be carried out in any order. For example, including reaction of a partial compound of formula (2) with a compound of formula (1), such that the later carried out carbon-carbon bond formation/coupling reaction provide a compound of formula I. More specifically, a compound of formula (3) can be reacted with a compound of formula (1) as described above to afford compounds of formula (4) which can be converted to compounds of formula (1) via carbon-carbon bond forming reactions with compounds of formula (5) (Scheme 2).

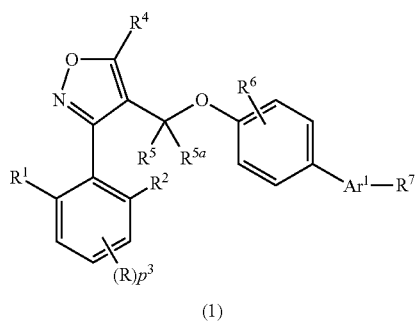

(1)

Alternatively, the sequence of reactions can be adjusted to prepare compounds of formula (1). For example, as shown in Scheme 3, compounds of formula (6) can be reacted with compounds of formula (1) to provide compounds of formula (7). Carbon-carbon bond forming reactions between compounds of formula (7) and compounds of formula (8) provide compounds of formula (1).

Scheme 2

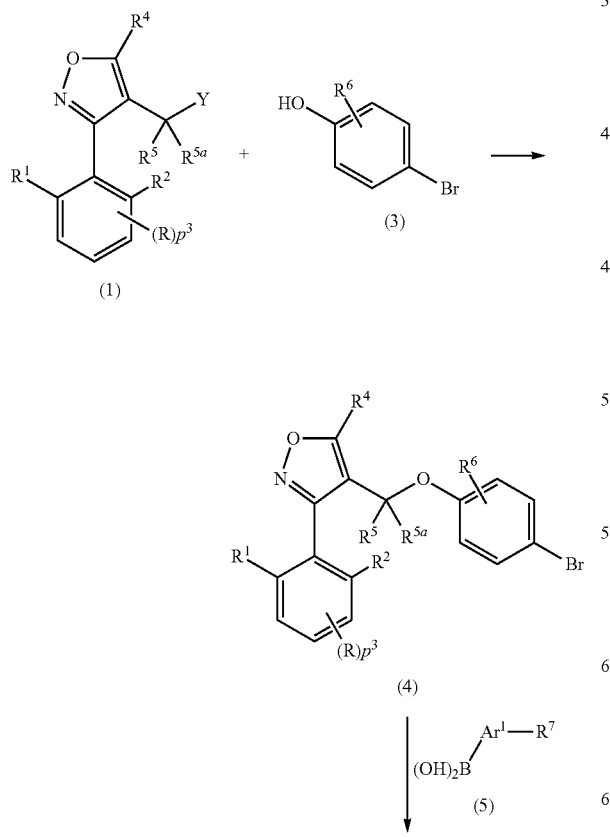

Scheme 3

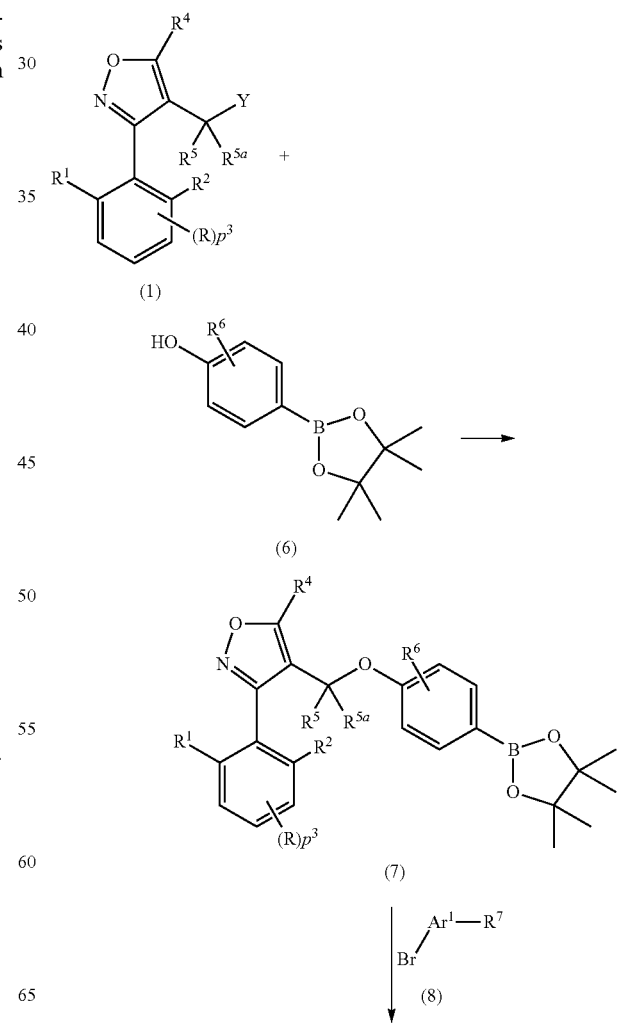

-continued

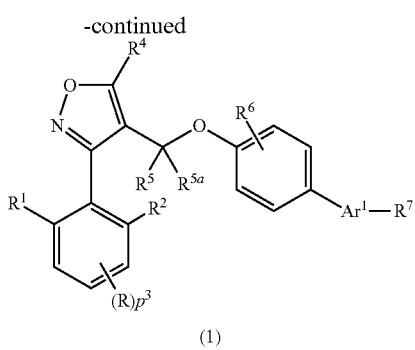

(1)

As will be readily understood the steps to prepare the compounds of the invention are dependent upon the particular compound being synthesized, the starting compound, and the relative lability of the substituted moieties. Also contemplated are various protection and deprotection steps as may be required or beneficial for carrying out the reactions above. The selection and use of suitable protecting groups is well known and appreciated in the art (see for example, *Protecting Groups in Organic Synthesis*, Theodora Greene (Wiley-Interscience)).

Certain compounds of the invention exist as solid amorphous or crystalline forms. A compound of the invention may also exist in multiple crystalline forms wherein one or more of the crystalline forms are preferred over others on account of having more desirable properties such as, for example, improved solubility, improved bioavailability and/or improved stability. All such crystalline forms are within the ambit of the present invention. For example, the compound of example 101 has been found to exist in two forms (forms I and II).

The present invention is further illustrated by the examples and preparations disclosed herein. These examples and preparations are illustrative only and are not intended to limit the invention in any way. The terms used in the examples and preparations have their normal meanings unless otherwise designated. All chromatography is performed using silica gel, unless otherwise indicated.

Assay

The following assay protocols and results demonstrate the utility, in vitro and in vivo efficacy of the compounds and/or methods of the current invention and are provided for the purpose of illustration and not meant to be limiting in any way.

FXR-SRC-1 Cofactor Recruitment Assay

Compounds are tested in concentration-response curves by an FXR-SRC-1 Cofactor Recruitment assay using the Alpha (Amplified Luminescent Proximity Homogeneous Assay) Screen technology according to the manufacturer instructions (Perkin Elmer). Briefly, purified 6-HIS-tagged human FXR ligand-binding domain (amino acids 242-472), purified GST-tagged human SRC-1 nuclear receptor-interacting domain (amino acids 220-394), Nickel Chelate donor beads (Perkin Elmer) and Anti-GST antibody acceptor beads (Perkin Elmer) are mixed together and 12 µL per well is aliquoted into 384 well plates. Add compounds in 3 µL per well for a total assay volume of 15 µL and incubate at room temperature in the dark for 4 hours. After incubation, compounds that bind FXR and induce the interaction between the FXR and SRC-1 would bring the two bead types into proximity generating luminescence that is quantified using a Packard Fusion instrument. Calculate $EC_{50}$ values for each test compound. Compounds of the invention are found to be effective in the SRC-1 FXR interaction assay with $EC_{50}$ of about 365-3000 nM. For example the compound of Example 7 exhibited an $EC_{50}$ of 1300 nM.

LDLR-/- Serum Lipid Modulation

Acquire LDLR-/- mice from Jackson Laboratories (Stock number 002207, Bar Harbor, Me., USA). Acclimate animals for one week prior to study initiation. House mice individually in polycarbonate cages with filter tops, and maintain mice on a 12:12 hour light-dark cycle (lights on at 6:00 AM) at 21° C. Provide deionized water ad libitum and maintain for two weeks on 'western diet' TD 98137 Diet (42% fat, 0.15% cholesterol, Harlan Teklad) ad libitum. Optimize groups of five ten-week-old male LDLR-/- mice based on serum triglyceride and cholesterol levels. Dose groups once daily by oral gavage with various doses of the test compound for seven days. At the end of the seven-day dosing period, collect blood by tail clip for clinical chemistry assessment. Measure serum triglycerides, glucose, and total cholesterol using standard clinical chemistry instrumentation and reagents (Roche Diagnostic, Indianapolis, Ind., USA). Asphyxiate mice in a $CO_2$ chamber. Perform cardiac puncture to collect blood samples for serum FPLC analysis. Assay pooled serum samples for lipoprotein cholesterol fraction values (VLDL, LDL, HDL) by separation on a size exclusion column (Superose® 6HR, Pharmacia Biotech AB, Uppsala, Sweden) with in-line determination of cholesterol.

In this assay, tested compounds of the invention reduce total cholesterol tip to 80% and triglycerides up to 90% when dosed at 10 mg/kg. More specifically the compound of Example 7 lowers total cholesterol 63% and triglycerides 61% when dosed at 10 mg/kg.

The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.1 mg to about 500 mg/day of a compound of the present invention. Preferred daily doses generally will be from about 1 mg to about 250 mg/day.

The compounds of this invention may be administered by a variety of routes including oral, rectal, transdermal, subcutaneous, intravenous, intramuscular, and intranasal. These compounds preferably are formulated prior to administration. The selection of appropriate dose and route of administration will be decided by the attending physician. Thus, another aspect of the present invention is a pharmaceutical composition comprising an effective amount of a compound of the invention, or a pharmaceutically acceptable salt thereof, and a pharmaceutically acceptable carrier, diluent, or excipient.

One skilled in the art can readily select the proper form and route of administration depending upon the particular characteristics of the compound selected, the disorder or condition to be treated, the stage of the disorder or condition, and other relevant circumstances. (Remington's Pharmaceutical Sciences, 118th Edition, Mack Publishing Co. (1990)). The pharmaceutical compositions of the present invention may be adapted for these various routes and may be administered to the patient, for example, in the form of tablets, capsules, cachets, papers, lozenges, wafers, elixirs, ointments, transdermal patches, aerosols, inhalants, suppositories, solutions, and suspensions.

The total active ingredients in such composition comprises from 0.1% to 99.9% by weight of the formulation.

Compounds of the invention may be formulated as elixirs or solutions for convenient oral administration or as solutions appropriate for parenteral administration, for example, by intramuscular, subcutaneous or intravenous routes. Additionally, the compounds may be formulated as sustained release dosage forms and the like. The formulations can be constituted such that they release the active ingredient only or preferably in a particular physiological location, possibly over a period of time. The coatings, envelopes, and protective matrices may be made, for example, from polymeric substances or waxes.

PREPARATIONS AND EXAMPLES

The following preparations and examples further illustrate the invention.

The abbreviations used herein are defined according to Aldrichimica Acta, Vol 17, No. 1, 1984. Other abbreviations are defined as follows. "ACN" is acetonitrile; "AcOH" is acetic acid; "MeOH" is methanol; "EtOH" is ethanol; "EtOAc" is ethyl acetate; "ADDP" is 1,1-(Azodicarbonyl) dipiperidine; "DEAD" is diethyl azodicarboxylate; "TBME" is t-butylmethylether; "(OAc)" is acetate; "DMSO-$d_6$" is deuterated dimethylsulfoxide; "PCy$_3$" is tricyclohexyl phosphine, "dba" is dibenzylideneacetone; "NaOEt" is sodium ethoxide.

All compounds are named using ChemDraw Ultra 7.0 available from CambridgeSoft Corporation, Cambridge, Mass.

Preparation 1

3-(2,6-Dichloro-phenyl)-5-isopropyl-isoxazole-4-carbinol

The title compound is prepared as described in *J. Med. Chem.* 2000, 43 (16), 2971-2974.

Preparation 2

(5-Cyclopropyl-3-(2,6-dichloro-phenyl-isoxazol-4-yl)-methanol

Step 1

2,6-Dichloro-benzaldehyde oxime 2,6-Dichloro-benzaldehyde (7.0 g, 40 mmol) is added to 10 mL of water and 30 mL of methanol. Sodium hydroxide (4.0 g, 100 mmol) is dissolved in 8 mL of water slowly. The sodium hydroxide solution is added to the benzaldehyde solution. The reaction is stirred overnight. The reaction mixture is partitioned between ethyl acetate and water. The organic layer is washed with brine and dried over solid sodium sulfate. The organic layer is filtered and the solvent is removed under reduced pressure to yield the title compound.

Step 2

2,6 Dichloro-benzaldehyde chloroxime

To a solution of 2,6-dichloro-benzaldehyde (7.6 g, 40 mmol) in DMF (56 mL) is added N-chlorosuccinimide (5.9 g, 44.0 mmol) followed by a catalytic amount of HCl gas. The reaction mixture is stirred overnight. The reaction mixture is partitioned between ether and water. The layers are separated and the ether layer is washed with brine and dried over sodium sulfate. The ether layer is filtered and the solvent is removed under reduced pressure to yield the crude product. The crude product is chromatographed using a gradient of 10% ethyl acetate in hexanes to 15% ethyl acetate in hexanes to yield the title compound. $^1$H-NMR (400 MHz, CDCl$_3$) δ 8.76 (b, 1H), 7.38-7.26 (m, 3H).

Step 3

5-Cyclopropyl-3-(2,6-dichloro-phenyl)-isoxazole-4-carboxylic acid methyl ester

3-Cyclopropyl-3-oxo-propionic acid methyl ester (0.55 g, 3.9 mmol) is combined with triethylamine (0.393 g, 3.9 mmol) and is stirred for five minutes. 2,5 Dichlorobenzaldehyde-chloro-oxime (0.88 g, 3.9 mmol) is added and the reaction is stirred overnight. The solvent is removed under reduced pressure and the residue is purified via flash chromatography using a gradient of 1% ethyl acetate in hexanes to 10% ethyl acetate in hexanes to yield the title compound (0.80 g, 66%). $^1$H-NMR (400 MHz, CDCl$_3$) δ 7.37 (d, 2H), 7.31 (t, 1H), 3.66 (s, 3H), 2.88 (m, 1H), 1.38 (m, 2H), 1.25 (m, 2H).

Step 4

(5-Cyclopropyl-3-(2,6-dichloro-phenyl)-isoxazol-4-yl)-methanol

To a 0° C. solution of 5-cyclopropyl-3-(2,6-dichloro-phenyl)-isoxazole-4-carboxylic acid methyl ester (0.80 g, 2.6 mmol) in THF (8 mL) is added a 1M DIBAL solution in toluene (5.66 mL). The reaction is stirred one hour. An additional 1M DIBAL solution in Toluene (5.66 mL) is added and the reaction is stirred for an additional hour. The reaction is quenched with methanol and is acidified with aqueous HCl solution (1M). The aqueous solution is extracted with ethyl acetate. The organic layer is washed with brine, dried over sodium sulfate, and filtered. The solvent is removed under reduced pressure to yield the title compound (0.68 g, 93%). ES/MS m/e 284.0 (M+1).

The following list of compounds is prepared essentially as described in the synthesis of (5-cyclopropyl-3-(2,6-dichloro-phenyl)-isoxazol-4-yl)-methanol.

Preparation 2A: [5-Cyclopropyl-3-(2-trifluoromethoxy-phenyl)-isoxazol-4yl]-methanol (0.2 g, 99%), utilizing 2-trifluoromethoxy-benzaldehyde, $^1$H NMR (400M Hz, CDCl$_3$) δ 7.56-7.49 (2H), 7.38 (t, 2H), 4.60 (s, 2H), 2.15 (m, 1H), 1.23 (m, 2H), 1.14 (m, 2H);

Preparation 2B: [5-Cyclopropyl-3-(2-fluoro-6-trifluoromethyl-phenyl)-isoxazol-4-yl]-methanol, utilizing 2-fluoro-6-trifluoromethyl-benzaldehyde, $^1$H NMR (400M Hz, CDCl$_3$) δ 7.67-7.55 (m, 2H), 7.37 (m, 1H), 4.34 (s, 2H), 2.13 (m, 1H), 1.22 (m, 2H), 1.10 (m, 2H);

Preparation 2C: [5-Isopropyl-3-(2-isopropyl-phenyl)-isoxazol-4-yl]-methanol utilizing 2-isopropyl-benzaldehyde, ES/MS m/e 260.0 (M+1), 258.0 (M−1).

Preparation 3

4-Bromomethyl-3-(2,6-dichloro-phenyl)-5-isopropyl-isoxazole

To a solution of [3-(2,6-dichloro-phenyl)-5-isopropyl-isoxazol-4-yl]-methanol (1.14 g, 4 mmol) in THF (20 mL) is added PBr$_3$ (0.76 mL, 8 mmol). The reaction mixture is stirred at reflux for 30 minutes. The reaction mixture is diluted with EtOAc and is washed with 0.2 N HCl. The organic layer is separated, dried (MgSO$_4$), filtered, and concentrated to give the title compound as an oil.

Preparation 4

4-Bromomethyl-5-cyclo-propyl-3-(2-fluoro-6-trifluoromethyl-phenyl)-isoxazole

A solution of 5-cyclopropyl-3-(2-fluoro-6-trifluoromethyl-phenyl)-isoxazol-4-yl)-methanol (0.203 g, 0.674 mmol) and phosphorous tribromide (0.094 g, 1.35 mmol) in dichloromethane (2 mL) is stirred for 40 minutes. The reaction mixture is partitioned between water and dichloromethane. The layers are separated and the organic layer is dried over sodium sulfate and filtered. The solvent is removed under reduced pressure to yield the title compound.

Preparation 5

4-Bromomethyl-3-cyclopropyl-3-(2,6-dichloro-phenyl)-isoxazole

To a 0° C. solution of (5-cyclopropyl-3-(2,6-dichloro-phenyl)-isoxazol-4-yl)-methanol (0.124 g, 0.44 mmol) in dichloromethane (4 mL) is added phosphorous tribromide (0.261 g, 0.963 mmol). The ice bath is removed after 20 minutes and the reaction is allowed to stir for an additional twenty minutes at room temperature. The reaction mixture is quenched with pH 7 buffer and extracted with dichloromethane several times. The organic layers are combined, washed with brine, dried over sodium sulfate, filtered, and concentrated under reduced pressure to yield the title compound (0.124 g, 82%). $^1$H-NMR (400 MHz CDCl$_3$) δ 7.45-7.33 (m, 3H), 4.20 (s, 2H), 2.09 (m, 1H), 1.27 (m, 2H), 1.16 (m, 2H).

Preparation 6

5-(4-Hydroxy-2-methyl-phenyl)-4-methyl-thiophene-2-carboxylic acid methyl ester

Step 1

To a mixture of 4-methoxy-2-methylphenylboronic acid (912 mg, 6 mmol), 5-bromo-4-methyl-thiophene-2-carboxylic acid methyl ester (1.1 g, 5 mmol) and K$_2$CO$_3$ (1.38 g, 10 mmol) in toluene (30 mL) and water (5 mL) is bubbled N$_2$ for 15 minutes followed by addition of tetrakis(triphenylphosphine)palladium (289 mg, 0.25 mmol). The mixture is stirred at 80° C. under N$_2$ overnight and filtered through a pad of diatomaceous earth eluting with EtOAc. The combined filtrate is concentrated. The resulting residue is purified by column chromatography (0-15% EtOAc in hexanes) to give 5-(4-methoxy-2-methyl-phenyl)-4-methyl-thiophene-2-carboxylic acid methyl ester (540 mg, 39%). $^1$H-NMR (CDCl$_3$): δ 7.63 (s, 1H), 7.15 (d, 1H, J=8.4 Hz), 6.82 (d, 1H, J=2.8 Hz), 6.78 (dd, 1H, J=2.8, J=8.4 Hz), 4.79 (bs, 1H), 3.88 (s, 3H), 3.83 (s, 3H), 2.17 (s, 3H), 2.02 (s, 3H).

Step 2

To a solution of 5-(4-methoxy-2-methyl-phenyl)-4-methyl-thiophene-2-carboxylic acid methyl ester (540 mg, 2 mmol) in dichloromethane (30 mL) at 0° C. is added BBr$_3$ in dichloromethane (1N, 5.0 mL). The mixture is stirred at ambient temperature overnight. The reaction is quenched by addition of methanol and is evaporated. The residue is purified by column chromatography (0-20% EtOAc in hexanes) to give 5-(4-hydroxy-2-methyl-phenyl)-4-methyl-thiophene-2-carboxylic acid methyl ester (420 mg, 82%). $^1$H NMR (CDCl$_3$): δ 7.62 (s, 1H), 7.10 (d, 1H, J=7.9 Hz), 6.76 (s, 1H), 6.70 (d, 1H, J=7.9 Hz), 4.79 (bs, 1H), 3.88 (s, 3H), 2.15 (s, 3H), 2.02 (s, 3H).

The following list of compounds is prepared essentially according to the preparation of 5-(4-hydroxy-2-methyl-phenyl)-4-methyl-thiophene-2-carboxylic acid methyl ester.

Preparation 6A: 5-(4-Hydroxy-phenyl-thiophene-2-carboxylic acid methyl ester, utilizing 5-bromo-thiophene-2-carboxylic acid methyl ester and 4-methoxyphenylboronic acid, $^1$H NMR (DMSO-d$_6$): δ 9.87 (s, 1H), 7.74 (d, 1H, J=4.0 Hz), 7.57 (d, 2H, J=8.8 Hz), 7.40 (d, 1H, J=4.0 Hz), 6.83 (d, 2H, J=8.8 Hz), 3.81 (s, 3H).

Preparation 6B: 5-(4-Hydroxy-2-methyl-phenyl)-thiophene-2-carboxylic acid methyl ester, utilizing 5-bromo-thiophene-2-carboxylic acid methyl ester and 4-methoxy-2-methylphenylboronic acid, $^1$H NMR (DMSO-d$_6$): δ 9.71 (s, 1H), 7.76 (d, 1H, J=3.5 Hz), 7.26 (d, 1H, J=8.4 Hz), 7.17 (d, 1H, J=4.0 Hz), 6.72 (d, 1H, J=2.6 Hz), 6.67 (dd, 1H, J=2.6, J=8.4 Hz), 3.81 (s, 3H), 2.32 (s, 3H).

Preparation 6C: 5-(2-Chloro-4-hydroxy-phenyl)-thiophene-2-carboxylic acid methyl ester, utilizing 4-bromo-3-chloro-phenol and 5-methoxycarbonyl-thiophene-2-boronic acid, $^1$H NMR (DMSO-d$_6$): δ 10.33 (s, 1H), 7.78 (d, 1H, J=3.8 Hz), 7.53 (d, 1H, J=8.6 Hz), 7.37 (d, 1H, J=3.8 Hz), 6.96 (s, 1H), 6.84 (d, 1H, J=8.6 Hz), 3.82 (s, 3H).

Preparation 6D: 5-(2-Chloro-4-hydroxy-phenyl)-4-methyl-thiophene-2-carboxylic acid methyl ester, utilizing 5-bromo-4-methyl-thiophene-2-carboxylic acid methyl ester and 4-methoxy-2-chloro-phenyl boronic acid, $^1$H NMR (DMSO-d$_6$): δ 10.26 (bs, 1H), 7.68 (s, 1H), 7.25 (d, 1H, J=8.4 Hz), 6.96 (d, 1H, J=2.6 Hz), 6.83 (dd, 1H, J=2.6, 8.4 Hz), 3.82 (s, 3H), 2.03 (s, 3H).

Preparation 6E: 2-(4-Hydroxy-2-methyl-phenyl)-4-methyl-thiazole-5-carboxylic acid methyl ester, utilizing 2-bromo-4-methyl-thiazole-5-carboxylic acid methyl ester and 4-methoxy-2-methylphenyl boronic acid, $^1$H NMR (DMSO-d$_6$): δ 10.0 (s, 1H), 7.74 (d, 1H, J=8.4 Hz), 6.74 (s, 1H), 6.73 (d, 1H, J=8.4 Hz), 3.81 (s, 3H), 2.67 (s, 1H), 2.50 (s, 3H).

Preparation 6F: 2-(4-Hydroxy-2-methyl-phenyl)-thiazole-5-carboxylic acid ethyl ester, utilizing 2-bromo-thiazole-5-carboxylic acid ethyl ester and 4-methoxy-2-methylphenyl boronic acid, $^1$H NMR (DMSO-d$_6$): δ 8.44 (s, 1H), 7.74 (d, 1H, J=8.4 Hz), 6.76 (s, 1H), 6.75 (d, 1H, J=8.4 Hz), 4.33 (q, 2H), 2.51 (s, 3H), 1.30 (t, 3H).

Preparation 6G: 6-(4-Hydroxy-2-methyl-phenyl)-nicotinic acid methyl ester, utilizing 6-chloro-nicotinic acid methyl ester and 4-methoxy-2-methylphenyl boronic acid, $^1$H NMR (DMSO-d$_6$): δ 9.65 (s, 1H), 9.10 (s, 1H), 8.27 (dd, 1H, J=2.2, J=8.4 Hz), 7.62 (dd, 1H, J=0.9, J=8.4 Hz), 7.32 (d, 1H, J=8.8 Hz), 6.71 (s, 1H), 6.69 (t, 1H), 3.89 (s, 3H), 2.31 (s, 3H).

Preparation 7

2-(4-Hydroxy-phenyl-4-methyl-thiazole-5-carboxylic acid ethyl ester

Step A

A mixture of 4-methoxy-thiobenzamide (5 g, 30 mmol) and 2-chloro-3-oxo-butyric acid ethyl ester (4.6 mL, 33 mmol) in ethanol is stirred under reflux overnight. The reaction is concentrated and the residue is triturated with ether to give 2-(4-methoxy-phenyl)-4-methyl-thiazole-5-carboxylic acid ethyl ester as a yellow solid (5.8 g, 70%).

LC-ES/MS m/e 278 (M+1).

Step B

To a −80° C. solution of 2-(4-methoxy-phenyl)-4-methyl-thiazole-5-carboxylic acid ethyl ester (550 mg, 2 mmol) in dichloromethane (20 mL) is added $BBr_3$ (5 mL, 1M solution in dichloromethane). The reaction is stirred at ambient temperature overnight. The reaction is quenched by addition of methanol and is concentrated in vacuo. The residue is partitioned between EtOAc and 1N HCl. The organic layer is concentrated and the residue is purified by chromatography (0 to 30% EtOAc in hexanes) to give the title compound as a tan solid, (500 mg, 95%). LC-ES/MS m/e 264 (M+1), $^1$H NMR (DMSO-d6) δ 10.22 (s, 1H), 7.82 (d, 2H), 6.86 (d, 2H), 4.27 (q, 2H), 2.64 (s, 3H), 1.29 (t, 3H).

Preparation 8

3-Methyl-4-(4,4,5,5-tetramethyl-[1,3,2]dioxaborolan-2-yl)-phenol

A mixture of tricyclohexylphosphine (525 mg, 1.87 mmol), palladium bis(dibenzylidine) acetone (460 mg, 0.801 mmol) and dioxane (200 mL) is stirred at room temperature for one half hour. To the reaction mixture is added 4-bromo-3-methyl-phenol (5.00 g, 26.7 mmol), pinacolborane (7.45 g, 40.1 mmol) and potassium acetate (3.93 g, 40.1 mmol). The reaction mixture is heated to 80° C. for 20 hours. The reaction mixture is cooled and diluted with water. The resulting aqueous mixture is extracted with ether several times. The combined ether fractions are washed with brine, dried ($MgSO_4$), and concentrated under reduced pressure. The residue is purified via flash chromatography (gradient: 0 to 2% MeOH/$CH_2Cl_2$) to yield the title compound (1.6 g, 47%). A second purification of impure fractions is performed to provide an additional 2.76 g of the title compound for a total of 4.36 g (70%). ES/MS m/e 233.3 (M−1).

Preparation 9

(5-Bromo-1H-indol-3-yl)-acetic acid methyl ester

To a solution of (5-bromo-1H-indol-3-yl)-acetic acid (683 mg, 2.69 mmol) in methanol (6 mL) is added (trimethylsilyl)diazomethane (2.0 M solution in hexanes, approximately 6 mL) over two minutes at room temperature. The yellow mixture is concentrated. The residue is taken up in methanol and is concentrated several times to give of the title compound (710 mg, 99%). ES/MS m/e 266.2 (M−2).

The following list of compounds is prepared essentially as described in the preparation of (5-bromo-1H-indol-3-yl)-acetic acid methyl ester.
Preparation 9A: 6-Bromo-1H-indole-3-carboxylic acid methyl ester, utilizing 6-bromoindole-3-carboxylic acid, ES/MS m/e 256.0 (M+2);
Preparation 9B: 5-Bromo-1H-indole-3-carboxylic acid methyl ester, utilizing 5-bromo-1H-indole-3-carboxylic acid;
Preparation 9C: 6-Bromo-1H-indole-2-carboxylic acid methyl ester, utilizing 6-bromo-1H-indole-2-carboxylic acid, ES/MS m/e 270.0 (M+2);
Preparation 9D: 5-Bromo-benzo[b]thiophene-3-carboxylic acid methyl ester, utilizing 5-bromo-benzo[b]thiophene-3-carboxylic acid, $^1$H NMR (400 MHz, $CDCl_3$) δ 8.73 (s, 1H), 8.36 (s, 1H), 7.70 (d, 1H), 7.49 (d, 1H), 3.93 (s, 3H);
Preparation 9E: 6-Bromo-benzo[b]thiophene-2-carboxylic acid methyl ester, utilizing 6-bromo-benzo[b]thiophene-2-carboxylic acid, $^1$H NMR (400 MHz, $CDCl_3$) δ 7.99 (m, 2H), 7.70 (d, 1H), 7.50 (d, 1H), 3.92 (s, 3H).

Preparation 10

6-Bromo-1-methyl-1H-indole-3-carboxylic acid methyl ester

A mixture of 5-bromo-1H-indole-3-carboxylic acid methyl ester (200 mg, 0.787 mmol), potassium carbonate (100 mg, 0.394 mmol) and DMF (1 mL) is stirred at room temperature and iodomethane (30 μL, 0.47 mmol) is added. After 1.5 hours, additional iodomethane (10 μL) is added and the reaction is stirred for 30 minutes and diluted with dichloromethane and filtered. The filtrate is concentrated under high vacuum, diluted with ethyl acetate, filtered and concentrated under reduced pressure to give the title compound (1105 mg, 99%). ES/MS m/e 270.0 (M+2).

The following list of compounds is prepared essentially according to the preparation of 6-bromo-1-methyl-1H-indole-3-carboxylic acid methyl ester.
Preparation 10A: 6-Bromo-1-methyl-1H-indole-2-carboxylic acid methyl ester, utilizing 6-bromo-1H-indole-2-carboxylic acid methyl ester, ES/MS m/e 270.0 (M+2);
Preparation 10B: 6-Bromo-1-isopropyl-1H-indole-3-carboxylic acid methyl ester, utilizing 6-bromo-1H-indole-3-carboxylic acid methyl ester and isopropyl bromide, the title compound is prepared. $^1$H NMR (400 MHz, $CDCl_3$) δ 8.02 (d, 1H), 7.88 (s, 1H), 7.52 (s, 1H), 7.33 (d, 1H), 4.60 (m, 1H), 3.88 (s, 3H), 1.55 (d, 6H);
Preparation 10C: 6-Chloro-1,2-dimethyl-1H-indole-3-carboxylic acid methyl ester, utilizing 6-chloro-2-methyl-1H-indole-3-carboxylic acid methyl ester. ES/MS m/e 238.0 (M+1).

Preparation 11

6-Bromo-1-(2-methoxy-ethyl)-1H-indole-3-carboxylic acid methyl ester

Sodium hydride (60% in mineral oil, 87 mg, 2.2 mmol) is added to a solution of 6-bromo-1H-indole-3-carboxylic acid methyl ester (500 mg, 1.97 mmol) in DMF (5 mL) at room temperature and the mixture is stirred for 30 minutes. To the reaction mixture is added 1-bromo-2-methoxy-ethane (222 μL, 2.36 mmol). After one hour, sodium hydride (20 mg) is added. Thirty minutes later, 1-bromo-2-methoxy-ethane (60 μL) is added. The mixture is heated to 60° C. for one hour. The cooled mixture is quenched with a small amount of water and concentrated under reduced pressure. The residue is taken up in ethyl acetate and filtered. The filtrate is concentrated under reduced pressure and the resulting residue is purified by column chromatography (gradient: 10 to 60% ethyl acetate/heptane) followed by purification via radial chromatography (gradient: 0 to 1% MeOH/$CH_2Cl_2$) to provide the title compound (386 mg, 63%). ES/MS m/e 314.0 (M+2).

The following list of compounds is prepared essentially according to the preparation of 6-bromo-1-(2-methoxy-ethyl)-1H-indole-3-carboxylic acid methyl ester.
Preparation 11A: 6-Bromo-1-butyl-1H-indole-3-carboxylic acid methyl ester,
utilizing 6-bromo-1H-indole-3-carboxylic acid methyl ester and 1-bromobutane, ES/MS m/e 311.9 (M+1);

Preparation 11B: 6-Bromo-1-(2-methylsulfanyl-ethyl)-1H-indole-3-carboxylic acid methyl ester, utilizing 6-bromo-1H-indole-3-carboxylic acid methyl ester and 1-chloro-2-methylsulfanyl-ethane, ES/MS m/e 329.9 (M+1).

Preparation 12

6-Bromo-1-methyl-1H-indole-3-carboxylic acid methyl ester

To a room temperature mixture of 5-bromo-1H-indole-3-carboxylic acid methyl ester (100 mg, 0.394 mmol), potassium carbonate (163 mg, 1.18 mmol) and DMF is added iodomethane (30 µL, 0.47 mmol). After 1.5 hours, additional iodomethane (10 µL) is added and the reaction is stirred for 30 minutes. The reaction mixture is diluted with dichloromethane and filtered. The filtrate is concentrated under high vacuum, diluted with ethyl acetate, and concentrated to give the title compound (105 mg, 99%). ES/MS m/e 270.0 (M+2).

Preparation 13

6-Bromo-1-methyl-1H-indole-2-carboxylic acid methyl ester

The title compound is prepared essentially as described in the preparation of 6-bromo-1-methyl-1H-indole-3-carboxylic acid methyl ester utilizing 6-bromo-1H-indole-2-carboxylic acid methyl ester, ES/MS m/e 270.0 (M+2).

Preparation 14

6-Bromo-1-(2-dimethylamino-ethyl)-1H-indole-3-carboxylic acid methyl ester

A mixture of 6-bromo-1H-indole-3-carboxylic acid methyl ester (500 mg, 1.97 mmol), sodium hydride (60% in mineral oil, 748 mg, 31.2 mmol), sodium iodide (295 mg, 1.96 mmol), 2-dimethylaminoethyl chloride hydrochloride (341 mg, 2.37 mmol) and DMF (60 mL) is heated at 100° C. for 8 hours. The reaction mixture is cooled, filtered, and the solids are washed with water and air dried. The solids are dissolved in MeOH (200 mL) and (trimethylsilyl)diazomethane (2.0 M solution in hexanes, 20 mL) is added over several minutes. The reaction mixture is stirred for one hour and concentrated under reduced pressure. The residue is partitioned between water and ethyl acetate. The ethyl acetate layer is separated and dried over MgSO$_4$. The crude product is purified via radial chromatography using 2.5% MeOH/CH$_2$Cl$_2$ to afford the title compound (195 mg, 30%). ES/MS m/e 327.0 (M+2).

Preparation 15

[5-(4-Hydroxy-2-methyl-phenyl)-1H-indol-3-yl]-acetic acid methyl ester

A mixture of 3-methyl-4-(4,4,5,5-tetramethyl-[1,3,2]dioxaborolan-2-yl)-phenol (287 mg, 1.22 mmol), (5-bromo-1H-indol-3-yl)-acetic acid methyl ester (273 mg, 1.02 mmol), tetrakis(triphenylphosphine)palladium(0) (57 mg, 0.046 mmol), DMF (2.7 mL), ethanol (1.34 mL) and 2M aqueous potassium carbonate (1.34 mL) is heated to 100° C. for 16 hours. The reaction is cooled to room temperature and diluted with water and acidified with 1 N HCl. The resulting solution is extracted with ethyl acetate. The combined organic layers are dried over anhydrous magnesium sulfate and concentrated. The residue is dissolved in methanol (6 mL) and trimethylsilyldiazomethane (2.0 M solution in hexanes, approximately 4 mL) is added over approximately two minutes at room temperature. The yellow mixture is concentrated and the residue is purified via radial chromatography eluting with a gradient of 20 to 50% ethyl acetate/heptane and crystallized from CH$_2$Cl$_2$/heptane to give the title compound (180 mg, 60%). ES/MS m/e 296.1 (M+1).

The following list of compounds is prepared essentially as described in the preparation of [5-(4-hydroxy-2-methyl-phenyl)-1H-indol-3-yl]-acetic acid methyl ester.

Preparation 15A: 6-(4-Hydroxy-2-methyl-phenyl)-1H-indole-3-carboxylic acid methyl ester, utilizing 6-bromo-1H0indole-3-carboxylic acid methyl ester, (134 mg, 63%);

Preparation 15B: 5-(4-Hydroxy-2-methyl-phenyl)-1H-indole-3-carboxylic acid methyl ester, utilizing 5-bromo-1H-indole-2-carboxylic acid methyl ester, ES/MS m/e 296.1 (M+1);

Preparation 15C: 6-(4-Hydroxy-2-methyl-phenyl)-1H-indole-2-carboxylic acid methyl ester, utilizing 6-bromo-1H-indole-2-carboxylic acid methyl ester, ES/MS m/e 296.1 (M+1);

Preparation 15D: 6-(4-Hydroxy-2-methyl-phenyl)-1H-indole-3-carboxylic acid methyl ester, utilizing 6-bromo-1H-indole-3-carboxylic acid methyl ester, ES/MS m/e 282.1 (M+1);

Preparation 15E: 6-(4-Hydroxy-2-methyl-phenyl)-1-methyl-1H-indole-3-carboxylic acid methyl ester, utilizing 6-bromo-1-methyl-1H-indole-3-carboxylic acid methyl ester, LC-ES/MS m/e 296.0 (M+1);

Preparation 15F: 6-(4-Hydroxy-2-methyl-phenyl)-1-methyl-1H-indole-2-carboxylic acid methyl ester, utilizing 6-bromo-1-methyl-1H-indole-2-carboxylic acid methyl ester and 3-methyl-4-(4,4,5,5-tetramethyl-[1,3,2]dioxaborolan-2-yl)-phenol, ES/MS m/e 296.1 (M+1);

Preparation 15G: 5-(4-Hydroxy-2-methyl-phenyl)-benzo[b]thiophene-3-carboxylic acid methyl ester, utilizing 5-bromo-benzo[b]thiophene-3-carboxylic acid methyl ester, ES/MS nm/e 299.1 (M+1);

Preparation 15H: 6-(4-Hydroxy-2-methyl-phenyl)-benzo[b]thiophene-2-carboxylic acid methyl ester, utilizing 6-bromo-benzo[b]thiophene-2-carboxylic acid methyl ester, ES/MS m/e 297.3 (M−1);

Preparation 15I: 6-(4-Hydroxy-2-methyl-phenyl)-1-(2-methoxy-ethyl)-1H-indole-3-carboxylic; acid methyl ester, utilizing 6-bromo-1-(2-methoxy-ethyl)-1H-indole-3-carboxylic acid methyl ester, ES/MS m/e 340.1 (M+1);

Preparation 15J: 1-Butyl-6-(4-hydroxy-2-methyl-phenyl)-1H-indole-3-carboxylic acid methyl ester utilizing 6-bromo-1-butyl-1H-indole-3-carboxylic acid methyl ester, MS m/e 338.1 (M+1);

Preparation 15K: 6-(4-Hydroxy-2-methyl-phenyl)-1-isopropyl-1H-indole-3-carboxylic acid methyl ester, utilizing 6-bromo-1-isopropyl-1H-indole-3-carboxylic acid methyl ester, ES/MS m/e 324.1 (M+1);

Preparation 15L: 6-(4-Hydroxy-2-methyl-phenyl)-1-(2-methylsulfanyl-ethyl)-1H-indole-3-carboxylic acid methyl ester, utilizing 6-bromo-1-(2-methylsulfanyl-ethyl)-1H-indole-3-carboxylic acid methyl ester, ES/MS m/e 354.2 (M−1);

Preparation 15M: 1-(2-Dimethylamino-ethyl)-6-(4-hydroxy-2-methyl-phenyl)-1H-indole-3-carboxylic acid methyl ester, utilizing 6-bromo-1-(2-dimethylamino-ethyl)-1H-indole-3-carboxylic acid methyl ester, ES/MS m/e 353.1 (M+1);

Preparation 15N: 6-(4-Hydroxy-2-methyl-phenyl)-benzo[b]thiophene-3-carboxylic acid methyl ester; compound with 6-(4-hydroxy-2-methyl-phenyl)-benzo[b]thiophene-2-carboxylic acid methyl ester, utilizing a 7:3 mixture of 6-bromo-benzo[b]thiophene-3-carboxylic acid methyl ester and 6-bromo-benzo[b]thiophene-2-carboxylic acid methyl ester, MS m/z: 297.0 (M−1).

Preparation 16

2-(4-Hydroxy-2-methyl-phenyl)-4-isopropyl-thiazole-5-carboxylic acid ethyl ester Step 1

2-Amino-4-isopropyl-thiazole-5-carboxylic acid ethyl ester

To a solution of 4-methyl-3-oxo-pentanoic acid ethyl ester (10 g, 63.2 mmol) in dichloromethane (150 mL) at 0° C. is added $SO_2Cl_2$ (5.64 mL, 69.5 mmol). The reaction mixture is stirred at ambient temperature for 1 hour. The reaction mixture is extracted with water (30 mL). To the aqueous layer is added 1,4-dioxane (60 mL) followed by thiourea (8.8 g, 63.2 mmol). The mixture is stirred at 80° C. overnight and cooled to room temperature. The reaction mixture is adjusted to pH 12 with conc. $NH_4OH$ and filtered. The filter cake is washed with water to give the title compound (12.4 g, 92%).

$^1$H NMR (DMSO-$d_6$) δ 7.72 (s, 2H), 4.14 (q, 2H), 3.76 (m, 1H), 1.21 (t, 3H), 1.11 (d, 6H).

Step 2

2-Bromo-4-isopropyl-thiazole-5-carboxylic acid ethyl ester

To a solution of 2-amino-4-isopropyl-thiazole-5-carboxylic acid ethyl ester (4.28 g, 20 mmol) in $CH_3CN$ (30 mL) is added iso-amylnitrite (4.3 mL, 32 mmol) followed by copper bromide (8.9 g, 40 mmol). The reaction mixture is stirred at 80° C. for 3 hours and concentrated under reduced pressure. The residue is partitioned between EtOAc and water. The organic phase is filtered through a Celite® pad and the filtrate is concentrated under reduced pressure. The residue is purified by column chromatography (gradient: 0 to 10% EtOAc in hexanes) to give the title product (5 g, 90%). $^1$H NMR (CDCl$_3$) δ 4.33 (q, 2H), 3.95 (m, 1H), 1.36 (t, 3H), 1.28 (d, 6H).

Step 3

2-(4-Hydroxy-2-methyl-phenyl)-4-isopropyl-thiazole-5-carboxylic acid ethyl ester To a solution of 2-bromo-4-isopropyl-thiazole-5-carboxylic acid ethyl ester (834 mg, 3 mmol), 3-methyl-4-(4,4,5,5-tetramethyl-[1,3,2]dioxaborolan-2-yl)-phenol (1.4 g, 6 mmol) and $K_2CO_3$ (828 mg, 6 mmol) in 1,4-dioxane/$H_2O$ (30 mL/5 mL) is bubbled nitrogen gas for 10 minutes. To this solution is added tetrakistriphenylphosphine palladium (173 mg, 0.15 mmol). The reaction mixture is stirred at 100° C. overnight. The reaction mixture is concentrated under reduced pressure and the residue is partitioned between EtOAc and 1N HCl. The organic phase is concentrated and purified by column chromatography (gradient: 0 to 15% EtOAc in hexanes) to give the title product (730 mg, 80%). $^1$H NMR (DMSO-$d_6$) δ 9.99 (s, 1H), 7.68 (d, 1H), 6.68, 6.72 (m, 2H), 4.26 (q, 2H), 3.88 (m, 1H), 2.50 (s, 3H), 1.26 (t, 3H), 1.23 (d, 6H).

The following list of compounds is prepared essentially as described in the preparation of 2-(4-hydroxy-2-methyl-phenyl)-4-isopropyl-thiazole-5-carboxylic acid ethyl ester.

Preparation 16A: 2-(4-Hydroxy-2-methyl-phenyl)-4-propyl-thiazole-5-carboxylic acid ethyl ester, utilizing 2-amino-4-propyl-thiazole-5-carboxylic acid ethyl ester, $^1$H NMR (DMSO-$d_6$) δ 10.00 (s, 1H), 7.72 (d, 1H), 6.71, 6.75 (m, 2H), 4.28 (q, 2H), 3.06 (t, 2H), 2.50 (s, 3H), 1.72 (m, 2H), 1.28 (t, 3H), 0.92 (t, 3H);

Preparation 16B: 2-(4-Hydroxy-2-methyl-phenyl)-4-trifluoromethyl-thiazole-5-carboxylic acid ethyl ester, utilizing 2-amino-4-trifluoromethyl-thiazole-5-carboxylic acid ethyl ester, LC-ES/MS m/e 332 (M+1), 330 (M−1), 91.2%;

Preparation 16C: 2-(4-Hydroxy-2-methyl-phenyl)-4-phenyl-thiazole-5-carboxylic acid ethyl ester, utilizing 2-amino-4-phenyl-thiazole-5-carboxylic acid ethyl ester, $^1$H NMR (DMSO-$d_6$) δ 10.06 (s, 1H), 7.76, 7.79 (m, 3H), 7.44, 7.46 (m, 3H), 6.74, 6.77 (m, 2H), 4.23 (q, 2H), 2.56 (s, 3H), 1.21 (t, 3H);

Preparation 16D: 2-(4-Hydroxy-2-methyl-phenyl)-thiazole-4-carboxylic acid ethyl ester, utilizing 2-bromo-thiazole-4-carboxylic acid ethyl ester, LC-ES/MS m/e 264 (M+1), 262 (M−1), 100%;

Preparation 16E: 2-(4-Hydroxy-2-methyl-phenyl)-5-isopropyl-thiazole-4-carboxylic acid ethyl ester utilizing 2-amino-5-isopropyl-thiazole-4-carboxylic acid ethyl ester, LC-ES/MS m/e 292 (M+1), 290 (M−1), 95.6%.

Preparation 17

4-Bromo-benzo[b]thiophene

Step 1

2-bromo-6-fluoro-benzaldehyde

A solution of n-butyllithium (2.5M in hexanes, 2.866 L, 7.17 mol) is added dropwise to a stirred solution of diisopropylamine (745.7 g, 7.37 mol) in tetrahydrofuran (1.630 L) such that the temperature is maintained in the range −60 to −78° C. The resulting suspension is stirred for 1.5 h at −75 to −78° C. A solution of 1-bromo-3-fluorobenzene (1.228 Kg, 7.02 mol) in tetrahydrofuran (2.40 L) is added slowly to the reaction mixture over 1.5 h. Stirring is continued for 30 min at −70 to −71° C. Dimethylformamide (511.3 g) is added over 1 h. The reaction mixture is allowed to warm to −15° C. and is quenched by the slow addition of acetic acid (1.965 L) over 20 min. TBME (5.20 L) and water (6.25 L) are added. The resultant solution is stirred vigorously and the layers are separated. The aqueous layer is extracted with TBME (1.965 L) twice and the combined organic layers are washed with 0.2 M hydrochloric acid (2×5.00 L), saturated aqueous sodium hydrogen carbonate solution (2×2.50 L) and water (3.50 L). The organic layer is dried over magnesium sulfate, filtered and concentrated under reduced pressure to afford the title compound as a yellow crystalline solid (1.367 Kg, 96%). $^1$H NMR (CDCl$_3$): δ 10.36 (s, 1H), 7.49 (d, 1H, 3=7.8 Hz), 7.45-7.37 (m, 1H), 7.15 (t, 1H, J=7.9 Hz).

Step 2

4-bromo-benzo[b]thiophene-2-carboxylic acid

Potassium hydroxide (415.1 g, 7.40 mol) is added to a stirred solution of 2-bromo-6-fluorobenzaldehyde (1.00 Kg, 4.93 mol) and mercaptoacetic acid (453.8 g, 4.93 mol) in dimethylformamide (5.0 L). The resultant solution is brought to and maintained at reflux (136° C.) for 90 min. The reaction mixture is allowed to cool to room temperature and is quenched by the slow addition of hydrochloric acid (2.25 M, 5.90 L) over 5 min. The mixture is cooled to 10° C., stirred for 1 h and the observed solid material is collected by filtration. The filter cake is washed with water (1.00 L) and hexanes (2.00 L) and dried in vacuo at 40 to 45° C. to constant weight to yield the title compound (990.0 g, 78.2%). $^1$H NMR (DMSO, $d_6$): δ 13.8 (bs, 1H), 8.10 (d, 1H, J=8.2 Hz), 7.97 (s, 1H), 7.72 (d, 1H, J=7.6 Hz), 7.45 (t, 1H, J=8.0 Hz).

Step 3

4-Bromo-benzo[b]thiophene

Copper powder (49.8 g) is added to a stirred mixture of 4-bromo-benzo[b]thiophene-2-carboxylic acid (995.5 g, 3.87 mol) and quinoline (1.99 L) and the resultant mixture is heated to and maintained at 15 to 195° C. for 5 h. The mixture is allowed to cool to room temperature and the reaction is quenched by the addition of a mixture of ice (5.81 Kg) and concentrated hydrochloric acid (2.48 L). TBME (9 L) is added and the mixture is stirred vigorously for 10 min and filtered. The clarified layers are separated and the aqueous layer is extracted with TBME (1.0 L). The combined extracts are washed with hydrochloric acid (1 M, 2×5.00 L) and water (4.0 L), dried over magnesium sulfate, filtered, and concentrated under reduced pressure to afford the crude product (640 g) as a brown oil which solidifies on standing overnight. The residue is slurried in methanol (500 mL, 0.5 vol) at −10 to 0° C. for 1.5 h, the observed solid material is collected by filtration and pulled dry on the filter. The methanolic mother liquors are concentrated by rotary evaporation. The residue is combined with the isolated solid material, slurried in TBME (2.0 L) and the collected solids are washed with TBME (660 L). The combined liquors and washes are washed with hydrochloric acid (1 M, 660 mL), saturated aqueous sodium hydrogen carbonate. (2×1.0 L) and water (4.0 L), dried over magnesium sulfate, filtered and concentrated by rotary evaporation at 40° C. to afford the crude product. The residue is slurried in methanol (1.10 L) at −10 to 0° C. for 1 h. The observed solid is collected by filtration and dried under vacuum at 20° C. to afford 4-bromo-benzo[b]thiophene as an off-white solid (315 g, 37%). $^1$H NMR (CDCl$_3$): δ 7.81 (d, 1H, J=8.0 Hz), 7.57-7.48 (m, 3H), 7.21 (t, 1H, J=7.7 Hz).

Preparation 18

Benzo[b]thiophene-4-carboxylic acid

The title compound (12.4 g, 85%) is prepared according to J. Heterocyclic Chem. 1967, 4(4), 651-2, utilizing 4-bromo-benzo[b]thiophene, $^1$H NMR (CDCl$_3$): δ 8.32-8.25 (m, 2H), 8.14 (d, 1H, J=8.0 Hz), 7.67 (d, 1H, J=5.75 Hz), 7.45 (t, 1H, J=8.0 Hz).

The following list of compounds is prepared essentially as described in the preparation of benzo[b]thiophene-4-carboxylic acid.

Preparation 18A: Benzo[b]thiophene-6-carboxylic acid (112.2 g, 67%), utilizing 6-bromo-benzo[b]thiophene;
Preparation 18B: Benzo[b]thiophene-7-carboxylic acid, (1.05 g, 63%), utilizing 7-Bromo-benzo[b]thiophene $^1$H NMR (CDCl$_3$): δ 8.26 (d, 1H, J=6.5 Hz), 8.10 (dd, 1H, J=7.3 Hz, 1 Hz), 7.61 (d, 1H, J=5.6 Hz), 7.51 (t, 1H, J=7.3 Hz), 7.44 (d, 1H, J=5.6 Hz).

Preparation 19

4-Carboxy-benzo[b]thiophen-2-boronic acid

A solution of n-BuLi (2.5M in hexane, 1.69 mol, 676 mL) is added slowly at −78° C. to a solution of diisopropylamine (1.69 mol, 236 mL) in 2 L of anhydrous THF. The mixture is stirred for 30 min. A solution of benzo[b]thiophene-4-carboxylic acid (0.8 mol, 143 g) in 2 L of anhydrous THF is added slowly and the mixture is allowed to reach 0° C. The reaction is cooled to −30° C. and the triisopropyl borate (2 mol, 463 mL) is added slowly. The cooling bath is removed and the mixture is allowed to reach room temperature. The reaction is quenched with 1.3 L of concentrated HCl and 1 L of water. The mixture is stirred overnight. The organic solvent is removed under reduced pressure. The precipitate is collected by filtration, washed with water, and dried under vacuum to yield the title compound (170.5 g, 96%). ES/MS m/e 221 (M−1).

Preparation 20

6-Carboxy-benzo[b]thiophen-2-boronic acid

The title compound (120 g, 86%) is prepared essentially as described in the preparation of 4-carboxy-benzo[b]thiophen-2-boronic acid utilizing benzo[b]thiophene-6-carboxylic acid, ES/MS m/e 221 M−1).

Preparation 21

4-(4-Bromo-3-methyl-phenoxymethyl)-3-(2,6-dichloro-phenyl)-5-isopropyl-isoxazole To a mixture of 3-(2,6-dichloro-phenyl)-5-isopropyl-isoxazole-4-carbinol (6.99 mmol; 2.0 g) and 4-bromo-3-methylphenol (8.38 mmol; 1.6 g) in toluene (100 mL) is added 1,1'-(azodicarbonyl)dipiperidine (10.48 mmol; 2.7 g) followed by tri-n-butylphosphine (10.48 mmols; 2.91 mL) and the mixture is stirred for 4 h. The solid is filtered off and washed with dichloromethane. The filtrate is concentrated under reduced pressure. The residue is chromatographed using a gradient of 0% ethyl acetate in hexane to 50% ethyl acetate in hexane to yield the title compound (2.95 g, 93%) as a pale yellow solid. ES/MS m/e 454 (M−1).

Preparation 22

Benzo[b]thiophene-5-carboxylic acid ethyl ester

A saturated solution of HCl in ethanol (15 mL) is added to benzothiophene-5-carboxylic acid (1 g, 5.44 mmol) and the reaction mixture is stirred at 80° C. overnight. The solvent is removed under reduced pressure and diethyl ether and saturated sodium bicarbonate are added to the residue. The layers are separated. The organic layer is washed with saturated sodium bicarbonate and water, dried over anhydrous sodium sulfate, filtered, and concentrated under reduced pressure to yield the title compound (1.0 g, 89%) as a pale brown oil. $^1$H NMR (CDCl$_3$): δ 8.54 (s, 1H), 8.01 (d, 1H, J=8.1 Hz), 7.92 (d, 1H, J=8.1 Hz), 7.51 (d, 1H, J=5.4 Hz), 7.42 (d, 1H, J=5.4 Hz), 4.42 (c, 2H, J=6.8 Hz), 1.43 (t, 3H, J=6.8 Hz).

Preparation 23

Benzo[b]thiophene-7-carboxylic acid methyl ester

Acetyl chloride (14.8 mmol; 1.05 mL) is added to a solution of benzo[b]thiophene-7-carboxylic acid (4.94 mmol; 880 mg) in methanol (20 mL). The reaction mixture is stirred at reflux for 24 h. The solvent is removed under reduced pressure. The residue is taken up in ethyl acetate washed with water, dried over anhydrous sodium sulfate, filtered, and concentrated under reduced pressure to yield the title compound (880 mg, 92%) as colorless oil. $^1$H NMR (CDCl$_3$): δ 8.12 (dd, 1H, J=7.2 Hz, 0.6 Hz), 8.03 (dd, 1H, J=7.6 Hz, 1.2 Hz), 7.58 (d, 1H, J=5.6 Hz), 7.46 (t, 1H, J=7.6 Hz), 7.41 (t, 1H, J=5.2 Hz), 4.03 (s, 3H).

Preparation 24

2-(4-Methoxy-2-methyl-phenyl)-benzo[b]thiophene-5-carboxylic acid ethyl ester Cesium carbonate (9.70 mmol; 3.19 g) is dried in a resealable tube at 150° C. in vacuo for 2 h and cooled to room temperature. Copper(I) iodide (9.70 mmol; 1.86 g), Pd(OAc)$_2$ (0.24 mmol; 55 mg), triphenylphosphine (0.485 mmol; 128.50 mg), 2-bromo-5-methoxytoluene (9.70 mmol; 2.14 mL), benzo[h]thiophene-5-carboxylic acid ethyl ester (4.85 mmol; 1 g) and anhydrous dimethylformamide (24 mL) are added under nitrogen atmosphere and the mixture is stirred at 140° C. After 24 h, Pd(OAc)$_2$ (0.24 mmol; 55 mg) and triphenylphosphine (0.485 mmol; 128.50 mg) are added and the mixture is stirred for 24 hours. The mixture is allowed to cool to room temperature followed by the addition of water and ethyl acetate. The suspension is filtered through Celite® and washed with ethyl acetate. The organic layer is separated and the aqueous layer is extracted with ethyl acetate. The organic layers are combined, washed with water, dried over anhydrous sodium sulfate, filtered and concentrated under reduced pressure. The residue is chromatographed using a gradient of 0% ethyl acetate in hexane to 10% ethyl acetate in hexane to yield the title compound (960 mg, 61%) as a colorless waxy solid. ES/MS m/e 326 (Ma).

Preparation 25

2-(4-Methoxy-2-methyl-phenyl)-benzo[b]thiophene-7-carboxylic acid methyl ester The title compound (130 mg, 12%) is prepared essentially as described in the synthesis of 2-(4-methoxy-2-methyl-phenyl)-benzo[b]thiophene-5-carboxylic acid ethyl ester, utilizing benzo[b]thiophene-7-carboxylic acid methyl ester. $^1$H NMR (CDCl$_3$): δ 8.08 (dd, 1H, J=7.55 Hz, 1.1 Hz), 7.97 (dd, 1H, J=7.8 Hz, 1.1 Hz), 7.48-7.42 (m, 2H), 6.87-6.79 (m, 2H), 4.03 (s, 3H), 3.85 (s, 3H), 2.48 (s, 3H).

Preparation 26

2-(4-Hydroxy-2-methyl-phenyl)-benzo[b]thiophene-5-carboxylic acid ethyl ester To a 0° C. solution of 2-(4-Methoxy-2-methyl-phenyl)-benzo[b]thiophene-5-carboxylic acid ethyl ester (1.07 mmol; 350 mg) in anhydrous dichloromethane (4.00 mL) is added a 1 M solution of boron tribromide (1.29 mmol; 1.29 mL) in dichloromethane. The reaction mixture is stirred at room temperature for 4 h. Water and ethyl acetate are added. The aqueous layer is separated and the organic layer is dried over anhydrous sodium sulfate, filtered and concentrated under reduced pressure. The residue is dissolved in ethanol (5 mL) and acetyl chloride (3.48 mmol, 0.25 mL) is added. The mixture is stirred at reflux for 5 h. The solvent is removed under reduced pressure and the residue is chromatographed using a gradient of 5% ethyl acetate in hexane to 20% ethyl acetate in hexane to yield the title compound (145 mg, 40%) as a white solid. ES/MS m/e 313 (M+1).

Preparation 27

2-(4-Hydroxy-2-methyl-phenyl)-benzo[b]thiophene-7-carboxylic acid methyl ester The title compound (85 mg, 69%) is prepared essentially as described in the synthesis of 2-(4-Hydroxy-2-methyl-phenyl)-benzo[h]thiophene-5-carboxylic acid ethyl ester, utilizing 2-(4-Methoxy-2-methyl-phenyl)-benzo[b]thiophene-7-carboxylic acid methyl ester and methanol. ES/MS m/e 297 (M−1).

Preparation 28

Step 1

3-Cyclopropylamino-but-2-enoic acid ethyl ester

A mixture of ethyl acetoacetate (5.00 mL, 39.3 mmol) and cyclopropylamine (3.27 mL, 47.1 mmol) is stirred at 40° C. for 3 h. The mixture is concentrated under high vacuum overnight to give the title compound (6.23 g, 94%) of the as an oil, which is used without further purification in the next reaction.

Step 2

1-Cyclopropyl-5-hydroxy-2-methyl-1H-indole-3-carboxylic acid ethyl ester

Neat 3-cyclopropylamino-but-2-enoic acid ethyl ester (5.63 g, 33.2 mmol) is added to a mixture of p-benzoquinone (7.19 g, 66.5 mmol) and acetic acid (120 mL). The mixture is stirred at room temperature for 5 h and a dark solid is precipitated. The solid is washed with acetic acid and water, dried, adsorbed onto silica gel, and purified via flash chromatography eluting with dichloromethane. The product is triturated in dichloromethane-hexane to afford the title compound (440 mg, 21%). ES/MS m/e 260.0 (M+1)

Step 3

6-Bromo-1-cyclopropyl-5-hydroxy-2-methyl-1H-indole-3-carboxylic acid ethyl ester Bromine (277 µL, 5.40 mmol) is added to a suspension of 1-cyclopropyl-5-hydroxy-2-methyl-1H-indole-3-carboxylic acid ethyl ester (1.40 g, 5.40 mmol) in acetic acid (50 mL). The mixture is stirred for one hour at room temperature. The mixture is diluted with water and the resultant solids are filtered and washed with water. The solids are adsorbed onto silica gel and purified via flash chromatography eluting with 30% THF-heptane. The fractions are combined to yield the title compound (763 mg, 42%). ES/MS m/e 339.8 (M+1).

Step 4

6-Bromo-1-cyclopropyl-5-methoxy-2-methyl-1H-indole-3-carboxylic acid ethyl ester Sodium hydride (60% in mineral oil, 71 mg, 1.8 mmol) is added to a solution of 6-bromo-1-cyclopropyl-5-hydroxy-2-methyl-1H-indole-3-carboxylic acid ethyl ester (200 mg, 0.590 mmol) in DMF (4.0 mL). The mixture is stirred for 20 minutes at room temperature. Methyl iodide (110 µL, 1.77 mmol) is added and the mixture is stirred for 1 h at room temperature. The mixture is diluted with water and ether. The layers are separated. The ether layer is washed with water and brine, dried over $MgSO_4$, and concentrated under reduced pressure. The residue is triturated in ethyl acetate-hexane to give the title compound as an off-white solid (183 mg, 88%). ES/MS m/e 353.8 (M+1).

Step 5

1-Cyclopropyl-6-(4-hydroxy-2-methyl-phenyl)-5-methyl-2-methyl-1H-indole-3-carboxylic acid ethyl ester A mixture of 6-bromo-1-cyclopropyl-5-methoxy-2-methyl-1H-indole-3-carboxylic acid ethyl ester (355 mg, 1.01 mmol), 3-methyl-4-(4,4,5,5-tetramethyl-[1,3,2]dioxaborolan-2-yl)-phenol (472 mg, 2.20 mmol), tetrakis(triphenylphosphene)palladium (87 mg, 0.075 mmol), aqueous sodium carbonate (2 M, 3.0 mL, 6.00 mmol), DMF (5.9 mL) and ethanol (5.9 mL) is heated under nitrogen at 85° C. for 4 h. The mixture is acidified with 1 N HCl and extracted with ethyl acetate. The ethyl acetate layers are combined and washed with water and brine and dried over $MgSO_4$. The residue is purified via flash chromatography eluting with THF-heptane (25→40%) to afford the title compound (187 mg, 49%) as a white solid. ES/MS m/e 380.0 (M+1).

Preparation 29

6-Chloro-1-isopropyl-2-methyl-1H-indole-3-carboxylic acid methyl ester

Step 1

2-(4-Chloro-2-nitro-phenyl)-3-hydroxy-but-2-enoic acid methyl ester

A mixture of sodium hydride (60% in mineral oil, 2.60 g, 65.0 mmol) and DMF (52 mL) is stirred in an ice bath and methylacetoacetate (6.46 mL, 59.9 mmol) is added via a syringe over 10 minutes. The mixture is stirred for an additional 10 minutes and the ice bath is removed. The solution is stirred at ambient temperature for 30 minutes and transferred via cannula into a flask containing 4-chloro-1-fluoro-2-nitrobenzene (5.00 g, 28.5 mmol) cooled to 0° C. via an ice bath. The reaction is allowed to warm slowly and is stirred for two days at room temperature. The black mixture is acidified with 2 N HCl, turning it yellow. The resulting solution is diluted with water and extracted with ether. The combined ether layers are washed with water and brine and dried over $MgSO_4$ to give the crude title compound (8.26 g), which contains a small amount of mineral oil. The material is used without purification in the next step.

Step 2

6-Chloro-2-methyl-1H-indole-3-carboxylic acid methyl ester

A mixture of iron (5.76 g, 103 mmol), 2-(4-chloro-2-nitrophenyl)-3-hydroxy-but-2-enoic acid methyl ester (3.84 g, 17.2 mmol) and glacial acetic acid (16 mL) is heated at 115° C. for 1 h. The mixture is diluted with water and extracted repeatedly with ethyl acetate. The pooled ethyl acetate layers are washed with brine and dried over $MgSO_4$. The residue is adsorbed onto silica gel and purified via flash chromatography (120 g $SiO_2$) eluting with a gradient of 70% to 100% $CH_2Cl_2$-heptane to give the title compound (1.28). ES/MS m/e 224.0 (M+1).

Step 3

6-Chloro-1-isopropyl-2-methyl-1H-indole-3-carboxylic acid methyl ester

A mixture of 6-chloro-2-methyl-1H-indole-3-carboxylic acid methyl ester (300 mg, 1.34 mmol), 2-bromopropane (1.75 mL, 18.6 mmol), potassium carbonate (743 mg, 5.37 mmol) and DMF (3.5 mL) is heated to 100° C. for 14 h. The mixture is diluted with water and extracted with ether. The ether layers are washed with water and brine and dried over $MgSO_4$. The residue is purified via flash chromatography eluting with 80% $CH_2Cl_2$-heptane to give the title compound (217 mg, 61%) as a white solid. ES/MS m/e 266.0 (M+1).

Preparation 30

6-(4-Hydroxy-2-methyl-phenyl)-1-isopropyl-2-methyl-1H-indole-3-carboxylic acid methyl ester A mixture of 6-chloro-1-isopropyl-2-methyl-1H-indole-3-carboxylic acid methyl ester (200 mg, 0.75 mmol), 3-methyl-4-(4,4,5,5-tetramethyl-[1,3,2]dioxaborolan-2-yl)-phenol (351 mg, 1.50 mmol), dioxane (2.5 mL), potassium phosphate tribasic, N-hydrate (2.59 g, 1.28 mmol), tris(dibenzylideneacetone)dipalladium(0) (12 mg, 0.013 mmol) and tricyclohexylphosphine (9 mg, 0.03 mmol) is stirred under nitrogen at 120° C. for 16 h. The mixture is acidified with 1N HCl, diluted with water, and extracted with ether. The combined ether layers are washed with brine and dried over $MgSO_4$. The crude product is purified via flash chromatography (40 g $SiO_2$) cluting with 30% THF-heptane to yield the title compound (223 mg, 88%) as a white solid. ES/MS ma/c 338.0 (M+1).

Preparation 31

6-(4-Hydroxy-2-methyl-phenyl)-1,2-dimethyl-1H-indole-3-carboxylic acid methyl ester The title compound is prepared essentially according to the preparation of 6-(4-hydroxy-2-methyl-phenyl)-1-isopropyl-2-methyl-1H-indole-3-carboxylic acid methyl ester utilizing 6-Chloro-1,2-dimethyl-1H-indole-3-carboxylic acid methyl ester. ES/MS m/c 310.3 (M+1).

Preparation 32

6-(4-Hydroxy-2-methyl-phenyl)-benzo[d]isoxazole-3-carboxylic acid ethyl ester Step 1

(4-bromo-2-nitro-phenyl)-acetic acid methyl ester

A solution of (4-bromo-2-nitro-phenyl)-acetic acid (5.00 g, 19.2 mmol) in methanol (100 mL) is treated with conc. HCl (1.0 mL). The mixture is stirred at 85° C. for 16 hours and cooled to room temperature. The mixture is neutralized with aqueous $Na_2CO_3$ and concentrated under reduced pressure. The residue is extracted with ethyl acetate (50 mL×2), and the combined organic layers are dried over sodium sulfate and concentrated under reduced pressure to provide the title compound (5.27 g, 100%) as a brown solid.

Step 2

6-bromo-benzo[d]isoxazole-3-carboxylic acid ethyl ester

A solution of (4-bromo-2-nitro-phenyl)-acetic acid methyl ester (0.99 g, 3.61 mmol) in ethanol (8 mL) at room temperature is treated with isoamyl nitrite (0.60 mL, 4.47 mmol). A solution of NaOEt in ethanol (1.9 M, 2.0 mL) is added, and the mixture is stirred at 60° C. for 2 hours and at room temperature for 16 hours. The mixture is neutralized with HCl (1.0 M, 4.0 mL) and concentrated under reduced pressure. The residue is extracted with ethyl acetate (20 mL×2) and the combined organic layers are dried over sodium sulfate and concentrated under reduced pressure. The residue is purified via silica gel chromatography eluting with 25% ethyl acetate in hexanes to give the title compound (0.36 g, 37%). ES/MS m/e 269.8; 271.8 (M+1).

Step 3

6-(4-Hydroxy-2-methyl-phenyl)-benzo[d]isoxazole-3-carboxylic acid ethyl ester

A solution of 3-methyl-4-(4,4,5,5-tetramethyl-[1,3,2]dioxaborolan-2-yl)-phenol (0.624 g, 2.67 mmol) and 6-bromo-benzo[d]isoxazole-3-carboxylic acid ethyl ester (0.360 g, 1.33 mmol) in 1,4-dioxane (20 mL) is added to a flask. The flask is evacuated and re-filled with $N_2$ 3 times. To this solution, $Pd_2(dba)_3$ (0.010 g), tricyclohexyl phosphine (10 mg), and aqueous $K_3PO_4$ (1.5 mL, 1.30 M) are added. The resulting mixture is heated to 50° C. for 2 hours under $N_2$. The reaction mixture is cooled to room temperature and filtered through a pad of diatomaceous earth. The filtrate is concentrated under reduced pressure. The residue is purified via silica gel chromatography eluting with 25% ethyl acetate in hexanes to give the title compound (0.366 g, 93%). ES/MS m/e 298.0 (M+1); 296.0 (M−1).

Preparation 33

2-Methyl-6-(4,4,5,5-tetramethyl-[1,3,2]dioxaborolan-2-yl)-benzofuran-3-carboxylic acid methyl ester Step 1

6-methoxy-2-methyl-benzofuran

A solution of 2-iodo-5-methoxy-phenol (39 g, 156 mmol) in dimethylformamide (300 mL) and N,N,N',N'-tetramethylguanidine (150 mL) is treated with copper(I) Iodide (1.89 g, 9.82 mmol) and bis(triphenylphosphine)palladium(II) chloride (1.9 g; 2.71 mmol; 1.900 g). The mixture is cooled to −78° C. Propyne (100 g; 2.50 moles) is bubbled through the mixture for 1 hour. The reaction mixture is stirred and allowed to warm to room temperature gradually over 6 hours and stirred for 2 days. The reaction mixture is quenched with water (800 mL) and extracted with EtOAc (500 mL). The organic layers are dried over $Na_2SO_4$, filtered, and concentrated under reduced pressure. The crude product is purified via flash chromatography eluting with 10% EtOAc/Hexanes. The appropriate fractions are concentrated. The material is dried in vacuo to afford the title compound (17.5 g, 69%). $^1$H NMR (400 MHz, $CDCl_3$): δ 7.31-7.29 (d, 1H), 6.95 (s, 1H), 6.81-6.79 (d, 1H), 6.26 (s, 1H), 3.81 (s, 3H), 2.40 (s, 3H).

Step 2

Acetic acid 2-methyl-benzofuran-6-yl ester

A solution of 6-methoxy-2-methyl-benzofuran (17.4 g, 107 mmol) in dichloromethane (200 mL) at 0° C. is treated with boron tribromide (1.0 M, 107 mL). The mixture is stirred at 0° C. for 60 minutes and quenched with water (50 mL). The organic layer is dried over $Na_2SO_4$, filtered, and concentrated under reduced pressure. The crude product is purified by flash chromatography eluting with 25% EtOAc/Hexanes. The appropriate fractions are concentrated under reduced pressure. The resulting material is dissolved in dichloromethane (150 mL) and triethylamine (17.0 mL, 122 mmol) at 0° C. and treated with acetic acid anhydride (7.22 mL, 76.35 mmol). The reaction is stirred for 16 hours and allowed to warm to room temperature. The reaction is quenched with MeOH (100 mL) and concentrated under reduced pressure. The residue is purified by silica gel chromatography eluting with 25% EtOAc/Hexanes to provide the title compound (9.50 g, 82%). $^1$H NMR (400 MHz, $CDCl_3$): δ 7.40-7.38 (d, 1H), 7.15 (s, 1H), 6.91-6.88 (d, 1H), 6.32 (s, 1H), 2.41 (s, 3H), 2.29 (s, 3H).

Step 3

6-hydroxy-2-methyl-benzofuran-3-carboxylic acid

To a slurry of aluminum trichloride (20.0 g, 150 mmol) in dichloromethane (200 mL) is added oxalyl chloride (13.0 mL, 150 mmol). The mixture is stirred at 0° C. for 30 minutes. A solution of acetic acid 2-methyl-benzofuran-6-yl ester (9.50 g; 49.9 mmol) in dichloromethane (50 mL) is added over 10 minutes. The ice-bath is removed and the reaction is stirred at room temperature for 2 hours. The reaction mixture is cooled to 0° C. and quenched with MeOH (50 mL). The mixture is concentrated to a residue under reduced pressure, dissolved in methanol (250 mL), and treated with potassium carbonate (8.28 g, 59.9 n-mol). The mixture is stirred at room temperature for 16 hours, filtered through a pad of diatomaceous earth, and concentrated under reduced pressure. The residue is diluted with water (100 mL) and extracted with EtOAc (250 mL×2). The combined organic layers are dried over $Na_2SO_4$, filtered, and concentrated under reduced pressure. The crude product is purified by flash chromatography eluting with 25% EtOAc/Hexanes. The appropriate fractions are combined and concentrated under reduced pressure to afford the title compound (9.56 g, 93%). MS: 207.0 (M+1); 205.0 (M−1).

Step 4

2-methyl-6-trifluoromethanesulfonyloxy-benzofuran-3-carboxylic acid methyl ester A 0° C. solution of 6-hydroxy-2-methyl-benzofuran-3-carboxylic acid methyl ester (9.5 g, 46.07 mmol) in dichloromethane (100 mL) and triethylamine (12.8 mL, 92.14 mmol) is treated with trifluoromethanesulfonic anhydride (8.54 L, 50.68 mmol). The reaction mixture is stirred at 0° C. for 60 minutes and quenched with MeOH (10 mL). The mixture is concentrated to a residue under reduced pressure. The residue is purified by silica gel chromatography eluting with 20% EtOAc/Hexanes to provide the title compound (14.1 g, 90%). $^1$H NMR (400 MHz, CDCl$_3$): δ 7.99-7.96 (d, 1H), 7.37 (s, 1H), 7.21-7.18 (d, 1H), 3.93 (s, 3H), 2.76 (s, 3H).

Step 5

2-methyl-6-(4,4,5,5-tetramethyl-[1,3,2]dioxaborolan-2-yl)-benzofuran-3-carboxylic acid methyl ester A solution of 2-methyl-6-trifluoromethanesulfonyloxy-benzofuran-3-carboxylic acid methyl ester (3.25 g, 9.61 mmol) and bis(pinacolato)diboron (3.05 g, 12.0 mmol) in acetonitrile (50 mL) is added to a flask. The flask is evacuated via vacuum and re-filled with nitrogen gas three times. Tricyclohexylphosphine (108 mg, 0.384 mmol), Pd(OAc)$_2$ (43 mg, 0.192 mmol), and cesium fluoride (2.92 g, 19.2 mmol) are added and the mixture is heated to 85° C. for 16 hours. The reaction mixture is cooled to room temperature and filtered through a pad of diatomaceous earth. The filtrate is concentrated to a residue. The residue is purified by silica gel chromatography eluting with 15% EtOAc/Hexanes to provide the title compound (1.96 g, 65%). ES/MS m/e 317.0 (M+1).

Preparation 34

[6-(4,4,5,5-Tetramethyl-[1,3,2]dioxaborolan-2-yl)-benzo[b]thiophen-3-yl]-acetic acid methyl ester

Step 1

4-(3-methoxy-phenylsulfanyl)-3-oxo-butyric acid ethyl ester

To a 0° C. solution of 3-methoxy-benzenethiol (5.75 g, 41.0 mmol) and potassium carbonate (11.45 g, 82.02 mmol) in acetonitrile (150 mL) is added butanoic acid, 4-chloro-3-oxo-butanoic acid ethyl ester 6.12 mL, 45.11 mmol). The mixture is stirred at room temperature for 2 hours and filtered through a pad of diatomaceous earth. The filtrate is concentrated under reduced pressure. The residue is purified via silica gel chromatography eluting with 25-30% EtOAc/Hexanes to provide the title compound (10.9 g, 99%). MS: 267.0 (M−1)

Step 2

4-methoxy-benzo[b]thiophen-3-yl-acetic acid ethyl ester 4-(3-methoxy-phenylsulfanyl)-3-oxo-butyric acid ethyl ester (10.9 g, 40.62 mmol) is added to methanesulfonic acid (26.6 mL, 406 mmol). The mixture is stirred at room temperature for 30 minutes. The reaction mixture is poured into ice-water (300 g) and extracted with EtOAc (100 mL×2). The combined organic layers are dried over Na$_2$SO$_4$, filtered, and concentrated under reduced pressure. The crude product is purified by flash chromatography eluting with 20% EtOAc/Hexanes. The appropriate fractions are combined and concentrated under reduced pressure to afford the title compound (6.00 g, 59%). ES/MS n/e 251.0 (M+1)

Step 3

(6-hydroxy-benzo[b]thiophen-3-yl)-acetic acid ethyl ester

To a −78° C. solution of (6-methoxy-benzo[b]thiophen-3-yl)-acetic acid ethyl ester (3.81 g, 15.22 mmol) in dichloromethane (50 mL) is added boron tribromide (38.1 mL, 38.1 mmol) dropwise. The mixture is allowed to warm to room temperature and stirred for 16 hours. The mixture is cooled to 0° C. and quenched with water (100 mL). The organic layer is separated, and the aqueous layer is extracted with EtOAc (50 mL). The combined organic layers are dried over Na$_2$SO$_4$, filtered, and concentrated under reduced pressure. The crude product is purified by flash chromatography eluting with 30-40% EtOAc/Hexanes. The appropriate fractions are combined and concentrated under reduced pressure to afford the title compound (3.35 g, 93%). ES/MS m/e 237.0 (M+1); 235.0 (M−1).

Step 4

(6-trifluoromethanesulfonyloxy-benzo[b]thiophen-3-yl)-acetic acid ethyl ester

To a −78° C. solution of (6-hydroxy-benzo[b]thiophen-3-yl)-acetic acid ethyl ester (3.31 g, 14.0 mmol) in dichloromethane (50 mL) is added triethylamine (3.90 mL, 28.0 mmol) and trifluoromethanesulfonic anhydride (2.60 mL, 15.4 mmol). The mixture is allowed to warm to room temperature and stirred and for 30 minutes. The reaction is quenched with MeOH (5.0 mL) and concentrated under reduced pressure. The residue is purified via silica gel chromatography eluting with 20% EtOAc/Hexanes to provide the title compound (5.05 g, 98%). ES/MS m/e 366.8 (M−1).

Step 5

[6-(4,4,5,5-tetramethyl-[1,3,2]dioxaborolan-2-yl)-benzo[b]thiophen-3-yl]-acetic acid ethyl ester A solution of (6-trifluoromethanesulfonyloxy-benzo[b]thiophen-3-yl)-acetic acid ethyl ester (2.21 g, 6.00 mmol) and bis(pinacolato)diboron (1.90 g, 7.50 mmol) in acetonitrile (25 mL) is evacuated and refilled with N$_2$ three times. Pd(OAc)$_2$ (27 mg, 0.12 mmol), tricyclohexylphosphine (67 mg, 0.24 mmol), and cesium fluoride (1.82 g, 12.00 mmol) are added. The mixture is stirred at 95° C. for 1 hour and quenched with water (5 mL). The mixture is filtered through a pad of diatomaceous earth and the filtrate is concentrated under reduced pressure. The residual aqueous solution is extracted with EtOAc (20 mL×2). The combined organic layers are dried over Na$_2$SO$_4$, filtered, and concentrated under reduced pressure. The crude product is purified via flash chromatography eluting with 20% EtOAc/Hexanes. The appropriate fractions are combined and concentrated under reduced pressure to afford the title compound (1.56 g, 75%). ES/MS m/e (M+1): 364.0; (M+1):347.0

Preparation 35

(6-bromo-benzo[b]thiophen-2-yl)-acetic acid methyl ester

Step 1

6-bromo-benzo[b]thiophene-2-carboxylic acid ethyl ester

Sodium hydride (1.41 g, 35.32 mmol) is added to a round bottom flask and washed with hexanes (10 mL) twice. To the flask is added dimethyl sulfoxide (30 mL) and ethyl 2-mercaptoacetate (3.54 g, 29.43 mmol). The mixture is stirred for 10 minutes and 4-bromo-2-fluoro-benzaldehyde (4.78 g; 23.55 mmol) is added. The reaction mixture is stirred for 15 minutes and quenched with ice-water (100 g). The mixture is extracted with $CH_2Cl_2$ (50 mL×2). The combined organic layers are dried over $Na_2SO_4$, filtered, and concentrated under reduced pressure. The crude product is purified via flash chromatography eluting with 10% EtOAc/Hexanes. The appropriate fractions are combined and concentrated under reduced pressure to afford the title compound (5.75 g, 86%). $^1H$ NMR (400 MHz, $CDCl_3$): δ 8.00 (s, 1H), 7.99 (s, 1H), 7.75 (d, 1H), 7.48 (d, 1H), 4.38 (q, 2H), 1.39 (t, 3H).

Step 2

(6-bromo-benzo[b]thiophene-2-yl)-methanol

A −78° C. solution of 6-bromo-benzo[b]thiophene-2-carboxylic acid ethyl ester (5.75 g; 20.2 mmol) in THF (200 mL) is treated with diisobutylaluminum hydride (50.4 mL; 1.0 M) dropwise. The mixture is stirred at 0° C. for 10 minutes and quenched with HCl (1 M, 50 mL). The mixture is extracted with EtOAc (150 mL). The organic layer is dried over $Na_2SO_4$, filtered, and concentrated under reduced pressure. The crude product is purified via flash chromatography eluting with 25% EtOAc/Hexanes. The appropriate fractions are combined and concentrated under reduced pressure to afford the title compound (2.92 g, 60%). $^1H$ NMR (400 MHz, $CDCl_3$): δ 7.95 (s, 1H), 7.68 (d, 1H), 7.42 (d, 1H), 7.18 (s, 1H), 4.90 (s, 2H).

Step 3

6-bromo-benzo[b]thiophene-2-carbaldehyde

To a −78° C. solution of oxalyl chloride (1.30 mL, 14.9 mol) in $CH_2Cl_2$ (20 mL) is added a solution of dimethyl sulfoxide (2.13 mL, 29.9 mmol) in $CH_2Cl_2$ (10 mL). The mixture is stirred for 5 minutes and a solution of (6-bromo-benzo[b]thiophen-2-yl)-methanol (2.91 g; 12.0 mmoles) in $CH_2Cl_2$ (30 mL) is added. The mixture is stirred at −78° C. for 30 minutes and triethylamine (8.34 mL, 60.0 mmol) is added. The mixture is stirred for 1 hour while warming to room temperature. The reaction mixture is quenched with water (50 mL). The organic layer is separated and concentrated under reduced pressure to a residue. The residue is purified via silica gel chromatography eluting with 20% EtOAc/Hexanes to provide the title compound (2.58 g, 89%). $^1H$ NMR (400 MHz, $CDCl_3$): δ 10.4 (s, 1H), 8.02 (s, 1H), 7.98 (s, 1H), 7.79 (d, 1H), 7.52 (d, 1H).

Step 4

(6-bromo-benzo[b]thiophen-2-yl)-acetaldehyde

To a 0° C. solution of potassium tert-butoxide (2.50 g, 21.4 mmol) in tetrahydrofuran (100 mL) is added (methoxymethyl)triphenylphosphonium chloride (7.49 g, 21.4 mmol). The reaction mixture is stirred for 20 minutes. 6-Bromo-benzo[b]thiophene-2-carbaldehyde (2.58 g; 10.7 mmol) is added and the ice-bath is removed. The mixture is stirred at room temperature for 16 hours. The reaction mixture is quenched with AcOH (5 mL). The mixture is treated with water (50 mL) and concentrated to a residue under reduced pressure. The residual aqueous solution is extracted with EtOAc (50 mL×2). The combined organic layers are dried over $Na_2SO_4$, filtered, and concentrated under reduced pressure. The crude product is purified via flash chromatography eluting with 10% EtOAc/Hexanes. The appropriate fractions are combined and concentrated under reduced pressure to a residue. The residue is dissolved in THF (50 mL) and treated with HCl (5 N, 5 mL). The mixture is stirred at 70° C. for 60 minutes and neutralized with NaOH (5 N, 5 mL). The mixture is concentrated to a residue under reduced pressure. The residual aqueous mixture is extracted with EtOAc (50 mL×2). The combined organic layers are dried over $Na_2SO_4$, filtered, and concentrated under reduced pressure. The crude product is purified via silica gel chromatography eluting with 25% EtOAc/Hexanes to provide the title compound (2.25 g, 82%). ES/MS m/e 254.8, 252.8 (M−1).

Step 5

(6-bromo-benzo[b]thiophen-2-yl)-acetic acid methyl ester

To a 0° C. solution of (6-bromo-benzo[b]thiophen-2-yl)-acetaldehyde (2.21 g; 8.66 mmol) in t-butyl alcohol (50 mL; 526.36 mmoles; 50.00 mL; 39.015 g) and 2-methyl-2-butene (20 mL; 188 mmol) is added a solution of sodium chlorite (6.27 g; 69.3 mmol) in water (20 mL) and a solution of sodium phosphate monobasic (4.20 g; 34.6 mmol) in water (10 mL). The reaction mixture is stirred at 0° C. for 12 hours while warming to room temperature. The mixture is extracted with EtOAc (50 mL×2). The combined organic layers are dried over $Na_2SO_4$, filtered, and concentrated under reduced pressure. The crude product is dissolved in methanol (30 mL). Sulfuric acid (1.0 mL; 18.8 mmol) is added and the mixture is stirred at 95° C. for 4 hours. The mixture is neutralized with aqueous $NaHCO_3$ and concentrated under reduced pressure. The residual aqueous mixture is extracted with EtOAc (50 mL×2). The combined organic layers are dried over $Na_2SO_4$, filtered, and concentrated under reduced pressure. The crude product is purified via flash chromatography eluting with 20% EtOAc/Hexanes. The appropriate fractions are combined and concentrated under reduced pressure to afford the title compound (1.51 g, 61%). ES/MS m/e (M+18):303.8; (M−1):284.7

Preparation 36

(1-Methyl-6-trifluoromethanesulfonyloxy-1H-indol-3-yl)-acetic acid methyl ester

Step 1

(6-benzyloxy-1H-indol-3-yl)-oxo-acetic acid methyl ester

A 0° C. solution of 6-benzyloxyindole (2.10 g, 9.41 mmol) in diethyl ether (20 mL) is treated with oxalyl chloride (1.02 mL, 11.8 mmol). The mixture is stirred for 2 hours while warming to room temperature. The mixture is cooled to −78° C. and sodium methoxide (5.41 mL, 4.35 M) is added. The mixture is warmed up to room temperature over 20 minutes and the reaction is quenched with water (10 mL). The resulting mixture is filtered to obtain the title compound (2.75 g, 95%) as a yellow solid. ES/MS m/e 310.0 (M+1), 308.0 (M−1).

Step 2

(6-benzyloxy-1-methyl-1H-indol-3-yl)-oxo-acetic acid methyl ester

A 0° C. suspension of (6-benzyloxy-1H-indol-3-yl)-oxo-acetic acid methyl ester (2.70 g, 8.73 mmol) in dimethylformamide (25 mL) is treated with sodium hydride (437 mg, 10.9 mmol). The mixture is stirred at 0° C. for 20 minutes. Methyl iodide (1.00 mL; 16.1 mmol) is added. The reaction mixture is stirred at 0° C. for 30 minutes and quenched with water (100 mL). The mixture is extracted with EtOAc (50 mL×2). The combined organic layers are dried over Na$_2$SO$_4$, filtered, and concentrated under reduced pressure. The crude product is purified by flash chromatography eluting with 60% EtOAc/Hexanes. The appropriate fractions are combined and concentrated under reduced pressure to afford the title compound (0.68 g, 24%). ES.MS m/e 324.0 (M+1).

Step 3

(6-hydroxy-1-methyl-1H-indol-3-yl)-acetic acid methyl ester

To a solution of (6-benzyloxy-1-methyl-1H-indol-3-yl)-oxo-acetic acid methyl ester (0.68 g, 2.10 mmol) in 1,4-dioxane (12 mL) is added a slurry of Pd/C (10%, 0.25 g). The flask is evacuated and re-filled with N$_2$ three times. The mixture is heated to 100° C. and a solution of sodium hypophosphite, hydrate (5.0 g, 47 mmol) in water (5 mL) is added dropwise. The mixture is stirred at 100° C. for 16 hours and cooled to room temperature. The mixture is filtered through a pad of diatomaceous earth and the filtrate is concentrated under reduced pressure. The residue is purified via silica gel chromatography eluting with 25-50% EtOAc/Hexanes to provide the title compound (0.24 g, 52%). ES/MS m/e 220.0 (M+1), 218.0 (M−1).

Step 4

(1-Methyl-6-trifluoromethanesulfonyloxy-1H-indol-3-yl)-acetic acid methyl ester

A −40° C. solution of (6-hydroxy-1-methyl-1H-indol-3-yl)-acetic acid methyl ester (0.231 g, 1.05 mmol) in dichloromethane (20 mL) and triethylamine (0.294 mL, 2.11 mmol) is treated with trifluoromethanesulfonic anhydride (0.266 mL, 1.58 mmol). The mixture is stirred at −40° C. for 2 hours and quenched with MeOH (1.0 mL). The mixture is concentrated to a residue which is purified by silica gel chromatography eluting with 25-30% EtOAc/Hexanes to provide the title compound (0.26 g, 71%). ES/MS m/e 351.8 (M+1), 368.8 (M+18).

Preparation 37

6-trifluoromethanesulfonyloxy-benzofuran-3-carboxylic acid ethyl ester

Step 1

Trifluoro-methanesulfonic acid 6-methoxy-benzofuran-3-yl ester

A −70° C. solution of 6-methoxy-benzofuran-3-one (5.12 g, 31.2 mmol) in CH$_2$Cl$_2$ (100 mL) and diisopropylethylamine (6.53 mL, 37.4 mmol) is treated with trifluoromethanesulfonic anhydride (6.31 mL, 37.4 mmol). The mixture is stirred while warming to 0° C. over 2 hours. The mixture is quenched with water (20 mL). The organic layer is separated, dried over Na$_2$SO$_4$, and concentrated under reduced pressure. The residue is purified via silica gel chromatography eluting with 10% EtOAc/Hexanes to provide the title compound (9.10 g, 98%). $^1$H NMR (400 MHz, CDCl$_3$): δ 7.70 (s, 1H), 7.43 (d, 1H), 6.99 (s, 1H), 6.96 (d, 1H), 3.82 (s, 3H).

Step 2

6-Methoxy-benzofuran-3-carboxylic acid ethyl ester

In a steel high-pressure reaction vessel, a solution of trifluoro-methanesulfonic acid 6-methoxy-benzofuran-3-yl ester (9.10 g, 30.7 mmol) in dimethylformamide (120 mL) is bubbled with carbon monoxide gas for 10 minutes. Ethanol (60 mL), triethylamine (9.25 mL), Pd(OAc)$_2$ (0.20 g), bis-(1,3-diphenylphosphino)propane (0.38 g) are added to the reaction mixture. The mixture vessel is sealed, charged with carbon monoxide (10 g, 30 psi), and heated to 80° C. for 4.5 hours. The mixture is concentrated under reduced pressure and diluted with water (300 mL), and extracted with EtOAc (150 mL×2). The combined organic layers are dried over Na$_2$SO$_4$, filtered, and concentrated under reduced pressure. The crude product is purified via flash chromatography eluting with 15% EtOAc/Hexanes. The appropriate fractions are combined and concentrated under reduced pressure to afford the title compound (5.50 g, 81%). $^1$H NMR (400 MHz, CDCl$_3$): δ 8.16 (s, 1H), 7.88 (d, 1H), 7.01 (s, 1H), 6.96 (d, 1H), 4.38 (q, 2H), 3.81 (s, 3H), 1.40 (t, 3H).

Step 3

6-hydroxy-benzofuran-3-carboxylic acid ethyl ester

A −78° C. solution of 6-methoxy-benzofuran-3-carboxylic acid ethyl ester (1.50 g, 6.81 mmol) in dichloromethane (20 mL) is treated with boron tribromide (20 mL) dropwise. The mixture is stirred at 0° C. for 60 minutes. The reaction is quenched by adding MeOH (10 mL) dropwise over 10 minutes. The mixture is concentrated. The residue is purified via flash chromatography eluting with 25% EtOAc/hexanes to provide the title compound (0.95 g, 68%). ES/MS m/e 207.0 (M+1), 205.0 (M−1).

Step 4

6-trifluoromethanesulfonyloxy-benzofuran-3-carboxylic acid ethyl ester

A −70° C. solution of 6-hydroxy-benzofuran-3-carboxylic acid ethyl ester (0.95 g) in dichloromethane (30 mL) is added triethylamine (1.28 mL, 9.21 mmol) and trifluoromethanesulfonic anhydride (0.97 mL, 5.76 mmol). The resulting mixture is stirred while warming to 0° C. over 60 minutes. The reaction is quenched with MeOH (5.0 mL) and the mixture is concentrated to a residue, which is purified by silica gel chromatography eluting with 15% EtOAc/Hexanes to provide the title compound (1.43 g, 92%). $^1$H NMR (400 MHz, CDCl$_3$): δ 8.33 (s, 1H), 8.12 (d, 1H), 7.48 (s, 1H), 7.29 (d, 1H), 4.40 (q, 2H), 1.40 (t, 3H).

Preparation 38

6-Trifluoromethanesulfonyloxy-benzofuran-2-carboxylic acid tert-butyl ester

Step 1

4-Benzyloxy-2-hydroxy-benzaldehyde

A solution of 2,4-dihydroxy-benzaldehyde (101 g, 0.731 mol) in acetonitrile (700 mL) is treated with KI (12.1 g, 73.1 mmol) and $NaHCO_3$ (70.0 g, 0.834 mol). The mixture is stirred while heating to 60° C. Benzyl chloride (120 g, 0.950 mol) is added and the mixture is refluxed at 82° C. for 16 hours and cooled to room temperature. The solvent is evaporated and the reaction is quenched with water (250 mL) and HCl (5.0 N, 30 mL). The mixture is extracted with EtOAc (300 mL×2), and the organic layers is dried over $Na_2SO_4$, filtered, and concentrated to an approximate volume of 200 mL. To 400 mL hexanes is added and the resulting solution is heated to 60° C. to dissolve. The solution is cooled to room temperature and crystallized for 16 hours The solid is filtered and dried to obtain the title compound (130 g, 78%). LC-ES/MS m/e 227.0 (M−1).

Step 2

6-Benzyloxy-benzofuran-2-carboxylic acid tert-butyl ester

To a solution of 4-benzyloxy-2-hydroxy-benzaldehyde (5.56 g, 24.4 mmol) in DMF (20 mL) is added $K_2CO_3$ (6.73 g, 48.8 mmol), bromo-acetic acid tert-butyl ester (4.75 g, 24.4 mmol), and DBU (1.0 mL). The mixture is heated to 140° C. for 2 hours and cooled to room temperature. The mixture is quenched with water (200 mL) and extracted with EtOAc (100 mL). The organic layer is dried over $Na_2SO_4$, filtered, and concentrated under reduced pressure. The residue is purified by silica gel chromatography eluting with 15% EtOAc/Hexanes to provide the title compound (5.68 g, 72%). LC-ES/MS m/e 269.0 (acid, M+1)

Step 3

6-Hydroxy-benzofuran-2-carboxylic acid tert-butyl ester

A solution of 6-benzyloxy-benzofuran-2-carboxylic acid tert-butyl ester (5.68 g, 17.5 mmol) in THF (50 mL) and MeOH (20 mL) is added to Pd/C (5%, 200 mg). The mixture is stirred under a balloon of hydrogen for 16 hours at room temperature. The mixture is filtered through a pad of diatomaceous earth and the filtrate is concentrated under reduced pressure. The residue is purified by silica gel chromatography eluting with 25% EtOAc/Hexanes to provide the title compound (3.99 g, 97%). LC-ES/MS m/e 233.0 (M−1).

Step 4

6-Trifluoromethanesulfonyloxy-benzofuran-2-carboxylic acid tert-butyl ester To a 0° C. solution of 6-hydroxy-benzofuran-2-carboxylic acid tert-butyl ester (0.51 g, 2.18 mmol) in dichloromethane (20 mL) and triethylamine (2.0 mL) is added trifluoromethanesulfonic anhydride (0.46 mL, 2.74 mmol). The mixture is stirred for 2 hours and quenched with MeOH (2.0 mL). The mixture is concentrated and the residue is purified by silica gel chromatography eluting with 15% EtOAc/Hexanes to provide (475 mg, 59%). $^1$H NMR (400 MHz, $CDCl_3$): δ 7.70 (d, 1H), 7.52 (s, 1H), 7.41 (s, 1H), 7.23 (s, 1H), 1.60 (s, 9H).

Preparation 39

6-Bromo-benzo[d]isothiazole-3-carboxylic acid

The title compound is prepared essentially as described in Procedure 3 of WO2005/092890 A2 using 3-bromo-benzenethiol. ES/MS m/e 255.0 (M−1).

Preparation 40

6-Bromo-1-isopropyl-1H-indazole-3-carboxylic acid methyl ester

Step 1

6-Bromo-1H-indazole-3-carboxylic acid methyl ester

The title compound is prepared as essentially as described in procedure 4 of WO2005092890 utilizing 6-bromo-1H-indole-2,3-dione. ES/MS nm/e 254.0 (M+1).

Step 2

6-Bromo-1-isopropyl-1H-indazole-3-carboxylic acid methyl ester

The title compound is prepared essentially as described in procedure 1d of WO2005/080389 utilizing 6-bromo-1H-indazole-3-carboxylic acid methyl ester and methyl iodide. ES/MS m/e 268.0 (M+1).

Preparation 41

6-Bromo-1 methyl-1H-indazole-3-carboxylic acid methyl ester

The title compound is prepared essentially as described in procedure 1d WO2005/080389 utilizing 6-bromo-1H-indazole-3-carboxylic acid methyl ester. ES/MS m/c 296.0 (M+1).

Preparation 42

5-(4-Hydroxy-2-methyl-phenyl)-benzofuran-2-carboxylic acid ethyl ester

A solution of 5-bromo-benzofuran-2-carboxylic acid ethyl ester (275 mg, 1.02 mmol) and 2-methyl-4-(4,4,5,5-tetramethyl-[1,3,2]dioxaborolan-2-yl)-phenol (239 mg, 1.11 mmol) in toluene (5.0 mL) and THF (5.0 mL) is added to a flask. The flask is evacuated and re-filled with $N_2$ three times. $Pd(OAc)_2$ (5 mg, 0.022 mmol) and 2-dicyclohexylphosphino-2,6-dimethoxy-1,1'-biphenyl (20 mg, 0.049) and potassium phosphate, tribasic, N-hydrate (432 mg, 2.04 mmol) are added and the mixture is heated at 85° C. for 8 hours. The reaction mixture is cooled to room temperature and filtered through a pad of diatomaceous earth. The filtrate is concentrated to a residue which is purified by silica gel chromatography eluting with 20-30% EtOAc/Hexanes to provide the title compound (179 mg, 56%). ES/MS m/e 297.0 (M+1), 295.0 (M−1).

The following list of compounds is prepared essentially as described in the preparation of 5-(4-hydroxy-2-methyl-phenyl)-benzofuran-2-carboxylic acid ethyl ester.

Preparation 42A: 6-(4-Hydroxy-2-methyl-phenyl)-benzo[d]isoxazole-3-carboxylic acid ethyl ester (0.065 g, 47%) utilizing 2-methyl-6-trifluoromethanesulfonyloxy-benzofuran-3-carboxylic acid methyl ester stirring at 100-C for 16 hours. ES/MS m/e 297.0 (M+1), 295.0 (M−1).

Preparation 42B: [6-(4-Hydroxy-2-methyl-phenyl)-benzo[b]thiophen-2-yl]-acetic acid methyl ester (40 mg, 14%) utilizing (6-bromo-benzo[b]thiophen-2-yl)-acetic acid methyl ester (255 mg; 0.894 mmol) stirring at 110° C. for 16 hours. ES/MS m/e 313.0 (M+18), 311.0 (M−1)

Preparation 42C: [6-(4-hydroxy-2-methyl-phenyl)-1-methyl-1H-indol-3-yl]-acetic acid methyl ester (40 mg, 20%) utilizing (1-methyl-6-trifluoromethanesulfonyloxy-1H-indol-3-yl)-acetic acid methyl ester stirring at 100° C. for 16 hours. ES/MS m/e 310.0 (M+1), 308.0 (M−1).

Preparation 42D: 6-(4-Hydroxy-2-methyl-phenyl)-benzofuran-3-carboxylic acid ethyl ester (160 mg, 58%) utilizing 6-trifluoromethanesulfonyloxy-benzofuran-3-carboxylic acid ethyl ester (325 mg, 0.960 mmol) stirring at 100° C. for 16 hours. ES/MS m/e 295.0 (M−1).

Preparation 42E: 6-(4-Hydroxy-2-methyl-phenyl)-benzofuran-3-carboxylic acid tert-butyl ester (98 mg, 50%) utilizing 6-trifluoromethanesulfonyloxy-benzofuran-2-carboxylic acid tert-butyl ester stirring at 100° C. for 16 hours. ES/MS m/e 323.0 (M−1).

Preparation 42F: 6-(4-Hydroxy-2-methyl-phenyl)-benzo[d]isothiazole-3-carboxylic acid methyl ester (0.12 g, 26%) utilizing 6-bromo-benzo[d]isothiazole-3-carboxylic acid stirring at 80° C. for 18 h. ES/MS m/e 300.0 (M+1).

Preparation 42G: 6-(4-Hydroxy-2-methyl-phenyl)-1-methyl-1H-indazole-3-carboxylic acid methyl ester (0.53 g, 75%) utilizing 6-bromo-1-isopropyl-1H-indazole-3-carboxylic acid methyl ester stirring at 90° C. for 18 h. ES/MS nm/e 297.0 (M+1).

Preparation 42H: 6-(4-Hydroxy-2-methyl-phenyl)-1-isopropyl-1H-indazole-3-carboxylic acid methyl ester (2.28 g, 80%) utilizing 6-bromo-1methyl-1H-indazole-3-carboxylic acid methyl ester stirring at 90° C. for 18 h. ES/MS m/c 325.0 (M+1).

Preparation 43

5-Cyclopropyl-4-[3-methyl-4-(4,4,5,5-tetramethyl-[1,3,2]dioxaborolan-2-yl)-phenoxymethyl]-3-(2-trifluoromethoxy-phenyl)-isoxazole Step 1

4-Bromomethyl-5-cyclopropyl-3-(2-trifluoromethoxy-phenyl)-isoxazole

Triphenylphosphine (1.1 equiv., 51.5 mmoles, 13.5 g) is added in small portions to a 0° C. solution of [5-Cyclopropyl-3-(2-trifluoromethoxy-phenyl)-isoxazol-4-yl]-methanol and carbon tetrabromide (1.1 equiv, 51.5 mmoles, 17.1 g) in dichloromethane (187.1 mL). The reaction mixture is stirred at ambient temperature for 15 h and concentrated under reduced pressure. The crude residue is purified via silica gel chromatography eluting with 5:1 hexanes/ethyl acetate) to afford the title compound (15 g, 88%) as a white powder.

$^1$H NMR (DMSO-d6, 500 MHz): δ 7.7-7.5 (m, 4H), 4.55 (s, 2H), 2.41 (m, 1H), 1.17 (m, 2H), 1.11 (m, 2H)

Step 2

5-Cyclopropyl-4-[3-methyl-4-(4,4,5,5-tetramethyl-[1,3,2]dioxaborolan-2-yl)-phenoxymethyl]-3-(2-trifluoromethoxy-phenyl)-isoxazole To a 5-L 3-neck round bottom flask with a mechanical stirrer, thermocouple, reflux condenser, and drying tube is added 4-bromomethyl-5-cyclopropyl-3-(2-trifluoromethoxy-phenyl)-isoxazole (221.7 g, 0.612 mol, 1.05 eq), acetonitrile (2 L), 3-Methyl-4-(4,4,5,5-tetramethyl-[1,3,2]dioxaborolan-2-yl)-phenol (136.5 g, 0.583 mol, 1 eq) and potassium carbonate (241.8 g, 1.749 mol, 3 eq). The reaction mixture is heated to reflux and stirred at this temperature for 1 hour. Upon completion of the reaction, as evidenced by thin layer chromatography, the reaction mixture is cooled to 0-20° C. The reaction mixture is filtered and the filter cake is washed with acetonitrile (2×100 mL). The reaction mixture is concentrated under reduced pressure to a solid which is co-evaporated with 1,4-dioxane (500 mL). The title compound is used without further purification. $^1$H NMR (DMSO-d6, 300 MHz): δ 7.7-7.5 (m, 5H), 6.61 (m, 2H), 4.90 (s, 2H), 2.39 (m, 1H), 2.36 (s, 3H), 1.24 (s, 12H), 1.10 (m, 4H).

Preparation 44

6-Bromo-benzo[b]thiophene-3-carboxylic acid

The title compound is prepared essentially as described in J. Med. Chem. 2003, 46, 2446-2455.

Preparation 45

6-Bromo-benzo[b]thiophene-2-carboxylic acid

A stirred solution of 2-bromo-6-fluorobenzaldehyde (2.3 Kg, 11.33 moles) and mercaptoacetic acid (1.04 Kg, 11.33 mole) is added to a solution of KOH (951 g, 16.99 mol) in dimethylformamide (11.0 L) at room temperature. The reaction mixture is stirred for 1.5 h at 136 to 140° C. Upon completion of the reaction, the reaction mixture is cooled to 10° C. and quenched with concentrated HCl (2.5 L). The mixture is stirred for 1 h at 10° C. and the resulting solid is filtered. The filtered cake is washed with water (2×3 L) and dried under vacuum to afford the title compound (2.2 Kg, 76%) as a yellow solid.

Preparation 46

6-Bromo-benzo[b]thiophene

Copper powder (100 g, 1.57 mol) is added to a solution of 6-bromo-benzo[b]-thiophene-2-carboxylic acid (1.04 Kg, 4.04 mol) in quinoline (2.5 L) at room temperature. The reaction mixture is heated to reflux (195° C.) for 10 h. The reaction mixture is cooled to room temperature and poured onto ice (2.5 Kg). Concentrated HCl (2.5 L) is added while stirring the resulting mass for 1 h. The reaction mixture is extracted with hexane (4×3 L) and washed with dilute HCl (1×2 L), aqueous bicarbonate (1×5 L), and brine solution (1×5 L). The layers are separated and the organic layer is dried over sodium sulfate and concentrated to give the title compound (0.54 Kg, 62%) as a light yellow solid.

Preparation 47

6-Bromo-benzo[b]thiophene-3-carboxylic acid ethyl ester

Approach 1

A solution of 6-Bromo-benzo[b]thiophene-3-carboxylic acid (65 g, 252.8 mmoles) and sulfuric acid (0.10 equiv; 25.3 mmoles; 1.35 mL; 2.48 g) in ethanol (1.0 L) is heated at 65° C. for 3 days. The solution is cooled to room temperature. The resulting light brown precipitate is filtered. The filter cake is washed with methanol to afford the title compound (32 g, 44%).

Approach 2

Oxalyl chloride (717.2 g, 5.65 mol, 3.5 eq) is added to a 0-5° C. suspension of dichloromethane (3.44 L) and aluminum chloride (753.4 g, 5.65 mol, 3.5 eq). The resulting suspension is stirred for 30-60 minutes at 0-5° C. and cooled −20 to −25° C. A solution of 6-bromobenzo[b]thiophene (344 g, 1.614 mol, 1 eq) in dichloromethane (1.72 L) is added over 1 h while maintaining the temperature at −20 to −25° C. The reaction mixture is stirred for 30 minutes at −20 to −25° C. and warmed to 18 to 20° C. using a warm water bath. The reaction mixture is stirred for 1.5 h at this temperature. The reaction mixture is filtered and the filter cake is washed with dichloromethane (3×300 mL). The combined filtrate is concentrated to yield a thick black oil in the flask (600 g). This residue is dissolved in dichloromethane (1 L) and added to ethanol (3.5 L) at −10 to 0° C. in portions at such rate to maintain temperature at 10 to 20° C. Once the addition is complete, the reaction mixture is partially concentrated to remove the dichloromethane only and then the vacuum is released. The reaction mixture is heated to 60-70° C. and stirred at this temperature for 1 h. Upon completion of the reaction, the solution is decanted from the resulting tars. The tars are discarded. The ethanol solution is evaporated to a residue. The residue is diluted with EtOAc (2 L).

At this point, the current reaction mixture is combined with another reaction mixture for further work up (started with 330 g of 6-Bromobenzo[b]thiophene, 1.549 mol). The combined reaction mixture is poured into a stirred mixture of EtOAc (1 L) and brine solution (10 L). The layers are separated and the organic layer is washed with brine solution (2 L). The combined aqueous layer is extracted with EtOAc (4 L). The organic layer is washed with brine solution (1 L). The combined organic layers are dried over magnesium sulfate and charcoal, filtered, and concentrated under reduced pressure. The resulting oil is further concentrated in a vacuum oven for 15 h at room temperature to afford waxy solids after drying (750 g). The solids are suspended in heptane (5 L) with stirring and the suspension is heated to 70° C. Magnesium sulfate (300 g) is added and the resulting suspension is stirred for 10 minutes at 70° C. The suspension is filtered. The solids are suspended in heptane (5 L) and heated to 70° C. The suspension is stirred for 10-20 minutes at this temperature and filtered. The filter cake is washed with heptane (1 L). The heptane filtrates are collected and concentrated under reduced pressure to give light brown solids (550 g). The solids are dissolved in heptane (4 L) at 60° C. The resulting solution is cooled to 35 to 50° C. The solution is evenly loaded onto two plugs of silica gel (1.5 kg each) eluting with 0.5% EtOAc in heptane. The pure produce fractions axe combined and concentrated under reduced pressure. The impure product fractions are combined, concentrated, and purified as described above. The total purified product is isolated (500 g) and crystallized from heptane (1.2 L). The solids are collected by filtration, washed with cold heptane (200 mL, −20° C.), and dried in a vacuum oven at room temperature for 15 h to afford the title compound (460 g, 51%). GC analysis 98.8%; $^1$H NMR (DMSO-d6, 500 MHz): δ 8.65 (s, 1H), 8.36 (d, 1H, J=1.5), 8.33 (d, 1H, J=8.5), 7.63 (dd, 1H, J=2, 8.5), 4.33 (q, 2H, J=7), 1.33 (t, 3H, J=6.5).

Example 1

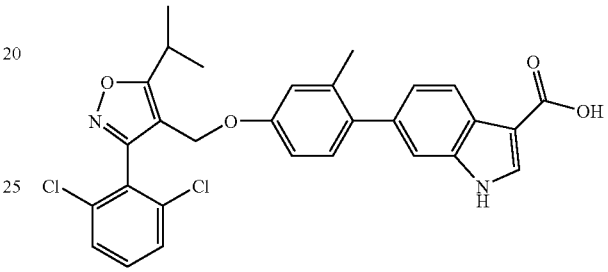

6-{4-[3-(2,6-Dichloro-phenyl)-5-isopropyl-isoxazol-4-ylmethoxy]-2-methyl-phenyl}-1H-indole-3-carboxylic acid Step 1

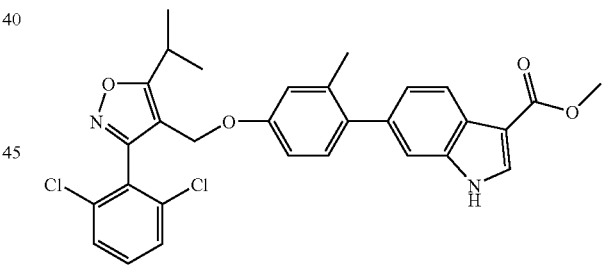

6-{4-[3-(2,6-Dichloro-phenyl-5-isopropyl-isoxazol-4-ylmethoxy]-2-methyl-phenyl}-1H-indole-3-carboxylic acid methyl ester To a mixture of [3-(2,6-dichloro-phenyl)-5-isopropyl-isoxazol-4-yl]-methanol (112 mg, 0.391 mmol) and 6-(4-hydroxy-2-methyl-phenyl)-1H-indole-3-carboxylic acid methyl ester (100 mg, 0.355 mmol) and toluene (7 mL) is added 1,1'-(azodicarbonyl)dipiperidine (99 mg, 0.39 mmol) followed by tri-n-butylphosphine (105 μL, 0.426 mmol). The mixture is allowed to stir overnight at room temperature. The reaction mixture is concentrated and purified via chromatography eluting with $CH_2Cl_2$ to give 85 mg (40%) of the title compound. ES/MS m/e 549.0 (M+1).

Step 2

6-{4-[3-(2,6-Dichloro-phenyl)-5-isopropyl-isoxazol-4-ylmethoxyl]-2-methyl-phenyl}-1H-indole-3-carboxylic acid A mixture of 6-{4-[3-(2,6-dichloro-phenyl)-5-isopropyl-isoxazol-4-ylmethoxy]-2-methyl-phenyl}-1H-indole-3-carboxylic acid methyl ester (80 mg, 0.15 mmol), 5 N sodium hydroxide (150 µL, 0.750 mmol), methanol (2 mL) and THF (1 mL) is heated at 85° C. for five hours. The mixture is cooled and 5 mL of water is added and the volatile solvents are evaporated under reduced pressure. The basic layer is washed with ether and then acidified with 1 N HCl and extracted with ether. The second ether layers are dried over anhydrous magnesium sulfate, are concentrated, and are crystallized from ether-hexane to provide 42 mg (54%) of the title compound. LC-ES/MS m/e 535.0 (M+1), 93.2% purity.

The compounds in Table 1 are prepared essentially according to the preparation of 6-{4-[3-(2,6-(dichloro-phenyl)-5-isopropyl-isoxazol-4-ylmethoxy]-2-methyl-phenyl}-1H-indole-3-carboxylic acid.

TABLE 1

| Ex | Name | Starting Material | Physical Data |
|---|---|---|---|
| 2 | 6-{4-[3-(2,6-dichloro-phenyl)-5-isopropyl-isoxazol-4-ylmethoxy]-2-methyl-phenyl}-1-methyl-1H-indole-3-carboxylic acid | [3-(2,6-dichloro-phenyl)-5-isopropyl-isoxazol-4-yl]-methanol and 6-(4-hydroxy-2-methyl-phenyl)-1-methyl-1H-indole-3-carboxylic acid methyl ester | LC-ES/MS m/e 551.0 (M + 1) |
| 3 | 6-{4-[3-(2,6-Dichloro-phenyl)-5-isopropyl-isoxazol-4-ylmethoxy]-2-methyl-phenyl}-1-methyl-1H-indole-2-carboxylic acid | [3-(2,6-dichloro-phenyl)-5-isopropyl-isoxazol-4-yl]-methanol and 6-(4-hydroxy-2-methyl-phenyl)-1-methyl-1H-indole-2-carboxylic acid methyl ester | LC-ES/MS m/e 549.0 (M + 1) |
| 4 | 6-{4-[3-(2,6-Dichloro-phenyl)-5-isopropyl-isoxazol-4-ylmethoxy]-2-methyl-phenyl}-benzo[b]thiophene-2-carboxylic acid | [3-(2,6-dichloro-phenyl)-5-isopropyl-isoxazol-4-yl]-methanol and 6-(4-hydroxy-2-methyl-phenyl)-benzo[b]thiophene-2-carboxylic acid methyl ester | LC-ES/MS m/e 552.0 (M + 1) |
| 5 | 5-{4-[5-Isopropyl-3-(2-isopropyl-phenyl)-isoxazol-4-ylmethoxy]-2-methyl-phenyl}-4-methyl-thiophene-2-carboxylic acid | [5-Isopropyl-3-(2-isopropyl-phenyl)-isoxazol-4-yl]-methanol (.060 g, .231 mmol) and 5-(4-Hydroxy-2-methyl-phenyl)-4-methyl-thiophene-2-carboxylic acid methyl ester | ES/MS m/e 490.3 (M + 1), 488.3 (M − 1) |
| 6 | 6-{4-[5-Isopropyl-3-(2-trifluoromethoxy-phenyl)-isoxazol-4-ylmethoxy]-2-methyl-phenyl}-1-methyl-1H-indole-3-carboxylic acid | [5-isopropyl-3-(2-trifluoromethoxy-phenyl)-isoxazol-4-yl]-methanol and 6-(4-hydroxy-2-methyl-phenyl)-1-methyl-1H-indole-3-carboxylic acid methyl ester | LC-ES/MS m/e 565.0 (M + 1) |
| 7 | 6-{4-[5-Cyclopropyl-3-(2-trifluoromethoxy-phenyl)-isoxazol-4-ylmethoxy]-2-methyl-phenyl}-1-methyl-1H-indole-3-carboxylic acid | 6-(4-Hydroxy-2-methyl-phenyl)-1-methyl-1H-indole-3-carboxylic acid methyl ester and [5-Cyclopropyl-3-(2-trifluoromethoxy-phenyl)-isoxazol-4-yl]-methanol | LC-ES/MS m/e 563.0 (M + 1) |
| 8 | 6-{4-[3-(2,6-Dichloro-phenyl)-5-isopropyl-isoxazol-4-ylmethoxy]-2-mtehyl-phenyl}-1-(2-methoxy-ethyl)-1H-indole-3-carboxylic acid | 6-(4-hydroxy-2-methyl-phenyl)-1-(2-methoxy-ethyl)-1H-indole-3-carboxylic acid methyl ester and [3-(2,6-dichloro-phenyl)-5-isopropyl-isoxazol-4-yl]-methanol | LC-ES/MS m/e 593.3 (M + 1) |
| 9 | 1-Butyl-6-{4-[3-(2,6-dichloro-phenyl)-5-isopropyl-isoxazol-4-ylmethoxy]-2-methyl-phenyl}-1H-indole-3-carboxylic acid | 1-butyl-6-(4-hydroxy-2-methyl-phenyl)-1H-indole-3-carboxylic acid methyl ester and [3-(2,6-dichloro-phenyl)-5-isopropyl-isoxazol-4-yl]-methanol | LC-ES/MS m/e 591.3 (M + 1) |
| 10 | 6-{4-[3-(2,6-Dichloro-phenyl)-5-isopropyl-isoxazol-4-ylmethoxy]-2-methyl-phenyl}-1-isopropyl-1H-indole-3-carboxylic acid | 6-(4-hydroxy-2-methyl-phenyl)-1-isopropyl-1H-indole-3-carboxylic acid methyl ester and [3-(2,6-dichloro-phenyl)-5-isopropyl-isoxazol-4-yl]-methanol | LC-ES/MS m/e 577.0 (M + 1) |
| 11 | 6-{4-[3-(2,6-Dichloro-phenyl)-5-isopropyl-isoxazol-4-ylmethoxy]-2-methyl-phenyl}-1-(2-methylsulfanyl-ethyl)-1H-indole-3-carboxylic acid | 6-(4-hydroxy-2-methyl-phenyl)-1-(2-methylsulfanyl-ethyl)-1H-indole-3-carboxylic acid methyl ester and [3-(2,6-dichloro-phenyl)-5-isopropyl-isoxazol-4-yl]-methanol | LC-ES/MS m/e 607.3 (M − 1) |
| 12 | 6-{4-[3-(2,6-Dichloro-phenyl)-5-isopropyl-isoxazol-4-ylmethoxy]-2-methyl-phenyl}-1-(2-dimethylamino-ethyl)-1H-indole-3-carboxylic acid hydrochloride | 1-(2-dimethylamino-ethyl)-6-(4-hydroxy-phenyl)-1H-indole-3-carboxylic acid methyl ester and [3-(2,6-dichloro-phenyl)-5-isopropyl-isoxazol-4-yl]-methanol | LC-ES/MS m/e 604.0 (M − 2) |

TABLE 1-continued

| Ex | Name | Starting Material | Physical Data |
|---|---|---|---|
| 13 | 6-{4-[3-(2,6-Dichloro-phenyl)-5-isopropyl-isoxazol-4-ylmethoxy]-2-methyl-phenyl}-benzo[b]thiophene-3-carboxylic acid | 7:3 mixture of 6-(4-hydroxy-2-methyl-phenyl)-benzo[b]thiophene-3-carboxylic acid methyl ester and 6-(4-hydroxy-2-methyl-phenyl)-benzo[b]thiophene-2-carboxylic acid methyl ester, as well as [3-(2,6-dichloro-phenyl)-5-isopropyl-isoxazol-4-yl]-methanol | LC-ES/MS m/e 550.0 (M − 1); The regioisomeric assignment is consistent with NMR evidence. |
| 14 | 6-{4-[5-Cyclopropyl-3-(2,6-dichloro-phenyl)-isoxazol-4-ylmethoxy]-2-methyl-phenyl}-benzo[b]thiophene-3-carboxylic acid | 7:3 mixture of 6-(4-hydroxy-2-methyl-phenyl)-benzo[b]thiophene-3-carboxylic acid methyl ester and 6-(4-hydroxy-2-methyl-phenyl)-benzo[b]thiophene-2-carboxylic acid methyl ester, as well as [3-(2,6-dichloro-phenyl)-5-cyclopropyl-isoxazol-4-yl]-methanol | LC-ES/MS m/e 548.0 (M − 1); The regioisomeric assignment is consistent with NMR evidence. |
| 15 | 6-{4-[5-Cyclopropyl-3-(2,6-dichloro-phenyl)-isoxazol-4-ylmethoxy]-2-methyl-phenyl}-benzo[b]thiophene-2-carboxylic acid | 7:3 mixture of 6-(4-hydroxy-2-methyl-phenyl)-benzo[b]thiophene-3-carboxylic acid methyl ester and 6-(4-hydroxy-2-methyl-phenyl)-benzo[b]thiophene-2-carboxylic acid methyl ester, as well as [3-(2,6-dichloro-phenyl)-5-cyclopropyl-isoxazol-4-yl]-methanol | LC-ES/MS m/e 548.0 (M + 1); The regioisomeric assignment is consistent with NMR evidence. |
| 16 | 6-{4-[5-Cyclopropyl-3-(2-trifluoromethoxy-phenyl)-isoxazol-4-ylmethoxy]-2-methyl-phenyl}-benzo[b]thiophene-3-carboxylic acid | 7:3 mixture of 6-(4-hydroxy-2-methyl-phenyl)-benzo[b]thiophene-3-carboxylic acid methyl ester and 6-(4-hydroxy-2-methyl-phenyl)-benzo[b]thiophene-2-carboxylic acid methyl ester, as well as [5-cyclopropyl-3-(2-trifluoromethoxy-phenyl)-isoxazol-4-yl]-methanol | LC-ES/MS m/e 566.0 (M + 1); The regioisomeric assignment is consistent with NMR evidence. |
| 17 | 6-{4-[5-Cyclopropyl-3-(2-trifluoromethoxy-phenyl)-isoxazol-4-ylmethoxy]-2-methyl-phenyl}-benzo[b]thiophene-2-carboxylic acid | 7:3 mixture of 6-(4-hydroxy-2-methyl-phenyl)-benzo[b]thiophene-3-carboxylic acid methyl ester and 6-(4-hydroxy-2-methyl-phenyl)-benzo[b]thiophene-2-carboxylic acid methyl ester, and [5-cyclopropyl-3-(2-trifluoromethoxy-phenyl)-isoxazol-4-yl]-methanol and | LC-ES/MS m/e 566.0 (M + 1) |
| 18 | 6-{4-[5-Isopropyl-3-(2-trifluoromethoxy-phenyl)-isoxazol-4-ylmethoxy]-2-methyl-phenyl}-benzo[b]thiophene-3-carboxylic acid | 7:3 mixture of 6-(4-hydroxy-2-methyl-phenyl)-benzo[b]thiophene-3-carboxylic acid methyl ester and 6-(4-hydroxy-2-methyl-phenyl)-benzo[b]thiophene-2-carboxylic acid methyl ester, as well as [5-isopropyl-3-(2-trifluoromethoxy-phenyl)-isoxazol-4-yl]-methanol | LC-ES/MS m/e 568.0 (M + 1); The regioisomeric assignment is consistent with NMR evidence. |
| 19 | 6-{4-[5-Isopropyl-3-(2-trifluoromethoxy-phenyl)-isoxazol-4-ylmethoxy]-2-methyl-phenyl}-benzo[b]thiophene-2-carboxylic acid | 6-(4-Hydroxy-2-methyl-phenyl)-benzo[b]thiophene-2-carboxylic acid methyl ester and [5-isopropyl-3-(2-trifluoromethoxy-phenyl)-isoxazol-4-yl]-methanol | LC-ES/MS m/e 568.0 (M + 1) |
| 20 | 6-{4-[5-Cyclopropyl-3-(2-trifluoromethoxy-phenyl)-isoxazol-4-ylmethoxy]-2-methyl-phenyl}-1-methyl-1H-indole-2-carboxylic acid | [5-Cyclopropyl-3-(2-trifluoromethoxy-phenyl)-isoxazol-4-yl]-methanol and 6-(4-Hydroxy-2-methyl-phenyl)-1-methyl-1H-indole-2-carboxylic acid methyl ester | LC-ES/MS m/e 563.0 (M + 1) |
| 21 | 6-{4-[5-Cyclopropyl-3-(2-trifluoromethoxy-phenyl)-isoxazol-4-ylmethoxy]-2-methyl-phenyl}-1-isopropyl-1H-indole-3-carboxylic acid | [5-Cyclopropyl-3-(2-trifluoromethoxy-phenyl)-isoxazol-4-yl]-methanol and 6-(4-Hydroxy-2-methyl-phenyl)-1-isopropyl-1H-indole-3-carboxylic acid methyl ester | ES/MS m/e 591.8 (M + 1) |

TABLE 1-continued

| Ex | Name | Starting Material | Physical Data |
|---|---|---|---|
| 22 | 6-{4-[3-(2,6-Dichloro-phenyl)-5-isopropyl-isoxazol-4-ylmethoxy]-2-methyl-phenyl}-1,2-dimethyl-1H-indole-3-carboxylic acid | [3-(2,6-Dichloro-phenyl)-5-isopropyl-isoxazol-4-yl]-methanol and 6-(4-Hydroxy-2-methyl-phenyl)-1,2-dimethyl-1H-indole-3-carboxylic acid methyl ester | ES/MS m/e 564.8 (M + 1) |
| 23 | 6-{4-[5-Cyclopropyl-3-(2,6-dichloro-phenyl)-isoxazol-4-ylmethoxy]-2-methyl-phenyl}-1,2-dimethyl-1H-indole-3-carboxylic acid | [5-Cyclopropyl-3-(2,6-dichloro-phenyl)-isoxazol-4-yl]-methanol and 6-(4-Hydroxy-2-methyl-phenyl)-1,2-dimethyl-1H-indole-3-carboxylic acid methyl ester | ES/MS m/e 560.8 (M − 1) |
| 24 | 6-{4-[5-Isopropyl-3-(2-trifluoromethoxy-phenyl)-isoxazol-4-ylmethoxy]-2-methyl-phenyl}-1,2-dimethyl-1H-indole-3-carboxylic acid | [5-Isopropyl-3-(2-trifluoromethoxy-phenyl)-isoxazol-4-yl]-methanol and 6-(4-Hydroxy-2-methyl-phenyl)-1,2-dimethyl-1H-indole-3-carboxylic acid methyl ester | ES/MS m/e 579.0 (M + 1) |
| 25 | 6-{4-[5-Cyclopropyl-3-(2-trifluoromethoxy-phenyl)-isoxazol-4-ylmethoxy]-2-methyl-phenyl}-1,2-dimethyl-1H-indole-3-carboxylic acid | [5-Cyclopropyl-3-(2-trifluoromethoxy-phenyl)-isoxazol-4-yl]-methanol and 6-(4-Hydroxy-2-methyl-phenyl)-1,2-dimethyl-1H-indole-3-carboxylic acid methyl ester | LC-ES/MS m/e 577.0 (M + 1) |
| 26 | 6-{4-[5-Cyclopropyl-3-(2,6-dichloro-phenyl)-isoxazol-4-ylmethoxy]-2-methyl-phenyl}-1-methyl-1H-indole-3-carboxylic acid | [5-Cyclopropyl-3-(2,6-dichloro-phenyl)-isoxazol-4-yl]-methanol and 6-(4-Hydroxy-2-methyl-phenyl)-1-methyl-1H-indole-3-carboxylic acid | ES/MS m/e 548.8 (M + 1) |
| 27 | (6-{4-[3-(2,6-Dichloro-phenyl)-5-isopropyl-isoxazol-4-ylmethoxy]-2-methyl-phenyl}-1-methyl-1H-indol-3-yl)-acetic acid | [3-(2,6-Dichloro-phenyl)-5-isopropyl-isoxazol-4-yl]-methanol and [6-(4-Hydroxy-2-methyl-phenyl)-1-methyl-1H-indol-3-yl]-acetic acid methyl ester | LC-ES/MS m/e 564.8 (M + 1) |
| 28 | 6-{4-[3-(2,6-Dichloro-phenyl)-5-isopropyl-isoxazol-4-ylmethoxy]-phenyl}-benzo[d]isothiazole-3-carboxylic acid | [3-(2,6-Dichloro-phenyl)-5-isopropyl-isoxazol-4-yl]-methanol and 6-(4-Hydroxy-2-methyl-phenyl)-benzo[d]isothiazole-3-carboxylic acid methyl ester | LC-ES/MS m/e 547 (M − 1) |
| 29 | 6-{4-[5-Cyclopropyl-3-(2,6-dichloro-phenyl)-isoxazol-4-ylmethoxy]-phenyl}-benzo[d]isothiazole-3-carboxylic acid | [5-Cyclopropyl-3-(2,6-dichloro-phenyl)-isoxazol-4-yl]-methanol and 6-(4-Hydroxy-2-methyl-phenyl)-benzo[d]isothiazole-3-carboxylic acid methyl ester | LC-ES/MS m/e 535 (M − 1) |
| 30 | 6-{4-[5-Cyclopropyl-3-(2-trifluoromethoxy-phenyl)-isoxazol-4-ylmethoxy]-phenyl}-benzo[d]isothiazole-3-carboxylic acid | [5-Cyclopropyl-3-(2-trifluoromethoxy-phenyl)-isoxazol-4-yl]-methanol and 6-(4-Hydroxy-2-methyl-phenyl)-benzo[d]isothiazole-3-carboxylic acid methyl ester | LC-ES/MS m/e 551 (M − 1) |
| 31 | 6-{4-[3-(2,6-Dichloro-phenyl)-5-isopropyl-isoxazol-4-ylmethoxy]-phenyl}-1-methyl-1H-indazole-3-carboxylic acid | [3-(2,6-Dichloro-phenyl)-5-isopropyl-isoxazol-4-yl]-methanol and 4-Hydroxy-2-methyl-phenyl)-1-methyl-1H-indazole-3-carboxyllic acid methyl ester | LC-ES/MS m/e 534 (M − 1) |
| 32 | 6-{4-[5-Cyclopropyl-3-(2-trifluoromethoxy-phenyl)-isoxazol-4-ylmethoxy]-phenyl}-1-methyl-1H-indazole-3-carboxylic acid | [5-Cyclopropyl-3-(2-trifluoromethoxy-phenyl)-isoxazol-4-yl]-methanol and 4-Hydroxy-2-methyl-phenyl)-1-methyl-1H-indazole-3-carboxyllic acid methyl ester | LC-ES/MS m/e 548 (M − 1) |
| 33 | 6-{4-[3-(2,6-Dichloro-phenyl)-5-isopropyl-isoxazol-4-ylmethoxy]-phenyl}-1-isopropyl-1H-indazole-3-carboxylic acid | [3-(2,6-Dichloro-phenyl)-5-isopropyl-isoxazol-4-yl]-methanol and 6-(4-Hydroxy-2-methyl-phenyl)-1-isopropyl-1H-indazole-3-carboxylic acid methyl ester | LC-ES/MS m/e 562 (M − 1) |
| 34 | 6-{4-[3-(2,6-Dichloro-phenyl)-5-isopropyl-isoxazol-4-ylmethoxy]-phenyl}-1-isopropyl-1H-indazole-3-carboxlic acid | [5-Cyclopropyl-3-(2,6-dichloro-phenyl)-isoxazol-4-yl]-methanol and 6-(4-Hydroxy-2-methyl-phenyl)-1-isopropyl-1H-indazole-3-carboxylic acid methyl ester | LC-ES/MS m/e 560 (M − 1) |

Example 35

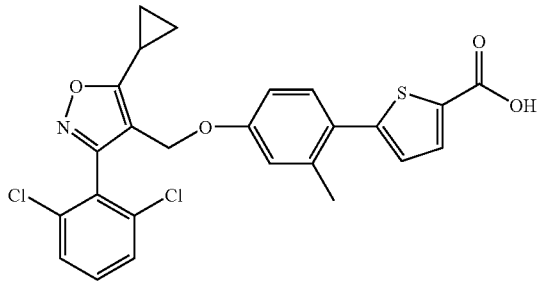

5-(4-(5-Cyclopropyl-3-(2,6-dichloro-phenyl)-isoxazol-4-ylmethoxy)-2-methyl-phenyl)-thiophene-2-carboxylic acid

Step 1

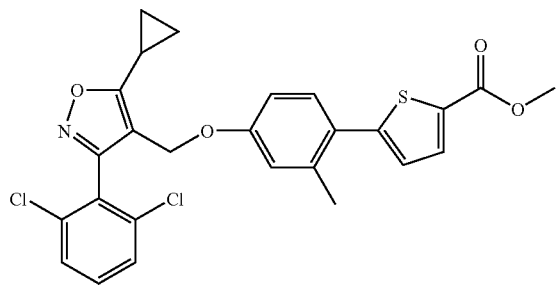

5-(4-(5-Cyclopropyl-3-(2,6-dichloro-phenyl)-isoxazol-4-ylmethoxy)-2-methyl-phenyl)-thiophene-2-carboxylic acid methyl ester To a solution of (5-cyclopropyl-3-(2,6-dichloro-phenyl)-isoxazol-4-yl)-methanol (0.188 g, 0.66 mmol), 5-(4-hydroxy-2-methyl-phenyl)-thiophene-2-carboxylic acid methyl ester (0.15 g, 0.60 mmol), and tri-N-butyl-phosphine (0.16 g, 0.79 mmol) in toluene (2 mL) is added a solution of ADDP (0.2 g, 0.79 mmol) in 1 mL of toluene. The reaction is stirred overnight. The reaction mixture is partitioned between ethyl acetate and water and the layers are separated. The organic layer is washed with brine, dried over sodium sulfate, filtered, and concentrated under reduced pressure to yield a crude oil. The oil is chromatographed using a gradient of 10% ethyl acetate in hexanes to 40% ethyl acetate in hexanes to yield the title compound (0.14 g, 41%). ES/MS m/e 514.0 (M+1).

Step 2

5-(4-(5-Cyclopropyl-3-(2,6-dichloro-phenyl)-isoxazol-4-ylmethoxy)-2-methyl-phenyl)-thiophene-2-carboxylic acid To a solution of 5-(4-(5-cyclopropyl-3-(2,6-dichloro-phenyl)-isoxazol-4-ylmethoxy)-2-methyl-phenyl)-thiophene-2-carboxylic acid methyl ester (0.138 g, 0.27 mmol) in 3 mL of methanol and 3 mL of THF is added a solution of lithium hydroxide (0.06 g, 2.7 mmol) in 3 mL of water. The reaction is heated to 55° C. for 1 hour. The solvent is evaporated to give a white solid. The solid is dissolved in aqueous 1M HCl and is extracted with ethyl acetate. The organic layer is washed with brine and dried over sodium sulfate. The reaction is filtered and concentrated under reduced pressure to yield the title compound. ES/MS m/e 500.0; 498.1 (M+1).

The compounds in Table 2 are prepared essentially according to the preparation of 5-(4-(5-Cyclopropyl-3-(2,6-dichloro-phenyl)-isoxazol-4-ylmethoxy)-2-methyl-phenyl)-thiophene-2-carboxylic acid.

TABLE 2

| Ex | Name | Starting Material | Physical Data |
|----|------|-------------------|---------------|
| 36 | 5-(4-(5-Cyclopropyl-3-(2-trifluromethoxy-phenyl)-isoxazol-4ylmethoxy)-2-methyl-phenyl)-thiophen-2-carboxylic acid | (5-Cyclopropyl-3-(2-trifluormethoxy-phenyl)-isoxazol-4yl)-methanol and 5-(4-Hydroxy-2-methyl-phenyl)-thiophene-2-carboxylic acid methyl ester | ES/MS m/e 516.0 (M + 1) |
| 37 | 2-{4-[3-(2,6-Dichloro-phenyl)-5-isopropyl-isoxazol-4-ylmethoxy]-2-methyl-phenyl} benzo[b]thiophene-5-carboxylic acid | 2-(4-Hydroxy-2-methyl-phenyl) benzo[b]thiophene-5-carboxylic acid ethyl ester and 3-(2,6-Dichloro-phenyl)-5-isopropyl-isoxazole-4-carbinol | ES/MS m/e 550 (M − 1) |
| 38 | 2-{4-[3-(2,6-Dichloro-phenyl)-5-isopropyl-isoxazol-4-ylmethoxy]-2-methyl-phenyl}-benzo[b]thiophene-7-carboxylic acid | 2-(4-Hydroxy-2-methyl-phenyl)-benzo[b]thiophene-7-carboxylic acid methyl ester | ES/MS m/e 550 (M − 1) |
| 39 | 2-{4-[5-Cyclopropyl-3-(2-trifluoromethoxy-phenyl)-isoxazol-4-ylmethoxy]-2-methyl-phenyl}-benzo[b]thiophene-5-carboxylic acid | (5-Cyclopropyl-3-(2-trifluormethoxy-phenyl)-isoxazol-4yl)-methanol and 2-(4-Hydroxy-2-methyl-phenyl)-benzo[b]thiophene-5-carboxylic acid ethyl ester | ES/MS m/e 564 (M − 1) |

Example 40

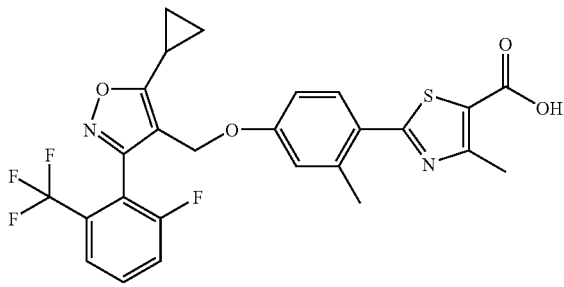

2-(4-(5-Cyclopropyl-3-(2-fluoro-6-trifluoromethyl-phenyl)-isoxazol-4-ylmethoxy)-2-methyl-phenyl)-4-methyl-thiazole-5-carboxylic acid

Step 1

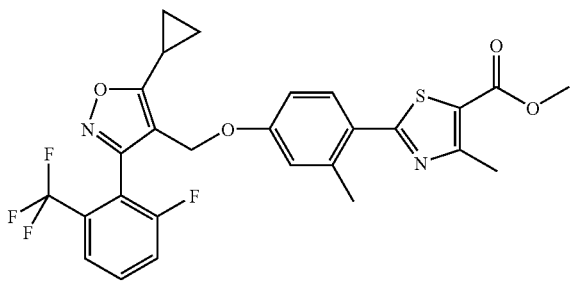

2-(4-(5-Cyclopropyl-3-(2-fluoro-6-trifluoromethyl-phenyl)-isoxazol-4-ylmethoxy)-2-methyl-phenyl)-4-methyl-thiazole-5-carboxylic acid methyl ester To a solution of 4-bromomethyl-5-cyclopropyl-3-(2-fluoro-6-trifluoromethyl-phenyl)-isoxazole (0.083 g, 0.256 mmol) and 2-(4-Hydroxy-2-methyl-phenyl)-4-methyl-thiazole-5-carboxylic acid methyl ester (0.067 g, 0.256 mmol) in 1 mL of DMF is added potassium carbonate (0.035 g, 0.256). The reaction is stirred for 60 hours. The reaction is partitioned between ethyl acetate and water. The layers are separated and the organic layer is washed with brine, dried over sodium sulfate, filtered, and concentrated under reduced pressure. The crude residue is chromatographed using a gradient of 5% ethyl acetate in hexanes to 40% ethyl acetate in hexanes to yield the title compound (0.027 g, 18%). ES/MS m/e 547.0 (M+1).

Step 2

2-(4-(5-Cyclopropyl-3-(2-fluoro-6-trifluoromethyl-phenyl)-isoxazol-4-ylmethoxy)-2-methyl-phenyl)-4-methyl-thiazole-5-carboxylic acid To a solution of 2-(4-(5-Cyclopropyl-3-(2-fluoro-6-trifluoromethyl-phenyl)-isoxazol-4-ylmethoxy)-2-methyl-phenyl)-4-methyl-thiazole-5-carboxylic acid methyl ester (0.025 g, 0.046 mmol) in 1 mL of methanol and 1 mL of THF is added a solution of LiOH (0.011 g, 0.46 mmol) in water (11 mL). The reaction is heated to 55° C. for 30 minutes. The reaction is cooled, acidified with aqueous 1M HCl, and extracted with ethyl acetate. The organic layer is washed with brine, dried over sodium sulfate, filtered, and evaporated to yield the title compound (24 mg, 99%). ES/MS m/e 533.0 (M+1).

The compounds in Table 3 are prepared essentially according to the preparation of 2-(4-(5-Cyclopropyl-3-(2-fluoro-6-trifluoromethyl-phenyl)-isoxazol-4-ylmethoxy)-2-methyl-phenyl)-4-methyl-thiazole-5-carboxylic acid.

TABLE 3

| Ex | Name | Starting Material | Physical Data |
|---|---|---|---|
| 41 | 2-(4(5-Cyclopropyl-3-(2,6-dichloro-phenyl)-isoxazol-4ylmethoxy)-2-methyl-phenyl)-4-methyl-thiazol-5-carboxylic acid | 4-Bromomethyl-5-cyclopropyl-3-(2,6-dichloro-phenyl)-isoxazole and 2-(4-Hydroxy-2-methyl-phenyl)-4-methyl-thiazole-5-carboxylic acid methyl ester | ES/MS m/e 516.3 (M + 1) |
| 42 | 5-{4-[3-(2,6-Dichloro-phenyl)-5-isopropyl-isoxazol-4-ylmethoxy]-2-methyl-phenyl}-4-methyl-thiophene-2-carboxylic acid | 4-bromomethyl-3-{2,6-dichloro-phenyl)-5-isopropyl-isoxazole in acetonitrile and 5-(4-hydroxy-2-methyl-phenyl)-4-methyl-thiophene-2-carboxylic acid methyl ester | LC-ES/MS m/e 516 (M + 1) |
| 43 | 5-{4-[3-(2,6-Dichloro-phenyl)-5-isopropyl-isoxazol-4-ylmethoxy]-2-methyl-phenyl}-thiophene-2-carboxylic acid | 4-bromomethyl-3-(2,6-dichloro-phenyl)-5-isopropyl-isoxazole in acetonitrile and 5-(4-hydroxy-2-methyl-phenyl)-thiophene-2-carboxylic acid methyl ester | LC-ES/MS 502 m/e (M + 1) |
| 44 | 5-{4-[3-(2,6-Dichloro-phenyl)-5-isopropyl-isoxazol-4-ylmethoxy]-phenyl}-thiophene-2-carboxylic acid | 4-bromomethyl-3-(2,6-dichloro-phenyl)-5-isopropyl-isoxazole in acetonitrile and 5-(4-hydroxy-phenyl)-thiophene-2-carboxylic acid methyl ester | LC-ES/MS m/e 488 (M + 1) |
| 45 | 5-{2-Chloro-4-[3-(2,6-dichloro-phenyl)-5-isopropyl-isoxazol-4-ylmethoxy]-phenyl}-4-methyl-thiophene-2-carboxylic acid | 4-bromomethyl-3-(2,6-dichloro-phenyl)-5-isopropyl-isoxazole in acetonitrile and 5-(4-hydroxy-2-chloro-phenyl)-4-methyl-thiophene-2-carboxylic acid methyl ester | LC-ES/MS m/e 538 (M + 1) |

TABLE 3-continued

| Ex | Name | Starting Material | Physical Data |
|---|---|---|---|
| 46 | 5-{4-[5-Isopropyl-3-(2-trifluoromethoxy-phenyl)-isoxazol-4-ylmethoxy]-2-methyl-phenyl}-4-methyl-thiophene-2-carboxylic acid | 4-bromomethyl-3-(2-trifluoromethoxy-phenyl)-5-isopropyl-isoxazole in acetonitrile and 5-(4-hydroxy-2-methyl-phenyl)-4-methyl-thiophene-2-carboxylic acid methyl ester | LC-ES/MS m/e 532 (M + 1) |
| 47 | 5-{4-[5-Isopropyl-3-(2-trifluoromethoxy-phenyl)-isoxazol-4-ylmethoxy]-2-methyl-phenyl}-thiophene-2-carboxylic acid | 4-bromomethyl-3-(2-trifluoromethoxy-phenyl)-5-isopropyl-isoxazole in acetonitrile and 5-(4-hydroxy-2-methyl-phenyl)-thiophene-2-carboxylic acid methyl ester | LC-ES/MS: 518 (M + 1) |
| 48 | 5-{2-Chloro-4-[5-isopropyl-3-(2-trifluoromethoxy-phenyl)-isoxazol-4-ylmethoxy]-phenyl}-thiophene-2-carboxylic acid | 4-bromomethyl-3-(2-trifluoromethoxy-phenyl)-5-isopropyl-isoxazole in acetonitrile and 5-(4-hydroxy-2-chloro-phenyl)-thiophene-2-carboxylic acid methyl ester | LC-ES/MS m/e 538 (M + 1) |
| 49 | 5-{2-Chloro-4-[5-isopropyl-3-(2-trifluoromethoxy-phenyl)-isoxazol-4-ylmethoxy]-phenyl}-4-methyl-thiophene-2-carboxylic acid | 4-bromomethyl-3-(2-trifluoromethoxy-phenyl)-5-isopropyl-isoxazole in acetonitrile and 5-(4-hydroxy-2-chloro-phenyl)-4-methyl-thiophene-2-carboxylic acid methyl ester | LC-ES/MS m/e 552 (M + 1) |
| 50 | 2-{4-[3-(2,6-Dichloro-phenyl)-5-isopropyl-isoxazol-4-ylmethoxy]-2-methyl-phenyl}-4-methyl-thiazole-5-carboxylic acid | 4-Bromomethyl-5-isopropyl-3-(2,6-dichloro-phenyl)-isoxazole and 2-(4-Hydroxy-phenyl)-4-methyl-thiazole-5-carboxylic acid ethyl ester | LC-ES/MS m/e 517 (M + 1) |
| 51 | 2-{4-[5-Isopropyl-3-(2-trifluoromethoxy-phenyl)-isoxazol-4-ylmethoxy]-2-methyl-phenyl}-4-methyl-thiazole-5-carboxylic acid | 4-Bromomethyl-5-isopropyl-3-(2-trifluoromethoxy-phenyl)-isoxazole and 2-(4-Hydroxy-phenyl)-4-methyl-thiazole-5-carboxylic acid ethyl ester | LC-ES/MS m/e 533 (M + 1) |
| 52 | 2-{4-[3-(2,6-Dichloro-phenyl)-5-isopropyl-isoxazol-4-ylmethoxy]-2-methyl-phenyl}-thiazole-5-carboxylic acid | 4-Bromomethyl-5-isopropyl-3-(2,6-dichloro-phenyl)-isoxazole and 2-(4-Hydroxy-phenyl)-thiazole-5-carboxylic acid ethyl ester | LC-ES/MS m/e 503 (M + 1) |
| 53 | 2-{4-[5-Isopropyl-3-(2-trifluoromethoxy-phenyl)-isoxazol-4-ylmethoxy]-2-methyl-phenyl}-thiazole-5-carboxylic acid | 4-Bromomethyl-5-isopropyl-3-(2-trifluoromethoxy-phenyl)-isoxazole and 2-(4-Hydroxy-phenyl)-thiazole-5-carboxylic acid ethyl ester | LC-ES/MS m/e 519 (M + 1) |
| 54 | 6-{4-[5-Isopropyl-3-(2-trifluoromethoxy-phenyl)-isoxazol-4-ylmethoxy]-2-methyl-phenyl}-nicotinic acid | 4-Bromomethyl-5-isopropyl-3-(2-trifluoromethoxy-phenyl)-isoxazole and 6-(4-Hydroxy-2-methyl-phenyl)-nicotinic acid methyl ester | LC-ES/MS m/e 513 (M + 1) |
| 55 | 5-(4-(5-Cyclopropyl-3-(2,6-dichloro-phenyl)-isoxazol-4ylmethoxy)-2-methyl-phenyl)-4-methyl-thiophene-2-carboxylic acid | 4-Bromomethyl-5-cyclopropyl-3-(2,6-dichloro-phenyl)-isoxazole and 5-(4-Hydroxy-2-methyl-phenyl)-4-methyl-thiophene-2-carboxylic acid methyl ester | ES/MS m/e 514.0 (M + 1) |
| 56 | 2-{4-[5-Cyclopropyl-3-(2,6-dichloro-phenyl)-isoxazol-4-ylmethoxy]-2-methyl-phenyl}-4-phenyl-thiazole-5-carboxylic acid | 4-bromomethyl-5-cyclopropyl-3-(2,6-dichloro-phenyl)-isoxazole and 2-(4-hydroxy-2-methyl-phenyl)-4-phenyl-thiazole-5-carboxylic acid ethyl ester | LC-ES/MS m/e 577 (M + 1) |
| 57 | 2-{4-[3-(2,6-Dichloro-phenyl)-5-isopropyl-isoxazol-4-ylmethoxy]-2-methyl-phenyl}-4-phenyl-thiazole-5-carboxylic acid | 4-bromomethyl-3-(2,6-dichloro-phenyl)-5-isopropyl-isoxazole and 2-(4-hydroxy-2-methyl-phenyl)-4-phenyl-thiazole-5-carboxylic acid ethyl ester | LC-ES/MS m/e 579 (M + 1) |
| 58 | 2-{4-[5-Cyclopropyl-3-(2,6-dichloro-phenyl)-isoxazol-4-ylmethoxy]-2-methyl-phenyl}-4-propyl-thiazole-5-carboxylic acid | 4-bromomethyl-5-cyclopropyl-3-(2,6-dichloro-phenyl)-isoxazole and 2-(4-hydroxy-2-methyl-phenyl)-4-propyl-thiazole-5-carboxylic acid ethyl ester | LC-ES/MS m/e 543 (M + 1) |
| 59 | 2-{4-[5-Cyclopropyl-3-(2,6-dichloro-phenyl)-isoxazol-4-ylmethoxy]-2-methyl-phenyl}-4-isopropyl-thiazole-5-carboxylic acid | 4-bromomethyl-5-cyclopropyl-3-(2,6-dichloro-phenyl)-isoxazole and 2-(4-hydroxy-2-methyl-phenyl)-4-isopropyl-thiazole-5-carboxylic acid ethyl ester | LC-ES/MS m/e 543 (M + 1) |

TABLE 3-continued

| Ex | Name | Starting Material | Physical Data |
|---|---|---|---|
| 60 | 2-{4-[5-Cyclopropyl-3-(2-trifluoromethoxy-phenyl)-isoxazol-4-ylmethoxy]-2-methyl-phenyl}-4-isopropyl-thiazole-5-carboxylic acid | 4-bromomethyl-5-cyclopropyl-3-(2-trifluoromethoxy-phenyl)-isoxazole and 2-(4-hydroxy-2-methyl-phenyl)-4-isopropyl-thiazole-5-carboxylic acid ethyl ester | LC-ES/MS m/e 559 (M + 1) |
| 61 | 4-Isopropyl-2-{4-[5-isopropyl-3-(2-trifluoromethoxy-phenyl)-isoxazol-4-ylmethoxy]-2-methyl-phenyl}-thiazole-5-carboxylic acid | 4-bromomethyl-5-isopropyl-3-(2-trifluoromethoxy-phenyl)-isoxazole and 2-(4-hydroxy-2-methyl-phenyl)-4-isopropyl-thiazole-5-carboxylic acid ethyl ester | LC-ES/MS m/e 561 (M + 1) |
| 62 | 2-{4-[3-(2,6-Dichloro-phenyl)-5-isopropyl-isoxazol-4-ylmethoxy]-2-methyl-phenyl}-4-trifluoromethyl-thiazole-5-carboxylic acid | 4-bromomethyl-3-(2,6-dichloro-phenyl)-5-isopropyl-isoxazole and 2-(4-hydroxy-2-methyl-phenyl)-4-trifluoromethyl-thiazole-5-carboxylic acid ethyl ester | LC-ES/MS m/e 571 (M + 1) |
| 63 | 2-{4-[3-(2,6-Dichloro-phenyl)-5-isopropyl-isoxazol-4-ylmethoxy]-2-methyl-phenyl}-thiazole-4-carboxylic acid | 4-bromomethyl-3-(2,6-dichloro-phenyl)-5-isopropyl-isoxazole and 2-(4-hydroxy-2-methyl-phenyl)-thiazole-4-carboxylic acid ethyl ester | LC-ES/MS m/e 503 (M + 1) |
| 64 | 2-{4-[5-Cyclopropyl-3-(2,6-dichloro-phenyl)-isoxazol-4-ylmethoxy]-2-methyl-phenyl}-5-isopropyl-thiazole-4-carboxylic acid | 4-bromomethyl-5-cyclopropyl-3-(2,6-dichloro-phenyl)-isoxazole and 2-(4-hydroxy-2-methyl-phenyl)-5-isopropyl-thiazole-4-carboxylic acid ethyl ester | LC-ES/MS m/e 543 (M + 1) |
| 65 | 2-{4-[5-Cyclopropyl-3-(2-trifluoromethoxy-phenyl)-isoxazol-4-ylmethoxy]-2-methyl-phenyl}-5-isopropyl-thiazole-4-carboxylic acid | 4-bromomethyl-5-cyclopropyl-3-(2-trifluoromethoxy-phenyl)-isoxazole and 2-(4-hydroxy-2-methyl-phenyl)-5-isopropyl-thiazole-4-carboxylic acid ethyl ester | LC-ES/MS m/e 559 (M + 1) |
| 66 | 5-Isopropyl-2-{4-[5-isopropyl-3-(2-trifluoromethoxy-phenyl)-isoxazol-4-ylmethoxy]-2-methyl-phenyl}-thiazole-4-carboxylic acid | 4-bromomethyl-5-isopropyl-3-(2-trifluoromethoxy-phenyl)-isoxazole and 2-(4-hydroxy-2-methyl-phenyl)-5-isopropyl-thiazole-4-carboxylic acid ethyl ester | LC-ES/MS m/e 561 (M + 1) |
| 67 | 6-{4-[3-(2,6-Dichloro-phenyl)-5-isopropyl-isoxazol-4-ylmethoxy]-2-methyl-phenyl}-benzofuran-3-carboxylic acid | 4-bromomethyl-3-(2,6-dichloro-phenyl)-5-isopropyl-isoxazole and 6-(4-Hydroxy-2-methyl-phenyl)-benzofuran-3-carboxylic acid ethyl ester | LC-ES/MS m/e 534.2 (M − 1) |
| 68 | 6-{4-[3-(2,6-Dichloro-phenyl)-5-cyclopropyl-isoxazol-4-ylmethoxy]-2-methyl-phenyl}-benzofuran-3-carboxylic acid | 4-bromomethyl-5-cyclopropyl-3-(2,6-dichloro-phenyl)-isoxazole and 6-(4-Hydroxy-2-methyl-phenyl)-benzofuran-3-carboxylic acid ethyl ester | LC-ES/MS m/e 532.0 (M − 1) |
| 69 | 6-{4-[5-Isopropyl-3-(2-trifluoromethoxy-phenyl)-isoxazol-4-ylmethoxy]-2-methyl-phenyl}-benzofuran-3-carboxylic acid | 4-bromomethyl-5-isopropyl-3-(2-trifluoromethoxy-phenyl)-isoxazole and 6-(4-Hydroxy-2-methyl-phenyl)-benzofuran-3-carboxylic acid ethyl ester | LC-ES/MS m/e 550.0 (M − 1) |
| 70 | 6-{4-[3-(2,6-Dichloro-phenyl)-5-isopropyl-isoxazol-4-ylmethoxy]-2-methyl-phenyl}-2-methyl-benzofuran-3-carboxylic acid | 4-bromomethyl-3-(2,6-dichloro-phenyl)-5-isopropyl-isoxazole and 6-(4-Hydroxy-2-methyl-phenyl)-2-methyl-benzofuran-3-carboxylic acid methyl ester | LC-ES/MS m/e 550.0 (M − 1) |
| 71 | (6-{4-[3-(2,6-Dichloro-phenyl)-5-isopropyl-isoxazol-4-ylmethoxy]-2-methyl-phenyl}-benzo[b]thiophen-2-yl)-acetic acid | 4-bromomethyl-3-(2,6-dichloro-phenyl)-5-isopropyl-isoxazole and [6-(4-Hydroxy-2-methyl-phenyl)-benzo[b]thiophen-2-yl]-acetic acid methyl ester | LC-ES/MS m/e 567.8 (M + 1) |
| 72 | 6-{4-[5-Cyclopropyl-3-(2,6-dichloro-phenyl)-isoxazol-4-ylmethoxy]-2-methyl-phenyl}-benzo[d]isoxazole-3-carboxylic acid | 4-bromomethyl-5-cyclopropyl-3-(2,6-dichloro-phenyl)-isoxazole and 6-(4-Hydroxy-2-methyl-phenyl)-benzo[d]isoxazole-3-carboxylic acid ethyl ester | LC-ES/MS m/e 536.8 (M + 1) |
| 73 | 6-{4-[5-Isopropyl-3-(2-trifluoromethoxy-phenyl)-isoxazol-4-ylmethoxy]-2-methyl-phenyl}-benzo[d]isoxazole-3-carboxylic acid | 4-bromomethyl-5-isopropyl-3-(2-trifluoromethoxy-phenyl)-isoxazole and 6-(4-Hydroxy-2-methyl-phenyl)-benzo[d]isoxazole-3-carboxylic acid ethyl ester | LC-ES/MS m/e 552.8 |

TABLE 3-continued

| Ex | Name | Starting Material | Physical Data |
|---|---|---|---|
| 74 | 5-{4-[3-(2,6-Dichloro-phenyl)-5-isopropyl-isoxazol-4-ylmethoxy]-2-methyl-phenyl}-benzofuran-2-carboxylic acid | 4-bromomethyl-3-(2,6-dichloro-phenyl)-5-isopropyl-isoxazole and 5-(4-Hydroxy-2-methyl-phenyl)-benzofuran-2-carboxylic acid ethyl ester | LC-ES/MS m/e 534.0 (M − 1) |

Example 75

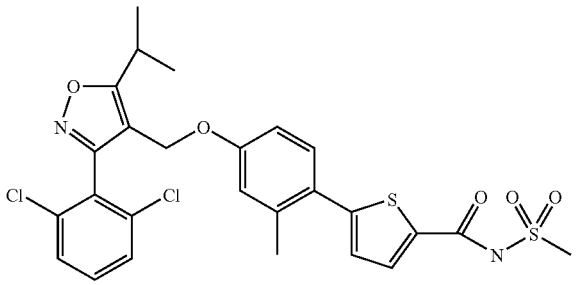

N-(5-{4-[3-(2,6-Dichloro-phenyl)-5-isopropyl-isoxazol-4-ylmethoxy]-2-methyl-phenyl}-thiophene-2-carbonyl)-methanesulfonamide A mixture of 5-{4-[3-(2,6-dichloro-phenyl)-5-isopropyl-isoxazol-4-ylmethoxy]-2-methyl-phenyl}-thiophene-2-carboxylic acid (250 mg, 0.5 mmol), 1-[3-(dimethylamino) propyl]-3-ethylcarbodiimide hydrochloride (144 mg, 0.75 mmol), N,N'-dimethylamino pyridine (122 mg, 1.0 mmol) and methanesulfonamide (57 mg, 0.6 mmol) in dichloromethane (20 mL) is stirred at ambient temperature overnight. The reaction mixture is diluted with dichloromethane and washed with 1N HCl. The organic phase is concentrated under reduced pressure and purified by column chromatography (gradient: 0 to 20% EtOAc in hexanes with 0.1% AcOH) to give the title compound (160 mg, 55%). LC-ES/MS m/e 579 (M+1), 100%.

The compounds in Table 4 are prepared essentially according to the preparation of N-(5-{4-[3-(2,6-dichloro-phenyl)-5-isopropyl-isoxazol-4-ylmethoxy]-2-ethyl-phenyl}-thiophene-2-carbonyl)-methanesulfonamide.

TABLE 4

| Ex | Name | Starting Material | Physical Data |
|---|---|---|---|
| 76 | Ethanesulfonic acid (5-{4-[3-(2,6-dichloro-phenyl)-5-isopropyl-isoxazol-4-ylmethoxy]-2-methyl-phenyl}-thiophene-2-carbonyl)-amide | 5-{4-[3-(2,6-dichloro-phenyl)-5-isopropyl-isoxazol-4-ylmethoxy]-2-methyl-phenyl}-thiophene-2-carboxylic acid and ethanesulfonamide | LC-ES/MS m/e 593 (M + 1) |
| 77 | Propane-1-sulfonic acid (5-{4-[3-(2,6-dichloro-phenyl)-5-isopropyl-isoxazol-4-ylmethoxy]-2-methyl-phenyl}-thiophene-2-carbonyl)-amide | 5-{4-[3-(2,6-dichloro-phenyl)-5-isopropyl-isoxazol-4-ylmethoxy]-2-methyl-phenyl}-thiophene-2-carboxylic acid and n-propanesulfonamide | LC-ES/MS m/e 607 (M + 1) |
| 78 | Propane-2-sulfonic acid (5-{4-[3-(2,6-dichloro-phenyl)-5-isopropyl-isoxazol-4-ylmethoxy]-2-methyl-phenyl}-thiophene-2-carbonyl)-amide | 5-{4-[3-(2,6-dichloro-phenyl)-5-isopropyl-isoxazol-4-ylmethoxy]-2-methyl-phenyl}-thiophene-2-carboxylic acid and iso-propanesulfonamide | LC-ES/MS m/e 607 (M + 1) |
| 79 | 2-Methyl-propane-2-sulfonic acid (5-{4-[3-(2,6-dichloro-phenyl)-5-isopropyl-isoxazol-4-ylmethoxy]-2-methyl-phenyl}-thiophene-2-carbonyl)-amide | 5-{4-[3-(2,6-dichloro-phenyl)-5-isopropyl-isoxazol-4-ylmethoxy]-2-methyl-phenyl}-thiophene-2-carboxylic acid and t-butylsulfonamide | LC-ES/MS m/e 621 (M + 1) |
| 80 | N-(5-{4-[3-(2,6-Dichloro-phenyl)-5-isopropyl-isoxazol-4-ylmethoxy]-2-methyl-phenyl}-thiophene-2-carbonyl)-benzenesulfonamide | 5-{4-[3-(2,6-dichloro-phenyl)-5-isopropyl-isoxazol-4-ylmethoxy]-2-methyl-phenyl}-thiophene-2-carboxylic acid and benzene sulfonamide | LC-ES/MS m/e 641 (M + 1) |
| 81 | N-(5-{4-[3-(2,6-Dichloro-phenyl)-5-isopropyl-isoxazol-4-ylmethoxy]-2-methyl-phenyl}-thiophene-2-carbonyl)-2-methyl-benzenesulfonamide | 5-{4-[3-(2,6-dichloro-phenyl)-5-isopropyl-isoxazol-4-ylmethoxy]-2-methyl-phenyl}-thiophene-2-carboxylic acid and o-methylbenzene sulfonamide | LC-ES/MS m/e 655 (M + 1) |
| 82 | N-(5-{4-[3-(2,6,Dichloro-phenyl)-5-isopropyl-isoxazol-4-ylmethoxy]-2-methyl-phenyl}-thiophene-2-carbonyl)-4-methyl-benzenesulfonamide | 5-{4-[3-(2,6-dichloro-phenyl)-5-isopropyl-isoxazol-4-ylmethoxy]-2-methyl-phenyl}-thiophene-2-carboxylic acid and p-methylbenzene sulfonamide | LC-ES/MS m/e 655 (M + 1), |

Example 83

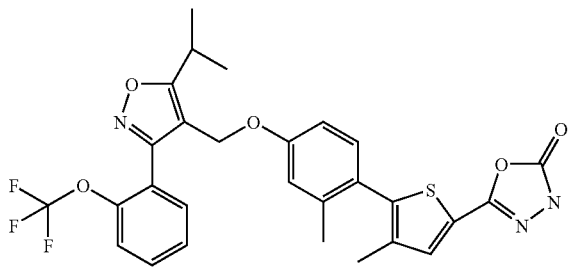

5-(5-{4-[5-Isopropyl-3-(2-trifluoromethoxy-phenyl)-isoxazol-4-ylmethoxy]-2-methyl-phenyl}-4-methyl-thiophen-2-yl)-3H-[3,4]oxadiazol-2-one

Step 1

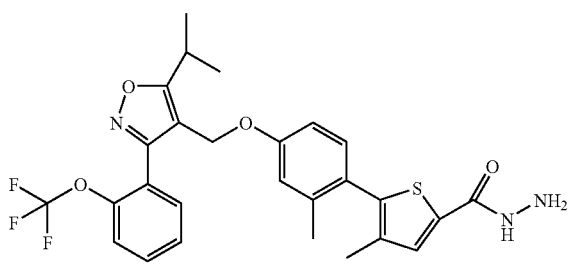

5-{4-[5-Isopropyl-3-(2-trifluoromethoxy-phenyl)-isoxazol-4-ylmethoxy]-2-methyl-phenyl}-4-methyl-thiophene-2-carboxylic acid hydrazide

Step A

To a solution of 5-{4-[5-isopropyl-3-(2-trifluoromethoxy-phenyl)-isoxazol-4-ylmethoxy]-2-methyl-phenyl}-4-methyl-thiophene-2-carboxylic acid methyl ester (980 mg, 1.8 mmol) in EtOH (7 mL) is added hydrazine hydrate (5 mL) and the mixture is stirred at 80° C. overnight. The reaction mixture is concentrated under reduced pressure. The residue is partitioned between EtOAc and water. The layers are separated and the organic phase is concentrated under reduced pressure to give 5-{4-[5-isopropyl-3-(2-trifluoromethoxy-phenyl)-isoxazol-4-ylmethoxy]-2-methyl-phenyl}-4-methyl-thiophene-2-carboxylic acid hydrazide (890 mg, 90%) as a light yellow foam. LC-ES/MS m/e 546 (M+1), 100%.

Step B

A mixture of 5-{4-[5-isopropyl-3-(2-trifluoromethoxy-phenyl)-isoxazol-4-ylmethoxy]-2-methyl-phenyl}-4-methyl-thiophene-2-carboxylic acid hydrazide (382 mg, 0.7 mmol), 1,1'-carbonyl-diimidazole (170 mg, 1.05 mmol) and Et$_3$N (0.2 mL, 1.4 mmol) in THF (7 mL) is stirred at reflux overnight. The reaction mixture is diluted with EtOAc and washed with 1N HCl. The organic phase is concentrated under reduced pressure and purified by column chromatography (gradient: 0 to 20% EtOAc in hexanes with 0.1% AcOH) to give the title compound (340 mg, 85%). LC-ES/MS m/e 572 (M+1), 100%.

Example 84

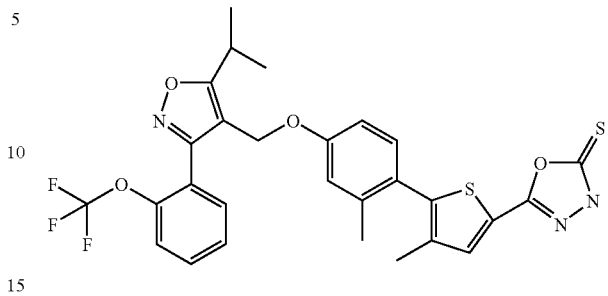

5-(5-{4-[5-Isopropyl-3-(2-trifluoromethoxy-phenyl-isoxazol-4-ylmethoxy]-2-methyl-phenyl}-4-methyl-thiophen-2-yl)-3H-[1,3,4]oxadiazole-2-thione A mixture of 5-{4-[5-isopropyl-3-(2-trifluoromethoxy-phenyl)-isoxazol-4-ylmethoxy]-2-methyl-phenyl}-4-methyl-thiophene-2-carboxylic acid hydrazide (382 mg, 0.7 mmol), carbon disulfide (0.11 mL, 1.75 mmol) and KOH (43.2 mg, 0.77 mmol) in MeOH (10 mL) is stirred at 80° C. overnight. The reaction mixture is concentrated under reduced pressure and the residue is partitioned between EtOAc and 1N HCl. The layers are separated and the organic phase is concentrated under reduced pressure. The residue is purified by column chromatography (gradient: 0 to 20% EtOAc in hexanes with 0.1% AcOH) to give the title compound (393 mg, 96%). LC-ES/MS m/e 588 (M+1), 95.4%.

Example 85

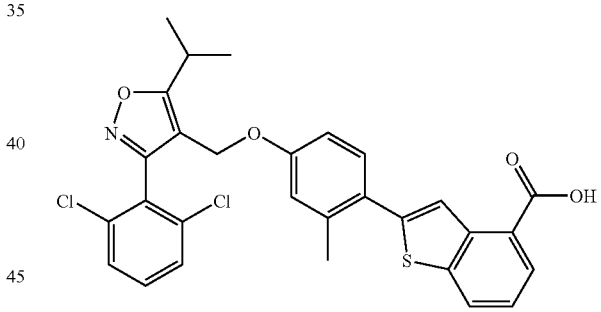

2-{4-[3-(2,6-Dichloro-phenyl)-5-isopropyl-isoxazol-4-ylmethoxy]-2-methyl-phenyl}-benzo[b]thiophene-4-carboxylic acid To a 60° C. suspension of 4-(4-Bromo-3-methyl-phenoxymethyl)-3-(2,6-dichloro-phenyl)-5-isopropyl-isoxazole (0.90 mmol; 410 mg) in a 2M solution of sodium carbonate (7.20 mmol; 3.6 mL) and 1.5 mL of deoxygenated dioxane under a nitrogen atmosphere is slowly added a solution of 4-carboxy-benzo[b]thiophen-2-boronic acid (1.08=mol; 240 mg) in 3.5 mL of deoxygenated dioxane over 1 h via an addition pump. The mixture is stirred for 1 h. The organic solvent is removed under reduced pressure and the residue is acidified with 1N HCl to pH 4. The resulting solution is extracted with dichloromethane. The organic layers are combined, dried over anhydrous sodium sulfate, filtered, and concentrated under reduced pressure. The residue is chromatographed using a gradient from 100% dichloromethane to 100% ethyl acetate to obtain a solid which is washed with acetonitrile to yield the title compound (135 mg, 27%) as a white solid.

Example 86

2-{4-[3-(2,6-Dichloro-phenyl)-5-isopropyl-isoxazol-4-ylmethoxy]-2-methyl-phenyl}-benzo[b]thiophene-6-carboxylic acid

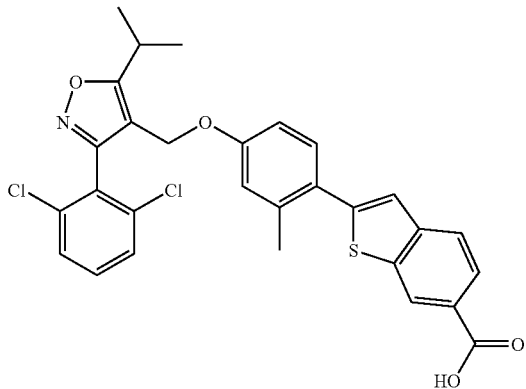

The title compound is prepared essentially according to the preparation of 2-{4-[3-(2,6-dichloro-phenyl)-5-isopropyl-isoxazol-4-ylmethoxy]-2-methyl-phenyl}-benzo[b]thiophene-4-carboxylic acid utilizing 6-carboxy-benzo[b]thiophen-2-boronic acid. ES/MS m/e 550 (M−1).

Example 87

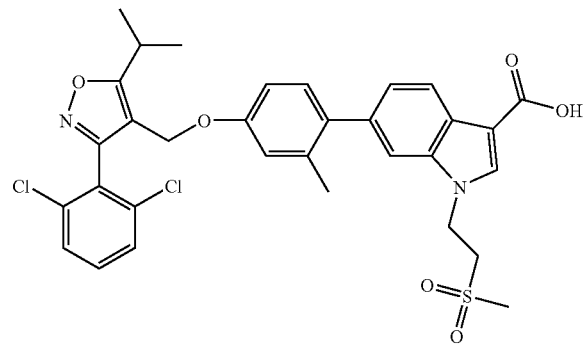

6-{4-[3-(2,6-Dichloro-phenyl)-5-isopropyl-isoxazol-4-ylmethoxy]-2-methyl-phenyl}-1-(2-methanesulfonyl-ethyl)-1H-indole-3-carboxylic acid

Step 1

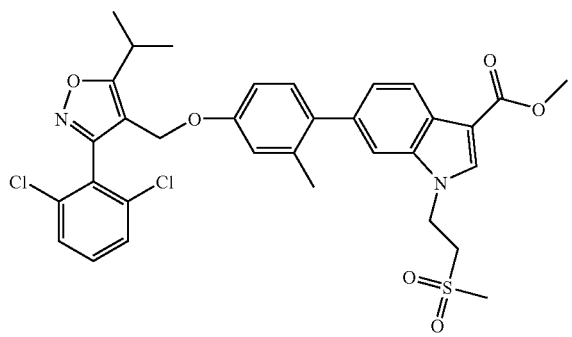

6-{4-[3-(2,6-Dichloro-phenyl)-5-isopropyl-isoxazol-4-ylmethoxy]-2-methyl-phenyl}-1-(2-methanesulfonyl-ethyl)-1H-indole-3-carboxylic acid methyl ester Solid 4-methylmorpholine N-oxide (151 mg, 1.29 mmol) is added to a mixture of 6-(4-hydroxy-2-methyl-phenyl)-1-(2-methylsulfanyl-ethyl)-1H-indole-3-carboxylic acid methyl ester (268 mg, 0.429 mmol) in acetone (4.9 mL0 and water (1.7 mL), followed by the dropwise addition of osmium tetroxide (21 µL of a 2.5 wt % solution in 2-methyl-2-propanol, 15 mol %). The mixture is stirred overnight at room temperature and is quenched with saturated aqueous sodium bisulfite solution (10 mL). The mixture is extracted repeatedly with $CH_2Cl_2$. The combined $CH_2Cl_2$ layers are washed with brine and dried ($MgSO_4$). The residue is purified using flash chromatography (gradient: 20 to 50% ethyl acetate/heptane) to provide the title compound (240 mg. 85%). ES/MS m/e 657.0 (M+2).

Step 2

6-{4-[3-(2,6-Dichloro-phenyl)-5-isopropyl-isoxazol-4-ylmethoxy]-2-methyl-phenyl}-1-(2-methanesulfonyl-ethyl)-1H-indole-3-carboxylic acid A mixture of 6-{4-[3-(2,6-dichloro-phenyl)-5-isopropyl-isoxazol-4-ylmethoxy]-2-methyl-phenyl}-1-(2-methanesulfonyl-ethyl)-1H-indole-3-carboxylic acid methyl ester (235 mg, 0.358 mmol), methanol (17 mL), THF (8 mL), and 5 N sodium hydroxide (1.29 mL) is heated at reflux for two days. The mixture is allowed to cool and is concentrated under reduced pressure to near dryness. Approximately 10 mL of water is added and the mixture is stirred for two hours. The mixture is filtered and the solid is washed with water and dried to provide the title compound (187 mg, 81%). LCMS (ES+): (641.0).

Example 88

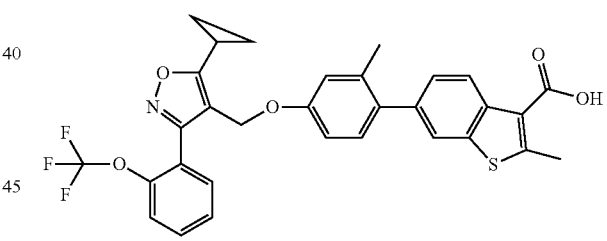

6-{4-[5-Cyclopropyl-3-(2-trifluoromethoxy-phenyl)-isoxazol-4-ylmethoxy]-2-methyl-phenyl}-2-methyl-benzo[b]thiophene-3-carboxylic acid A solution of diisopropylamine (120 µL, 0.849 mmol) and THF (4 mL) is cooled to −78° C. A solution of n-butyl lithium (1.6 M in hexanes, 487 µL, 0.779 mmol) is added dropwise and the reaction is stirred for 40 minutes at −78° C. A solution of 6-{4-[5-cyclopropyl-3-(2-trifluoromethoxy-phenyl)-isoxazol-4-ylmethoxy]-2-methyl-phenyl}-benzo[b]thiophene-3-carboxylic acid (200 mg, 0.354 mmol) in THF (2 mL) is added dropwise and the resulting yellow solution is stirred at −78° C. for one hour. Methyl iodide (221 µL, 3.54 mmol) is added dropwise and the reaction is allowed to gradually warm to ambient temperature overnight. The flask is cooled in an ice bath and saturated aqueous ammonium chloride (5 mL) is added. The mixture is diluted with water and ethyl acetate. The ethyl acetate layer is washed with brine, dried over $MgSO_4$, and concentrated under reduced pressure. The residue is purified via radial chromatography eluting with 2%

MeOH—CH₂Cl₂. The purification is repeated for impure fractions containing product. The title compound (44 mg, 21%) is obtained as a gray solid.

Example 89

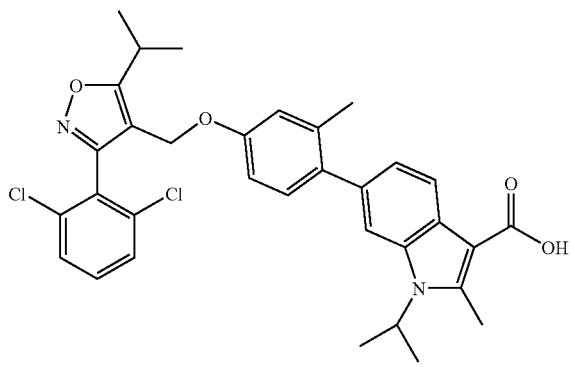

6-{4-[3-(2,6-Dichloro-1-phenyl)-5-isopropyl-4-yl-isoxazol-4-ylmethoxy]-2-methoxy-phenyl}-1-isopropyl-2-methyl-1H-indole-3-carboxylic acid Step 1

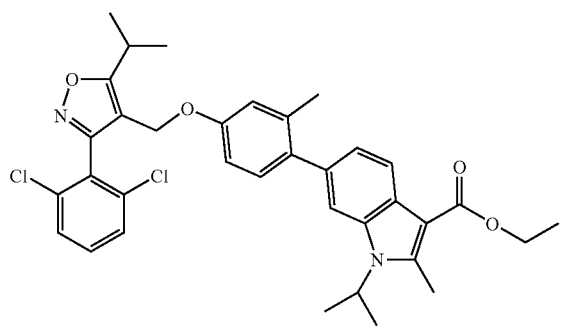

6-{4-[3-(2,6-Dichloro-phenyl)-5-isopropyl-isoxazol-4-ylmethoxy]-2-methoxy-phenyl}-1-isopropyl-2-methyl-1H-indole-3-carboxylic acid ethyl ester

[3-(2,6-Dichloro-phenyl)-5-isopropyl-isoxazol-4-yl]-methanol (0.2 g, 0.71 mmol), 1-isopropyl-6-(4-hydroxy-2-methyl-phenyl)-2-methyl-1H-indole-3-carboxylic acid methyl ester (0.2 g, 0.59 mmol), tri-n-butylphosphine (0.14 g, 0.71 mmol) and azodicarboxylic acid dipiperidide (0.18 g, 0.71 mmol) are stirred in dry toluene (9 mL) for 2 days at room temperature. The reaction is diluted with hexane (9 mL), stirred for 30 minutes, and filtered. The filtrate is concentrated and the residue purified via flash chromatography (40 g SiO₂) eluting with 30% THF in heptane to afford the title compound (124 mg, 34.6%). ES/MS m/e 606.8 (M+1)

Step 2

6-{4-[3-(2,6-Dichloro-phenyl)-5-isopropyl-isoxazol-4-ylmethoxy]-2-methyl-phenyl}-1-isopropyl-2-methyl-1H-indole-3-carboxylic acid A mixture of 6-{4-[3-(2,6-dichloro-phenyl)-5-isopropyl-isoxazol-4-ylmethoxy]-2-methyl-phenyl}-1-isopropyl-2-methyl-1H-indole-3-carboxylic acid methyl ester (239 mg, 0.390 mmol), sodium hydroxide (5 M, 0.5 mL) and methanol (1 mL) is heated in a microwave reactor utilizing the lowest power setting at 125° C. for 20 minutes. The mixture is acidified with 1 N HCl and extracted with ether. The ether layers are washed with brine, dried over MgSO₄, and concentrated under reduced pressure. The residue is purified on a via radial chromatography (2 mm plate, 3% MeOH—CH₂Cl₂) to yield the title compound (59 mg, 25%) as a white solid. ES/MS m/e 592.8 (M+1)

The compounds in Table 5 are prepared essentially according to the preparation of 6-{4-[3-(2,6-Dichloro-phenyl)-5-isopropyl-isoxazol-4-ylmethoxy]-2-methyl-phenyl}-1-isopropyl-2-methyl-1H-indole-3-carboxylic acid.

TABLE 5

| Ex | Name | Starting Material | Physical Data |
|---|---|---|---|
| 90 | 1-Cyclopropyl-6-{4-[5-isopropyl-3-(2-trifluoromethoxy-phenyl)-isoxazol-4-ylmethoxy]-2-methyl-phenyl}-5-methoxy-2-methyl-1H-indole-3-carboxylic acid | [5-Isopropyl-3-(2-trifluoromethoxy-phenyl)-isoxazol-4-yl]-methanol and 1-Cyclopropyl-6-(4-hydroxy-2-methyl-phenyl)-5-methoxy-2-methyl-1H-indole-3-carboxylic acid | LC-ES/MS m/e 635.2 (M + 1) |
| 91 | 1-Cyclopropyl-6-{4-[3-(2,6-dichloro-phenyl)-5-isopropyl-isoxazol-4-ylmethoxy]-2-methyl-phenyl}-5-methoxy-2-methyl-1H-indole-3-carboxylic acid | [3-(2,6-Dichloro-phenyl)-5-isopropyl-isoxazol-4-yl]-methanol and 1-Cyclopropyl-6-(4-hydroxy-2-methyl-phenyl)-5-methoxy-2-methyl-1H-indole-3-carboxylic acid | ES/MS m/e 620.8 (M + 1) |
| 92 | 6-{4-[5-Cyclopropyl-3-(2-trifluoromethoxy-phenyl)-isoxazol-4-ylmethoxy]-2-methyl-phenyl}-1-isopropyl-2-methyl-1H-indole-3-carboxylic acid | 5-Cyclopropyl-3-(2-fluoromethoxy-phenyl)-isoxazol-4-yl]-methanol and 6-(4-Hydroxy-2-ethyl-phenyl)-1-isopropyl-2-methyl-1H-indole-3-carboxylic acid | ES/MS m/e 605.8 (M + 1) |

TABLE 5-continued

| Ex | Name | Starting Material | Physical Data |
| --- | --- | --- | --- |
| 93 | 1-Cyclopropyl-6-{4-[5-cyclopropyl-3-(2-trifluoromethoxy-phenyl)-isoxazol-4-ylmethoxy]-2-methyl-phenyl}-5-methoxy-2-methyl-1H-indole-3-carboxylic acid | [5-cyclopropyl-3-(2-trifluoromethoxy-phenyl)-isoxazol-4-yl]-methanol and 1-cyclopropyl-6-(4-hydroxy-2-methyl-phenyl)-5-methoxy-2-methyl-1H-indole-3-carboxylic acid ethyl ester. | ES/MS m/e 633.8 (M + 1) |

Example 94

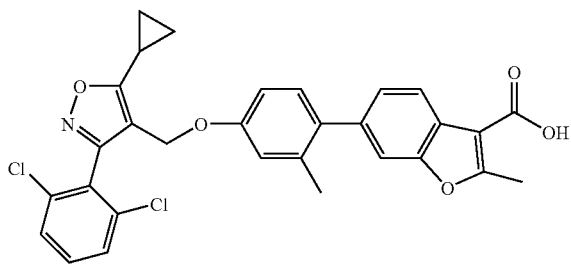

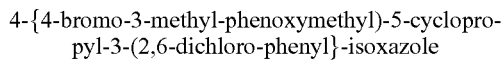
6-{4-[3-(2,6-Dichloro-phenyl)-5-cyclopropyl-isoxazol-4-ylmethoxy]-2-methyl-phenyl}-2-methyl-benzofuran-3-carboxylic acid Step 1

4-{4-bromo-3-methyl-phenoxymethyl)-5-cyclopropyl-3-(2,6-dichloro-phenyl}-isoxazole A solution of 4-bromo-3-methyl-phenol (143 mg, 0.764 mmol) and 4-bromomethyl-5-cyclopropyl-3-(2,6-dichloro-phenyl)-isoxazole (221 mg, 0.636 mmol) in dimethylformamide (1 mL) is treated with potassium carbonate (89 mg, 0.637-mmol). The reaction mixture is heated to 80° C. for 60 minutes and cooled to room temperature. The mixture is loaded directly onto a silica gel column and purified by flash chromatography eluting with 15% EtOAc/Hexanes. The fractions are combined to provide the title compound (0.26 g, 92%). LC-MS: (M+1);

Step 2

6-{4-[5-cyclopropyl-3-(2,6-dichloro-phenyl)-isoxazol-4-ylmethoxy]-2-methyl-phenyl}-2-methyl-benzofuran-3-carboxylic acid methyl ester A solution of 2-methyl-6-(4,4,5,5-tetramethyl-[1,3,2]dioxaborolan-2-yl)-benzofuran-3-carboxylic acid methyl ester (0.145 g, 0.459 mmol) and 4-(4-bromo-3-methyl-phenoxymethyl)-5-cyclopropyl-3-(2,6-dichloro-phenyl)-isoxazole (229 mg, 0.504 mmol) in toluene (5 mL) is evacuated and refilled with N₂ three times. Pd(OAc)₂ (10 mg), 2-dicyclohexylphosphino-2,6-dimethoxy-1,1'-biphenyl (38 mg) and potassium phosphate, tribasic, N-hydrate (195 mg) in water (0.5 mL) are added. The resulting mixture is evacuated and refilled with N₂ three times and stirred at 110° C. for 16 hours. The mixture is cooled to room temperature and filtered through a pad of diatomaceous earth. The filtrate is concentrated to a residue. The residue is purified via silica gel chromatography eluting with 25% EtOAc/Hexanes to provide the title compound (0.14 g, 55%). ¹H NMR (400 MHz, CDCl₃): 7.90 (d, 1H), 7.39 (d, 1H), 7.37 (s, 1H), 7.31-7.29 (m, 2H), 7.18 (d, 1H), 7.10 (d, 1H), 6.70-6.66 (m, 2H), 4.80 (s, 2H), 3.94 (s, 3H), 2.76 (s, 3H), 2.18 (s, 3H), 2.17 (m, 1H), 1.29-1.25 (m, 2H), 1.15-1.11 (m, 2H).

Step 3

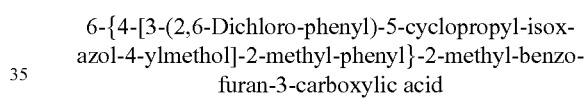
6-{4-[3-(2,6-Dichloro-phenyl)-5-cyclopropyl-isoxazol-4-ylmethol]-2-methyl-phenyl}-2-methyl-benzofuran-3-carboxylic acid A solution of 6-{4-[5-cyclopropyl-3-(2,6-dichloro-phenyl)-isoxazol-4-ylmethoxy]-2-methyl-phenyl}-2-methyl-benzofuran-3-carboxylic acid methyl ester (0.142 g, 0.252 mmol) in tetrahydrofuran (1 mL) and methanol (1 mL) is treated with sodium hydroxide (1 mL). The reaction mixture is stirred at 100° C. for 4 hours and cooled to room temperature. The mixture is neutralized with HCl (1.0N, 1.0 mL) and concentrated to a residue. The aqueous residue is extracted with EtOAc (10 mL×2). The combined organic layers are dried over Na₂SO₄, filtered, and concentrated. The crude product is purified by flash chromatography eluting with 25%-50% EtOAc/Hexanes. The appropriate fractions are combined and concentrated under reduced pressure to afford the title compound. LC-ES/MS m/e 546.0 (M−1)

The compounds in Table 6 are prepared essentially according to the preparation of 6-{4-[3-(2,6-Dichloro-phenyl)-5-cyclopropyl-isoxazol-4-ylmethoxy]-2-methyl-phenyl}-2-methyl-benzofuran-3-carboxylic acid.

TABLE 6

| Ex | Name | Starting Material | Physical Data |
| --- | --- | --- | --- |
| 95 | 6-{4-[5-Isopropyl-3-(2-trifluoromethoxy-phenyl)-isoxazol-4-ylmethoxy]-2-methyl-phenyl}-2-methyl-benzofuran-3-carboxylic acid | 4-bromomethyl-5-isopropyl-3-(2-trifluoromethoxy-phenyl)-isoxazole, 4-Bromo-3-methyl-phenol, and 2-Methyl-6-(4,4,5,5-tetramethyl-[1,3,2]dioxaborolan-2-yl)-benzofuran-3-carboxylic acid methyl ester | LC-ES/MS m/e 564.2 (M − 1) |

TABLE 6-continued

| Ex | Name | Starting Material | Physical Data |
|---|---|---|---|
| 96 | 6-{4-[5-cyclopropyl-3-(2-trifluoromethoxy-phenyl)-isoxazol-4-ylmethoxy]-2-methyl-phenyl}-2-methyl-benzofuran-3-carboxylic acid | 4-bromomethyl-5-cyclopropyl-3-(2-trifluoromethoxy-phenyl)-isoxazole, 4-Bromo-3-methyl-phenol, and 2-Methyl-6-(4,4,5,5-tetramethyl-[1,3,2]dioxaborolan-2-yl)-benzofuran-3-carboxylic acid methyl ester | LC-ES/MS m/e 562.2 (M − 1) |
| 97 | (6-{4-[3-(2,6-Dichloro-phenyl)-5-isopropyl-isoxazol-4-ylmethoxy]-2-methyl-phenyl}-benzo[b]thiophen-3-yl)-acetic acid | 4-bromomethyl-3-(2,6-dichloro-phenyl)-5-isopropyl-isoxazole, 4-Bromo-3-methyl-phenol, and [6-(4,4,5,5-Tetramethyl-[1,3,2]dioxaborolan-2-yl)-benzo[b]thiophen-3-yl]-acetic acid methyl ester | LC-ES/MS m/e 565.8 (M − 1) |
| 98 | (6-{4-[5-Cyclopropyl-3-(2,6-dichloro-phenyl)-isoxazol-4-ylmethoxy]-2-methyl-phenyl}-benzo[b]thiophen-3-yl)-acetic acid | 4-Bromomethyl-5-cyclopropyl-3-(2,6-dichloro-phenyl)-isoxazole, 4-Bromo-3-methyl-phenol, and [6-(4,4,5,5-Tetramethyl-[1,3,2]dioxaborolan-2-yl)-benzo[b]thiophen-3-yl]-acetic acid methyl ester | LC-ES/MS m/e 564.0 (M − 1) |
| 99 | (6-{4-[5-Cyclopropyl-3-(2-trifluoromethoxy-phenyl)-isoxazol-4-ylmethoxy]-2-methyl-phenyl}-benzo[b]thiophen-3-yl)-acetic acid | 4-bromomethyl-5-cyclopropyl-3-(2-trifluoromethoxy-phenyl)-isoxazole, 4-Bromo-3-methyl-phenol, and [6-(4,4,5,5-Tetramethyl-[1,3,2]dioxaborolan-2-yl)-benzo[b]thiophen-3-yl]-acetic acid methyl ester | LC-ES/MS m/e 577.8 (M − 1) |

Example 100

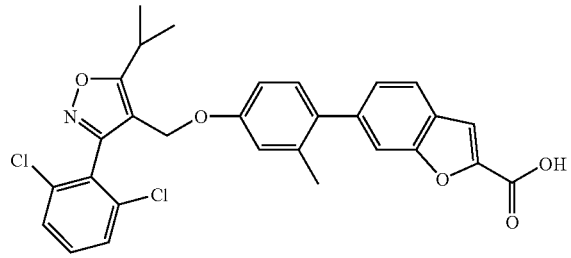

6-{4-[3-(2,6-Dichloro-phenyl)-5-isopropyl-isoxazol-4-ylmethoxy]-2-methyl-phenyl}-benzofuran-2-carboxylic acid Step 1

6-{4-[3-(2,6-dichloro-phenyl-5-isopropyl-isoxazol-4-ylmethoxy]-2-methyl-phenyl}-benzofuran-2-carboxylic acid tert-butyl ester A solution of 6-(4-hydroxy-2-methyl-phenyl)-benzofuran-3-carboxylic acid tert-butyl ester (85 mg, 0.26 mmol) and 4-bromomethyl-3-(2,6-dichloro-phenyl)-5-isopropyl-isoxazole (110 mg, 0.31 mmol) in DMF (1.0 mL) is treated with potassium carbonate (72 mg, 0.52 mmol). The reaction mixture is stirred at 90° C. for 60 minutes and cooled to room temperature. The mixture is loaded onto a silica gel column and rinsed with 20% EtOAc/Hexanes to afford the title compound (124 mg, 80%). LC-ES/MS m/e 593.7 (M+1);

Step 2

6-{4-[3-(2-Dichloro-phenyl)-5-isopropyl-isoxazol-4-ylmethoxy]-2-methyl-phenyl}-benzofuran-2-carboxylic acid To a solution of 6-{4-[3-(2,6-dichloro-phenyl)-5-isopropyl-isoxazol-4-ylmethoxy]-2-methyl-phenyl}-benzofuran-2-carboxylic acid tert-butyl ester (65 mg, 0.011 mmol) in dichloromethane (1.0 mL) is added TFA (1.0 mL). The mixture is stirred at room temperature for 60 minutes and concentrated under reduced pressure. The residue is purified by silica gel chromatography eluting with EtOAc to provide the title compound (32 mg, 54%). LC-ES/MS m/e 537.8 (M+1).

Example 101

6-{4-[5-Cyclopropyl-3-(2-trifluoromethoxy-phenyl)-isoxazol-4-ylmethoxy]-2-methyl-phenyl}-benzo[b]thiophene-3-carboxylic acid

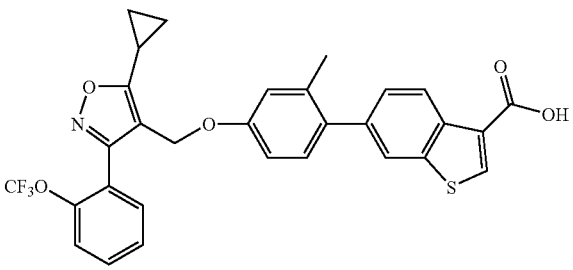

6-{4-[5-Cyclopropyl-3-(2-trifluoromethoxy-phenyl)-isoxazol-4-ylmethoxy]-2-methyl-phenyl}-benzo[b]thiophene-3-carboxylic acid

Step 1

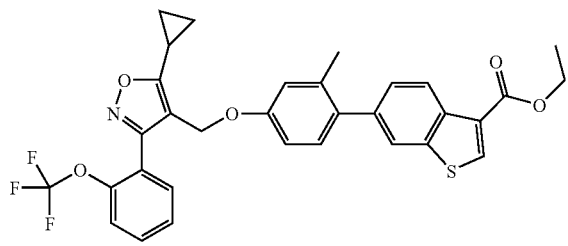

6-{4-[5-Cyclopropyl-3-(2-trifluoromethoxy-phenyl)-isoxazol-4-ylmethoxy]-2-methoxy-phenyl}-benzo[b]thiophene-3-carboxylic acid ethyl ester A solution water (850 mL), potassium carbonate (212.08 g, 1.5345 mol, 3 eq), dioxane (500 mL), 6-bromo-benzo[b]thiophene-3-carboxylic acid ethyl ester (175 g, 0.6138 mol, 1.2 eq) and tetrakis(triphenylphosphine)palladium (35.47 g, 0.03 mol, 0.06 eq) is heated to reflux (87-90° C.). A solution of crude 5-cyclopropyl-4-[3-methyl-4-(4,4,5,5-tetramethyl-[1,3,2]dioxaborolan-2-yl)-phenoxymethyl]-3-(2-trifluoromethoxy-phenyl)-isoxazole (0.5115 mol, 1 eq) in dioxane (1 L) is added over a period of 1 hour. The reaction mixture is stirred for 2 h at reflux. Upon completion of the reaction, the reaction mixture is cooled to room temperature. The combined reaction mixture is poured onto a mixture of brine (5 L) and EtOAc (3 L) with stirring. The organic layer is separated and washed with brine (3 L). The combined aqueous layers are extracted with EtOAc (2 L). The organic layer is separated and washed again with brine (2 L). The organic layers are combined, dried over magnesium sulfate, filtered, and concentrated under reduced pressure. The residue is dried under vacuum to afford a yellow oil (737 g).

The oil (737 g) is dissolved in EtOAc (500 mL). Heptane is added until the solution becomes hazy and the oil is separated (~3 L). The resulting hazy solution is stirred for 1 h. The suspension is filtered and the filter cake is washed with heptane (200 mL). The combined filtrate is purified via column chromatography on silica gel columns (2×1.5 Kg) eluting with EtOAc (5 to 20%) in heptane. The appropriate fractions are combined and concentrated under reduced pressure to afford a pale yellow oil (401 g). The impure product fractions are concentrated (~200 g of oil) and the silica gel purification is repeated using 2 Kg of silica gel. The appropriate fractions are combined and concentrated to afford the title compound as a thick pale yellow oil (496 g, 99%).

$^1$H NMR (DMSO-d6, 300 MHz): δ 8.66 (s, 1H), 7.67-7.60 (m, 2H), 7.54-7.48 (m, 2H), 7.42 (dd, 1H, J=3, 8.4), 7.12 (d, 1H, J=8.4), 6.8-6.7 (m, 2H), 4.93 (s, 2H), 4.35 (q, 2H, J=7.2), 2.39 (m, 1H), 2.17 (s, 3H), 1.34 (t, 3H, J=7.3), 1.2-1.08 (m, 4H).

Step 2

6-{4-[5-Cyclopropyl-3-(2-trifluoromethoxy-phenyl)-isoxazol-4-ylmethoxy]-2-methyl-phenyl}-benzo[b]thiophene-3-carboxylic acid Solution A: A solution of 6-{4-[5-cyclopropyl-3-(2-trifluoromethoxy-phenyl)-isoxazol-4-ylmethoxy]-2-methyl-phenyl}-benzo[b]thiophene-3-carboxylic acid ethyl ester (470 g) in EtOH (1.8 L) is heated to 40° C.

Solution B: In a separate flask is added 50% NaOH (158.6 g, 1.9825 mol, 2.5 eq) in water (125 mL) and EtOH (600 mL).

Solution B is added via addition funnel to Solution A at 40-50° C. at a such a rate to prevent formation of significant amount of solids. Upon completion of the addition, the reaction mixture is heated to 65-75° C. and stirred at this temperature for 1 h. Upon completing of the reaction, the reaction mixture is cooled to room temperature. The reaction mixture is diluted with water (3 L), EtOAc (2.5 L), and 10% aqueous citric acid solution (3 L). The layers are separated and the aqueous layer is extracted with EtOAc (2 L). The combined organic layer is washed with brine (3 L), dried over magnesium sulfate, filtered, and concentrated to afford a pale yellow oil (480 g). The oil is co-evaporated with EtOH (1 L) and dissolved (510 g) in MeOH (1.2 L).

A solution of crude title compound in MeOH is added dropwise over 3 h to water (8 L) with stirring. The resulting suspension is stirred for additional 2 h at room temperature. The solids are collected by filtration, washed with water (2 L), and dried in a vacuum oven at 40° C.

The wet title compound (530 g) is added portionwise to MeOH (1.2 L) at 50-60° C. The resulting suspension is heated to reflux (64° C.) and stirred at this temperature for 1 h. The suspension is cooled to 0-5° C. and stirred at this temperature for 1 h. The solids are collected by filtration and washed with cold MeOH (200 mL, −20° C.). The product is dried in a vacuum oven at 40° C. to afford the title compound as a white powder (354 g, 78.9%). HPLC: 99.5 area %. Elemental Analysis for $C_{30}H_{22}F_3NO_5S$: Theory: 63.71% C, 3.92% H, 2.48% N. Found: 63.10% C, 3.83% H, 2.51% N. This procedure affords crystalline Form II: melt onset 151.22° C. $^1$H NMR (DMSO-d6, 300 MHz): δ 12.93 (s, 1H), 8.61 (s, 1H), 8.49 (d, 1H, J=8.4), 7.97 (m, 1H), 7.7-7.6 (m, 2H), 7.58-7.49 (m, 2H), 7.40 (dd, 1H, J=1.8, 8.4), 7.13 (d, 1H, J=8.4), 6.82-6.72 (m, 2H), 4.93 (s, 2H), 2.40 (m, 1H), 2.18 (s, 3H), 1.2-1.18 (m, 4H).

XRD patterns are collected from 4 to 40 degrees in 2-theta using a CuK source (λ=1.54056 Angstroms)) and a source power of 40 kV and 50 mA.

Form II XRD

| Angle 2-Theta ° | d value (Angstrom) | Intensity (%) |
| --- | --- | --- |
| 6.914 | 12.77 | 29.1 |
| 8.305 | 10.64 | 19.6 |
| 9.901 | 8.93 | 11.2 |
| 10.778 | 8.20 | 8.8 |
| 12.067 | 7.33 | 35.9 |
| 12.233 | 7.23 | 39.7 |
| 13.845 | 6.39 | 14.6 |
| 14.104 | 6.27 | 100.0 |
| 16.521 | 5.36 | 50.0 |
| 16.848 | 5.26 | 19.0 |
| 17.065 | 5.19 | 33.1 |
| 17.976 | 4.93 | 33.2 |
| 18.514 | 4.79 | 31.7 |

Form II XRD

| Angle 2-Theta ° | d value (Angstrom) | Intensity (%) |
| --- | --- | --- |
| 18.920 | 4.69 | 17.8 |
| 19.307 | 4.59 | 28.9 |
| 19.838 | 4.47 | 11.2 |
| 20.113 | 4.41 | 41.2 |
| 20.807 | 4.27 | 96.4 |
| 21.775 | 4.08 | 21.0 |
| 22.769 | 3.90 | 13.6 |
| 23.169 | 3.84 | 61.5 |
| 23.694 | 3.75 | 9.2 |
| 24.311 | 3.66 | 9.6 |
| 25.025 | 3.56 | 7.9 |
| 26.038 | 3.42 | 29.3 |
| 28.358 | 3.14 | 18.1 |
| 30.490 | 2.93 | 17.7 |
| 30.818 | 2.90 | 8.3 |

Form I Procedure. The title compound (400 mg) is mixed with MeOH (15 mL) and heated to approximately 64° C. Water is added (4-5 mL) dropwise until right before the point where a solution could not be achieved anymore with heating. The solution is allowed to cool to ambient temp with slow stirring. The solids are filtered, washed with water, and suction-dried to afford the title compound (365 mg, 91%) as a crystalline Form I: melt onset 124.54° C.

Form I XRD

| Angle 2-Theta ° | d value (Angstrom) | Intensity (%) |
| --- | --- | --- |
| 8.759 | 10.09 | 56.0 |
| 10.087 | 8.76 | 11.1 |
| 10.343 | 8.55 | 36.4 |
| 10.476 | 8.44 | 100.0 |
| 12.837 | 6.89 | 24.5 |
| 13.246 | 6.68 | 56.7 |
| 13.588 | 6.51 | 99.5 |
| 14.091 | 6.28 | 75.1 |
| 14.449 | 6.13 | 74.1 |
| 15.559 | 5.69 | 73.5 |
| 15.848 | 5.59 | 22.7 |
| 16.324 | 5.43 | 43.5 |
| 17.579 | 5.04 | 19.9 |
| 18.490 | 4.79 | 19.4 |
| 18.899 | 4.69 | 26.6 |
| 19.169 | 4.63 | 60.9 |
| 19.323 | 4.59 | 44.3 |
| 19.969 | 4.44 | 25.8 |
| 20.767 | 4.27 | 13.9 |
| 21.040 | 4.22 | 40.5 |
| 21.444 | 4.14 | 12.3 |
| 22.989 | 3.87 | 25.8 |
| 23.410 | 3.80 | 81.9 |
| 23.998 | 3.71 | 29.0 |
| 25.416 | 3.50 | 27.2 |
| 25.552 | 3.48 | 55.4 |
| 27.373 | 3.26 | 24.5 |
| 28.411 | 3.14 | 19.5 |

We claim:

1. A compound of formula

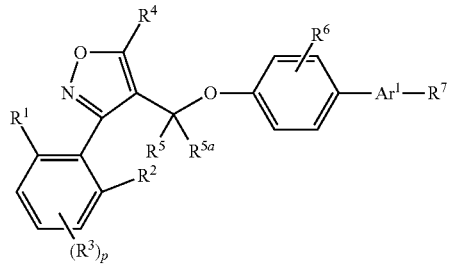

p is 0 or 1;

$R^1$ and $R^2$ are independently selected from the group consisting of hydrogen, —$C_1$-$C_6$ alkyl, —$C_1$-$C_6$ haloalkyl, —$C_1$-$C_6$ alkoxy-, —$C_1$-$C_6$ haloalkoxy-, halo, —$SR^{11}$, and —S—$C_1$-$C_3$ haloalkyl;

each $R^3$ is independently selected from the group consisting of —$C_1$-$C_6$ alkyl, —$C_1$-$C_6$ haloalkyl, —$C_1$-$C_6$ alkoxy-, —$C_1$-$C_6$ haloalkoxy-, and halo;

$R^4$ is selected from the group consisting of hydrogen, —$C_1$-$C_6$ alkyl, —$C_1$-$C_6$ haloalkyl, —$C_3$-$C_8$ cycloalkyl, —$C_4$-$C_8$ alkylcycloalkyl, —$C_1$-$C_6$ alkoxy-, and —$C_1$-$C_6$ haloalkoxy-;

$R^5$ and $R^{5a}$ are independently selected from the group consisting of hydrogen, and —$C_1$-$C_3$ alkyl;

$R^6$ is selected from the group consisting of hydrogen, —$C_1$-$C_6$ alkyl, —$C_1$-$C_6$ haloalkyl, and halo;

$Ar^1$ is selected from the group consisting of indolyl, pyridinyl, thienyl, benzothienyl, indazolyl, benzothiazolyl, benzoisoxazolyl, benzofuranyl, and thiazolyl, each optionally substituted with one or two groups independently selected from the group consisting of hydroxy, —$C_1$-$C_6$ alkyl, $C_3$-$C_8$ cycloalkyl, —$C_1$-$C_4$ alkyl$SO_2C_1$-$C_2$ alkyl, —$C_1$-$C_4$ alkyl$SC_1$-$C_2$ alkyl, —$C_1$-$C_4$ alkyl$NR^{10}R^{11}$, phenyl, —$C_1$-$C_4$ alkyl-O—$C_1$-$C_4$ alkyl, and —$NHC(O)R^{10}$;

$R^7$ is selected from the group consisting of —$CH_2COOR^{10}$, —$COOR^{10}$, —$CONR^{11}R^{11}$, —$C(O)NHSO_2C_1$-$C_4$ alkyl, —$C(O)NHSO_2R^{12}$, oxadiazolethione, and oxadiazolone;

each $R^{10}$ is independently selected from the group consisting of hydrogen, —$C_1$-$C_4$ alkyl, and phenyl;

each $R^{11}$ is independently hydrogen, or —$C_1$-$C_6$ alkyl;

$R^{12}$ is —$C_1$-$C_6$ alkyl or phenyl optionally substituted with —$C_1$-$C_3$ alkyl, or a pharmaceutically acceptable salt thereof.

2. A compound according to claim 1 wherein p is 0 or 1;

$R^1$ and $R^2$ are independently selected from the group consisting of hydrogen, fluoro, chloro, $CF_3$, and $OCF_3$, $R^3$ is fluoro, chloro, $CF_3$, $SCF_3$, or $OCF_3$;

$R^4$ is H, isopropyl or cyclopropyl;

$R^5$ and $R^{5a}$ are each independently selected from H or methyl;

$Ar^1$ is indolyl, pyridinyl, thienyl, thiazolyl and benzothienyl each optionally substituted with a group selected from the group consisting of $C_1$-$C_4$ alkyl, $CF_3$, —$CH_2CH_2SCH_2$, —$CH_2CH_2OCH_3$, —$CH_2CH_2SO_2CH_3$, —$CH_2CH_2N(CH_3)_2$, and phenyl;

$R^6$ is hydrogen, or methyl;

R⁷ is —COOH, —COOC₁-C₂ alkyl, —CONHSO₂C₁-C₄ alkyl, —CONHSO₂-phenyl, —CONHSO₂-phenylmethyl, oxadiazolone, and thiadiazolone;
each R¹⁰ is independently hydrogen or C₁-C₆ alkyl;
each R¹¹ is independently hydrogen or C₁-C₆ alkyl; and
R¹² is phenyl, or a pharmaceutically acceptable salt thereof.

3. A compound of claim 1, wherein each p is 0; R¹ and R² are independently selected from the group consisting of chloro, fluoro, trifluoromethyl, and trifluoromethoxy-; R⁴ is isopropyl or cyclopropyl; R⁵ and R⁵ᵃ are both hydrogen; R⁶ is hydrogen, methyl, ethyl or chloro; Ar¹ is thienyl, benzothienyl, indolyl or thiazolyl, each optionally substituted with a group selected from methyl, ethyl, propyl, butyl, isopropyl, cyclopropyl, —CH₂CH₂SO₂CH₃, —CH₂CH₂N(CH₃)₂, —CH₂CH₂SCH₂, CH₂CH₂OCH₂, and phenyl; and R⁷ is COOH, or a pharmaceutically acceptable salt thereof.

4. A compound selected from the group consisting of:
6-{4-[5-Isopropyl-3-(2-trifluoromethoxy-phenyl)-isoxazol-4-ylmethoxy]-2-methyl-phenyl}-1-methyl-1H-indole-3-carboxylic acid,
6-{4-[5-Cyclopropyl-3-(2-trifluoromethoxy-phenyl)-isoxazol-4-ylmethoxy]-2-methyl-phenyl}-1-methyl-1H-indole-3-carboxylic acid,
6-{4-[5-Cyclopropyl-3-(2,6-dichloro-phenyl)-isoxazol-4-ylmethoxy]-2-methyl-phenyl}-benzo[b]thiophene-3-carboxylic acid,
6-{4-[5-Cyclopropyl-3-(2-trifluoromethoxy-phenyl)-isoxazol-4-ylmethoxy]-2-methyl-phenyl}-benzo[b]thiophene-3-carboxylic acid,
6-{4-[5-Isopropyl-3-(2-trifluoromethoxy-phenyl)-isoxazol-4-ylmethoxy]-2-methyl-phenyl}-benzo[b]thiophene-3-carboxylic acid,
6-{4-[3-(2,6-dichloro-phenyl)-5-isopropyl-isoxazol-4-ylmethoxy]-2-methyl-phenyl}-1-methyl-1H-indole-3-carboxylic acid,
6-{4-[3-(2,6-Dichloro-phenyl)-5-isopropyl-isoxazol-4-ylmethoxy]-phenyl}-1-isopropyl-1H-indole-3-carboxylic acid,
6-{4-[3-(2,6-Dichloro-phenyl)-5-isopropyl-isoxazol-4-ylmethoxy]-2-methyl-phenyl}-benzo[b]thiophene-3-carboxylic acid,
6-{4-[5-Cyclopropyl-3-(2,6-dichloro-phenyl)-isoxazol-4-ylmethoxy]-2-methyl-phenyl}-benzo[b]thiophene-3-carboxylic acid,
6-{4-[5-Cyclopropyl-3-(2-trifluoromethoxy-phenyl)-isoxazol-4-ylmethoxy]-2-methyl-phenyl}-benzo[b]thiophene-3-carboxylic acid,
6-{4-[5-Isopropyl-3-(2-trifluoromethoxy-phenyl)-isoxazol-4-ylmethoxy]-2-methyl-phenyl}-benzo[b]thiophene-3-carboxylic acid,
6-{4-[5-Cyclopropyl-3-(2-trifluoromethoxy-phenyl)-isoxazol-4-ylmethoxy]-2-methyl-phenyl}-1-isopropyl-1H-indole-3-carboxylic acid,
6-{4-[3-(2,6-Dichloro-phenyl)-5-isopropyl-isoxazol-4-ylmethoxy]-2-methyl-phenyl}-1,2-dimethyl-1H-indole-3-carboxylic acid,
6-{4-[5-Cyclopropyl-3-(2-trifluoromethoxy-phenyl)-isoxazol-4-ylmethoxy]-2-methyl-phenyl}-1,2-dimethyl-1H-indole-3-carboxylic acid,
6-{4-[5-Cyclopropyl-3-(2,6-dichloro-phenyl)-isoxazol-4-ylmethoxy]-2-methyl-phenyl}-1-methyl-1H-indole-3-carboxylic acid,
6-{4-[3-(2,6-Dichloro-phenyl)-5-isopropyl-isoxazol-4-ylmethoxy]-phenyl}-benzo[d]isothiazole-3-carboxylic acid,
6-{4-[5-Cyclopropyl-3-(2,6-dichloro-phenyl)-isoxazol-4-ylmethoxy]-phenyl}-benzo[d]isothiazole-3-carboxylic acid,
6-{4-[5-Cyclopropyl-3-(2-trifluoromethoxy-phenyl)-isoxazol-4-ylmethoxy]-phenyl}-benzo[d]isothiazole-3-carboxylic acid,
6-{4-[3-(2,6-Dichloro-phenyl)-5-isopropyl-isoxazol-4-ylmethoxy]-phenyl}-1-methyl-1H-indazole-3-carboxylic acid,
6-{4-[5-Cyclopropyl-3-(2-trifluoromethoxy-phenyl)-isoxazol-4-ylmethoxy]-phenyl}-1-methyl-1H-indazole-3-carboxylic acid,
6-{4-[3-(2,6-Dichloro-phenyl)-5-isopropyl-isoxazol-4-ylmethoxy]-phenyl}-1-isopropyl-1H-indazole-3-carboxylic acid,
6-{4-[3-(2,6-Dichloro-phenyl)-5-isopropyl-isoxazol-4-ylmethoxy]-phenyl}-1-isopropyl-1H-indazole-3-carboxylic acid,
5-(4-(5-Cyclopropyl-3-(2,6-dichloro-phenyl)-isoxazol-4-ylmethoxy)-2-methyl-phenyl)-thiophene-2-carboxylic acid,
5-(4-(5-Cyclopropyl-3-(2-trifluoromethoxy-phenyl)-isoxazol-4-ylmethoxy)-2-methyl-phenyl)-thiophen-2-carboxylic acid,
2-(4-(5-Cyclopropyl-3-(2-fluoro-6-trifluoromethyl-phenyl)-isoxazol-4-ylmethoxy)-2-methyl-phenyl)-4-methyl-thiazole-5-carboxylic acid,
2-(4-(5-Cyclopropyl-3-(2,6-dichloro-phenyl)-isoxazol-4-ylmethoxy)-2-methyl-phenyl)-4-methyl-thiazol-5-carboxylic acid,
5-{4-[3-(2,6-Dichloro-phenyl)-5-isopropyl-isoxazol-4-ylmethoxy]-2-methyl-phenyl}-4-methyl-thiophene-2-carboxylic acid,
2-{4-[5-Isopropyl-3-(2-trifluoromethoxy-phenyl)-isoxazol-4-ylmethoxy]-2-methyl-phenyl}-4-methyl-thiazole-5-carboxylic acid,
2-{4-[5-Isopropyl-3-(2-trifluoromethoxy-phenyl)-isoxazol-4-ylmethoxy]-2-methyl-phenyl}-thiazole-5-carboxylic acid,
5-(4-(5-Cyclopropyl-3-(2,6-dichloro-phenyl)-isoxazol-4-ylmethoxy)-2-methyl-phenyl)-4-methyl-thiophene-2-carboxylic acid,
2-{4-[5-Cyclopropyl-3-(2,6-dichloro-phenyl)-isoxazol-4-ylmethoxy]-2-methyl-phenyl}-4-isopropyl-thiazole-5-carboxylic acid,
6-{4-[3-(2,6-Dichloro-phenyl)-5-isopropyl-isoxazol-4-ylmethoxy]-2-methyl-phenyl}-2-methyl-benzofuran-3-carboxylic acid,
6-{4-[5-Cyclopropyl-3-(2,6-dichloro-phenyl)-isoxazol-4-ylmethoxy]-2-methyl-phenyl}-benzo[d]isoxazole-3-carboxylic acid,
6-{4-[5-Cyclopropyl-3-(2-trifluoromethoxy-phenyl)-isoxazol-4-ylmethoxy]-2-methyl-phenyl}-2-methyl-benzo[b]thiophene-3-carboxylic acid,
6-{4-[3-(2,6-Dichloro-phenyl)-5-isopropyl-isoxazol-4-ylmethoxy]-2-methyl-phenyl}-1-isopropyl-2-methyl-1H-indole-3-carboxylic acid, and
6-{4-[5-cyclopropyl-3-(2-trifluoromethoxy-phenyl)-isoxazol-4-ylmethoxy]-2-methyl-phenyl}-2-methyl-benzofuran-3-carboxylic acid, or a pharmaceutically acceptable salt thereof.

5. The compound 6-{4-[5-Cyclopropyl-3-(2-trifluoromethoxy-phenyl)-isoxazol-4-ylmethoxy]-2-methyl-phenyl}-benzo[b]thiophene-3-carboxylic acid

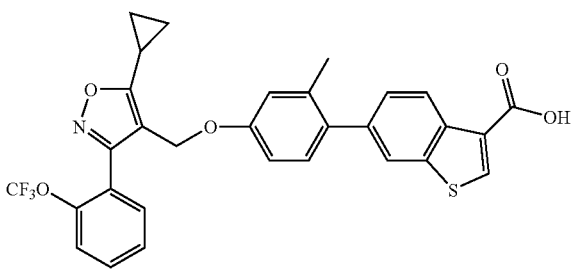

or a pharmaceutically acceptable salt thereof.

6. The compound 6-{4-[5-Cyclopropyl-3-(2-trifluoromethoxy-phenyl)-isoxazol-4-ylmethoxy]-phenyl}-benzo[d]isothiazole-3-carboxylic acid

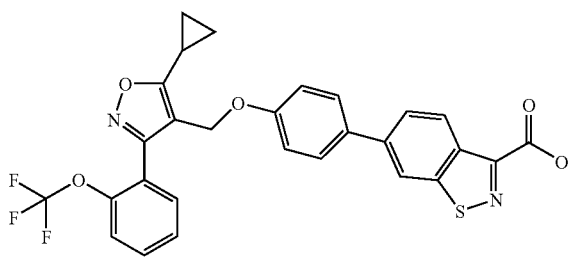

or a pharmaceutically acceptable salt thereof.

7. The compound 6-{4-[5-Cyclopropyl-3-(2-trifluoromethoxy-phenyl)-isoxazol-4-ylmethoxy]-phenyl}-1-methyl-1H-indazole-3-carboxylic acid

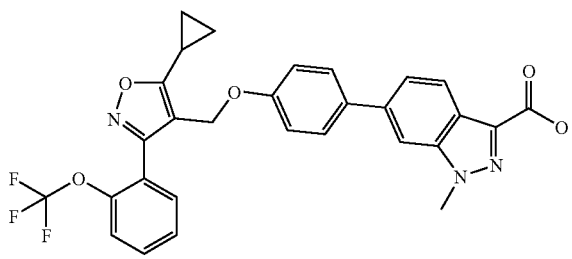

or a pharmaceutically acceptable salt thereof.

8. The compound 6-{4-[3-(2,6-Dichloro-phenyl)-5-isopropyl-isoxazol-4-ylmethoxy]-phenyl}-1-isopropyl-1H-indole-3-carboxylic acid

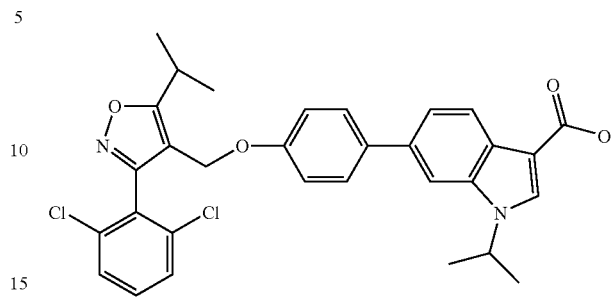

or a pharmaceutically acceptable salt thereof.

9. A method of treating dyslipidemia comprising administering a therapeutically effective amount of a compound according to claim 1 or a pharmaceutically acceptable salt thereof to a patient in need thereof.

10. A method of raising plasma HDL levels comprising administering a therapeutically effective amount of a compound according to claim 1 or a pharmaceutically acceptable salt thereof to a patient in need thereof.

11. A method for lowering LDL cholesterol levels comprising administering a therapeutically effective amount of a compound according to claim 1 or a pharmaceutically acceptable salt thereof to a patient in need thereof.

12. A method for lowering plasma triglycerides comprising administering a therapeutically effective amount of a compound according to claim 1 or a pharmaceutically acceptable salt thereof to a patient in need thereof.

13. A method of treating atherosclerosis comprising administering a therapeutically effective amount of a compound of according to claim 1 or a pharmaceutically acceptable salt thereof to a patient in need thereof.

14. A method of treating diabetes and complications thereof comprising administering a therapeutically effective amount of a compound according to claim 1 or a pharmaceutically acceptable salt thereof to a patient in need thereof.

15. A pharmaceutical composition comprising a compound according to claim 1 or a pharmaceutically acceptable salt thereof, and a carrier, diluent, or excipient.

* * * * *